(12) United States Patent
Waxman et al.

(10) Patent No.: US 11,686,677 B2
(45) Date of Patent: Jun. 27, 2023

(54) SYSTEMS AND METHODS FOR LEAK MONITORING VIA MEASUREMENT OF OPTICAL ABSORPTION USING TAILORED REFLECTOR INSTALLMENTS

(71) Applicant: MultiSensor Scientific, Inc., Cambridge, MA (US)

(72) Inventors: Allen M. Waxman, Newton, MA (US); Stefan Bokaemper, Newton, MA (US); Terrence K. Jones, Sharon, MA (US); Claude V. Robotham, Somerville, MA (US)

(73) Assignee: MultiSensor Scientific, Inc., Cambridge, MA (US)

( * ) Notice: Subject to any disclaimer, the term of this patent is extended or adjusted under 35 U.S.C. 154(b) by 135 days.

(21) Appl. No.: 17/424,311

(22) PCT Filed: Jan. 24, 2020

(86) PCT No.: PCT/US2020/014990
§ 371 (c)(1),
(2) Date: Jul. 20, 2021

(87) PCT Pub. No.: WO2020/154619
PCT Pub. Date: Jul. 30, 2020

(65) Prior Publication Data
US 2022/0099568 A1    Mar. 31, 2022

Related U.S. Application Data

(63) Continuation-in-part of application No. 16/413,272, filed on May 15, 2019, now Pat. No. 10,976,245.
(Continued)

(51) Int. Cl.
*G01N 21/359* (2014.01)
*G01N 21/3504* (2014.01)

(52) U.S. Cl.
CPC ....... *G01N 21/359* (2013.01); *G01N 21/3504* (2013.01); *G01N 2201/061* (2013.01); *G01N 2201/0636* (2013.01)

(58) Field of Classification Search
CPC ............. G01N 21/359; G01N 21/3504; G01N 2201/061; G01N 2201/0636
See application file for complete search history.

(56) References Cited

U.S. PATENT DOCUMENTS 3,517,190 A    6/1970   Astheimer
3,662,171 A    5/1972   Brengman et al.
(Continued)

FOREIGN PATENT DOCUMENTS

CN    1479866 A    3/2004
CN    1888865 A    1/2007
(Continued)

OTHER PUBLICATIONS

Benson, R. et al., Standoff passive optical leak detection of volatile organic compounds using a cooled InSb based infrared imager, Proceedings of the Air & Waste Management Assoc. Conf. Extended Abstract No. 06-A-131-AQMA, pp. 1-10 (2006).
(Continued)

*Primary Examiner* — Blake C Riddick
(74) *Attorney, Agent, or Firm* — Choate, Hall & Stewart LLP; William R. Haulbrook; Ronen Adato

(57) ABSTRACT

Presented herein are systems and methods directed to a multispectral absorption-based imaging approach offering improved detection, localization, and quantification of gas emission. The imaging technology described herein utilizes an optical sensor and broadband illumination in combination with specialized reflector installments mounted about the site. The optical sensor detects light (e.g., reflected) from locations along the reflector installment. Lines-of-sight from
(Continued)

the optical sensor to locations along the reflector installment sweep out an "optical curtain" partially enclosing and/or forming a boundary near various assets to be monitored. Optical absorption signatures from leaking gas crossing the optical curtain can be used to detect, localize, and obtain quantitative measures characterizing the leak. Measurements from reflector installments can be combined with measurements obtained via reflection of ambient light from background materials in a hybrid approach that expands monitoring capabilities and offers improvements in detection.

28 Claims, 32 Drawing Sheets

Related U.S. Application Data

(60) Provisional application No. 62/797,065, filed on Jan. 25, 2019.

(56) References Cited

U.S. PATENT DOCUMENTS

| | | |
|---|---|---|
| 4,264,209 A | 4/1981 | Brewster |
| 4,490,613 A | 12/1984 | Brame |
| 4,543,481 A | 9/1985 | Zwick |
| 4,555,627 A | 11/1985 | McRae, Jr. |
| 4,864,127 A | 9/1989 | Brame |
| 4,999,498 A | 3/1991 | Hunt et al. |
| 5,103,675 A | 4/1992 | Komninos |
| 5,281,816 A | 1/1994 | Jacobson et al. |
| 5,306,913 A | 4/1994 | Noack et al. |
| 5,656,813 A | 8/1997 | Moore et al. |
| 6,061,141 A | 5/2000 | Goldenberg et al. |
| 6,680,778 B2 | 1/2004 | Hinnrichs et al. |
| 6,690,472 B2 | 2/2004 | Kulp et al. |
| 7,075,653 B1 | 7/2006 | Rutherford |
| 7,486,399 B1 | 2/2009 | Reichardt et al. |
| 7,649,174 B2 | 1/2010 | Mammen et al. |
| 7,977,639 B2 | 7/2011 | Maillart et al. |
| 8,193,496 B2 | 6/2012 | Furry |
| 8,426,813 B2 | 4/2013 | Furry |
| 8,730,477 B2 | 5/2014 | Ruhland et al. |
| 8,994,928 B2 | 3/2015 | Shiraishi |
| 9,228,938 B2 | 1/2016 | Hager et al. |
| 9,658,059 B2 | 5/2017 | Metzler et al. |
| 9,955,910 B2 | 5/2018 | Fright et al. |
| 10,031,040 B1 | 7/2018 | Smith et al. |
| 10,190,976 B2 | 1/2019 | Waxman et al. |
| 10,197,470 B2 | 2/2019 | Waxman et al. |
| 10,330,593 B1 | 6/2019 | Dobler et al. |
| 10,371,627 B2 | 8/2019 | Waxman et al. |
| 10,436,710 B2 | 10/2019 | Waxman et al. |
| 10,921,243 B2 | 2/2021 | Waxman et al. |
| 10,976,245 B2 | 4/2021 | Waxman et al. |
| 11,143,572 B2 | 10/2021 | Waxman et al. |
| 11,493,437 B2 | 11/2022 | Waxman et al. |
| 2002/0071122 A1 | 6/2002 | Kulp et al. |
| 2004/0051043 A1 | 3/2004 | Kilian et al. |
| 2006/0202122 A1 | 9/2006 | Gunn et al. |
| 2006/0203248 A1 | 9/2006 | Reichardt et al. |
| 2008/0069177 A1 | 3/2008 | Minor et al. |
| 2009/0296202 A1 | 12/2009 | Wei et al. |
| 2010/0127173 A1 | 5/2010 | Schmidt |
| 2010/0231722 A1 | 9/2010 | Hill, Jr. et al. |
| 2010/0241361 A1 | 9/2010 | Hofvander et al. |
| 2012/0062697 A1 | 3/2012 | Treado et al. |
| 2012/0062740 A1 | 3/2012 | Treado et al. |
| 2013/0118339 A1 | 5/2013 | Lee et al. |
| 2013/0248673 A1 | 9/2013 | Townsend, Jr. |
| 2013/0327942 A1 | 12/2013 | Silny |
| 2014/0002667 A1 | 1/2014 | Cheben et al. |
| 2014/0008526 A1 | 1/2014 | Zeng et al. |
| 2014/0104607 A1 | 4/2014 | Treado et al. |
| 2014/0118722 A1 | 5/2014 | Treado et al. |
| 2014/0160479 A1 | 6/2014 | Hager et al. |
| 2014/0268104 A1 | 9/2014 | Treado et al. |
| 2015/0069239 A1 | 3/2015 | Kester et al. |
| 2015/0316473 A1 | 11/2015 | Kester et al. |
| 2015/0323449 A1 | 11/2015 | Jones et al. |
| 2016/0037144 A1 | 2/2016 | Schultz et al. |
| 2016/0069743 A1 | 3/2016 | McQuilkin et al. |
| 2016/0097713 A1 | 4/2016 | Kester et al. |
| 2016/0131576 A1 | 5/2016 | Cabib et al. |
| 2016/0334538 A1 | 11/2016 | Rieker et al. |
| 2016/0345835 A1 | 12/2016 | Darty |
| 2016/0349228 A1 | 12/2016 | Kester et al. |
| 2017/0108874 A1 | 4/2017 | Peters et al. |
| 2017/0234761 A1 | 8/2017 | Augusto |
| 2017/0284891 A1 | 10/2017 | Miranda |
| 2017/0336281 A1 | 11/2017 | Waxman et al. |
| 2017/0336320 A1 | 11/2017 | Yalin |
| 2018/0045596 A1 | 2/2018 | Prasad et al. |
| 2018/0131449 A1 | 5/2018 | Kare et al. |
| 2018/0231684 A1 | 8/2018 | Jones et al. |
| 2018/0266944 A1 | 9/2018 | Waxman et al. |
| 2019/0137390 A1 | 5/2019 | Waxman et al. |
| 2019/0145891 A1 | 5/2019 | Waxman et al. |
| 2019/0170900 A1 | 6/2019 | Rieker et al. |
| 2019/0195725 A1 | 6/2019 | Waxman et al. |
| 2019/0277753 A1 | 9/2019 | Waxman et al. |
| 2020/0240906 A1 | 7/2020 | Waxman et al. |
| 2021/0223169 A1 | 7/2021 | Waxman et al. |

FOREIGN PATENT DOCUMENTS

| | | |
|---|---|---|
| CN | 101529219 A | 9/2009 |
| CN | 101608997 A | 12/2009 |
| CN | 101680833 A | 3/2010 |
| CN | 101696897 A | 4/2010 |
| CN | 103403577 A | 11/2013 |
| CN | 103503135 A | 1/2014 |
| CN | 104081156 A | 10/2014 |
| CN | 104101571 A | 10/2014 |
| CN | 104122039 A | 10/2014 |
| CN | 104697718 A | 6/2015 |
| CN | 205049297 U | 2/2016 |
| CN | 105675532 A | 6/2016 |
| CN | 205562132 U | 9/2016 |
| CN | 106124130 A | 11/2016 |
| EP | 3040706 A1 | 7/2016 |
| JP | H05264446 A | 10/1993 |
| TW | 201625923 A | 7/2016 |
| WO | WO-02/27297 A1 | 4/2002 |
| WO | WO-2017/201194 A1 | 11/2017 |
| WO | WO-2018/170438 A1 | 9/2018 |
| WO | WO-2019/099096 A1 | 5/2019 |
| WO | WO-2020/154619 A2 | 7/2020 |

OTHER PUBLICATIONS

Buchwitz, M. et al., Atmosphere methane and carbon dioxide from SCIAMACHY satellite data, Atmos. Chem. Phys., 5:941-962 (2005).
Byer, R. L. and Shepp, L. A., Two-dimensional remote air-pollution monitoring via tomography, Optics Letters, 4(3):75-77 (1979).
Clark, R. N. et al., Reflectance spectroscopy of organic compounds: Alkanes, J. Geophysical Research, 114:E030001:1-19, (2009).
Epperson, D. et al., Equivalent Leak Definitions for Smart LDAR (Leak Detection and Repair) When Using Optical Imaging Technology, Journal of the Air & Waste Management Association, 57(9):1050-1060, (2007).
Furry, D. et al., Detection of Volatile Organic Compounds (VOC's) with a Spectrally Filtered Cooled Mid-Wave Infrared Camera, Information Proceedings, Document No. ITC 108A Jun. 1, 2005, 6 pages, (2005).
Gottwald, M. et al., The Instrument, Chapter 3 in SCIAMACHY—Exploring the Changing Earth's Atmosphere, pp. 29-46, (2006).
Gross, W. et al., Localization of Methane Distributions by Spectrally Tuned Infrared Imaging, SPIE, Part of the SPIE Conference

(56) References Cited

OTHER PUBLICATIONS on Air Monitoring and Detection of Chemical and Biological Agents, 3533:234-240, (1998).

Inada, H. et al., Uncooled SWIR InGaAs/GaAsSb type II quantum wells focal plane array, Proc. of SPIE, Infrared Technology and Applications XXXVI. 7660:76603N-1-76603N-7 (2010).

Shulz, M. et al., High-resolution thermophysical measurements using staring infrared detector arrays, High Temperatures—High Pressures, 32:547-556 (2000).

Van Den Bosch, C. J. H. and Duijm, N. J., Overflow and Spray release, Chapter 2, Methods for Calculation of Physical Effects: Due to Release of Hazardous Materials (Liquids & Gases)., EDS: Van den Bosch et al., 3rd Ed. 2nd Printing, CPR 14E, TNO—The Netherlands Organization of Applied Scientific Research, pp. 2.1-2.179 (2005).

Zhaoci, L. et al., LNG continuous leakage and diffusion process simulation, CIESC Journal, 66(S2):158-165, (2015).

International Search Report for PCT/US2020/014990, filed Jan. 24, 2020, 7 pages, (dated Aug. 24, 2020).

Written Opinion for PCT/US2020/014990, filed Jan. 24, 2020, 15 pages, (dated Aug. 24, 2020).

Li, Jing, et al. Remote Sensing System of Natural Gas Leakage Based on Multiple Characteristic Wavelength Spectral Analysis, Spectroscopy and Spectral Analysis, 34(5): 1249-1252, (2014), English abstract and Machine Translation included.

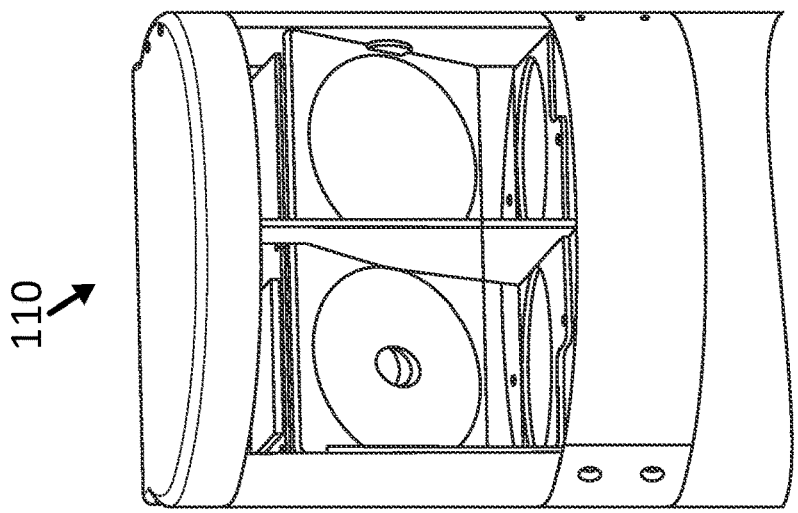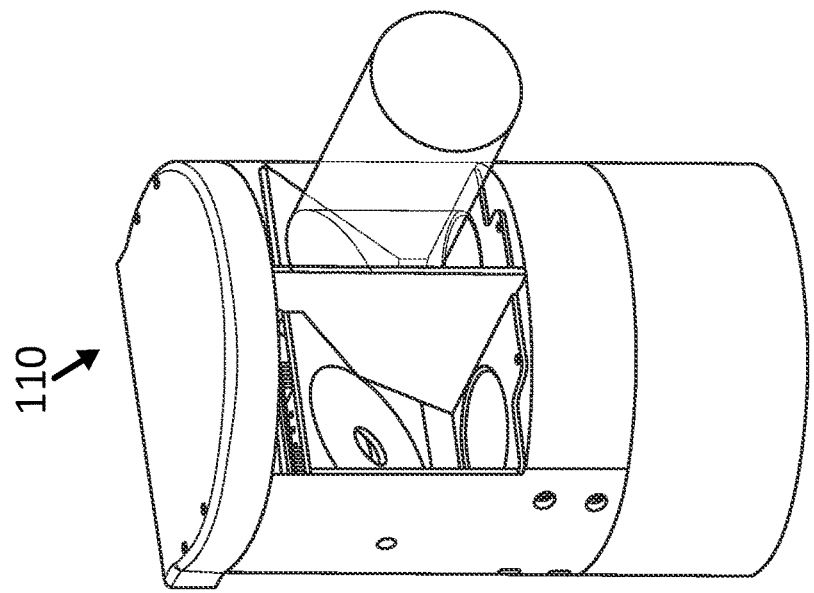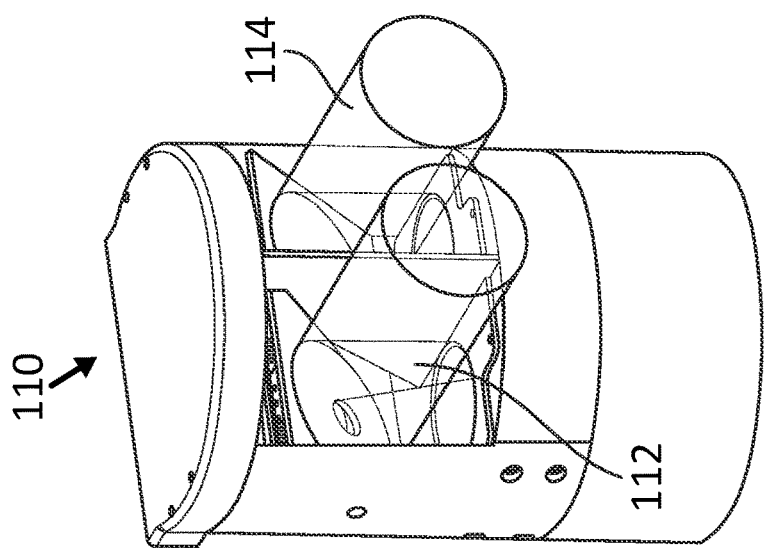
FIG. 1B

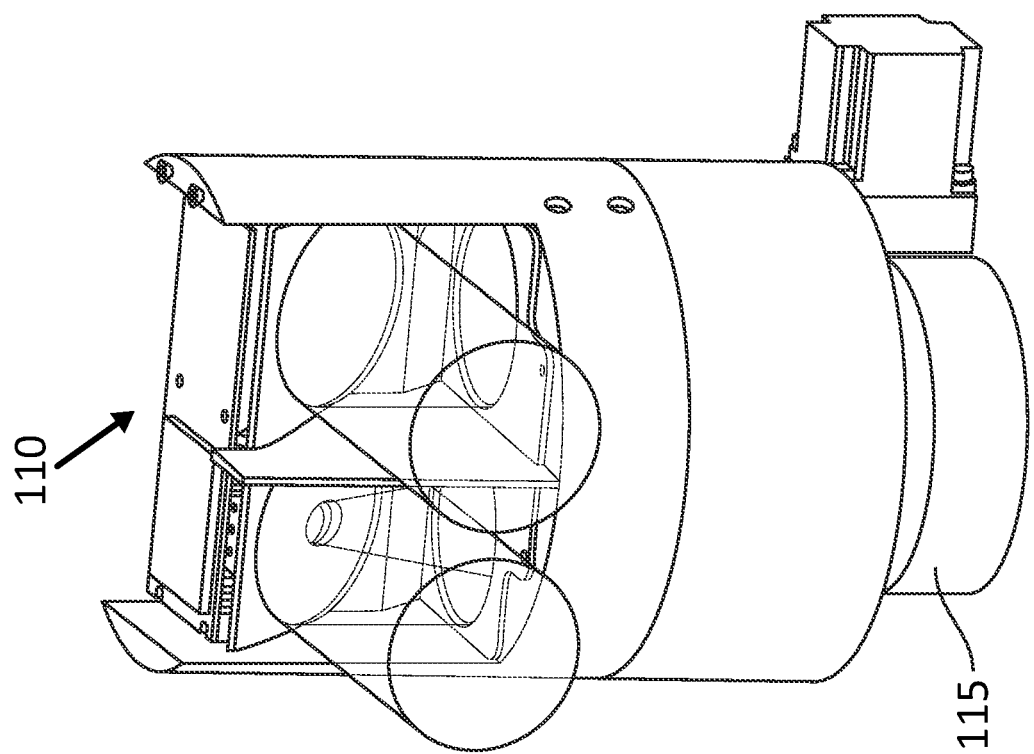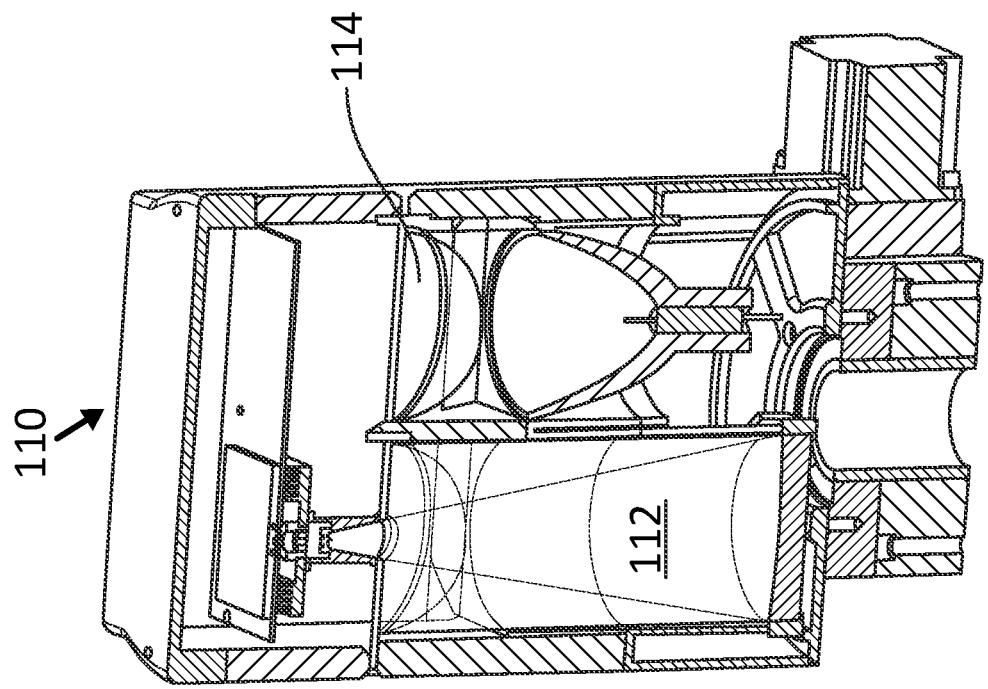
FIG. 1C

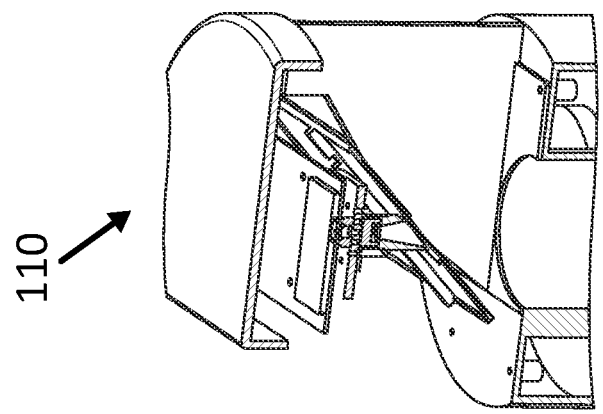
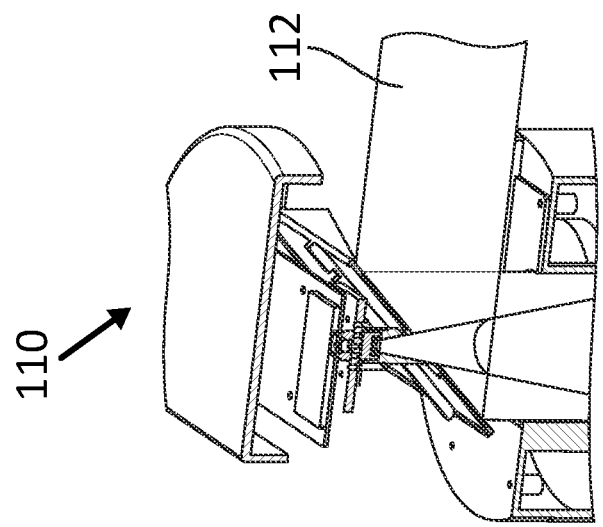
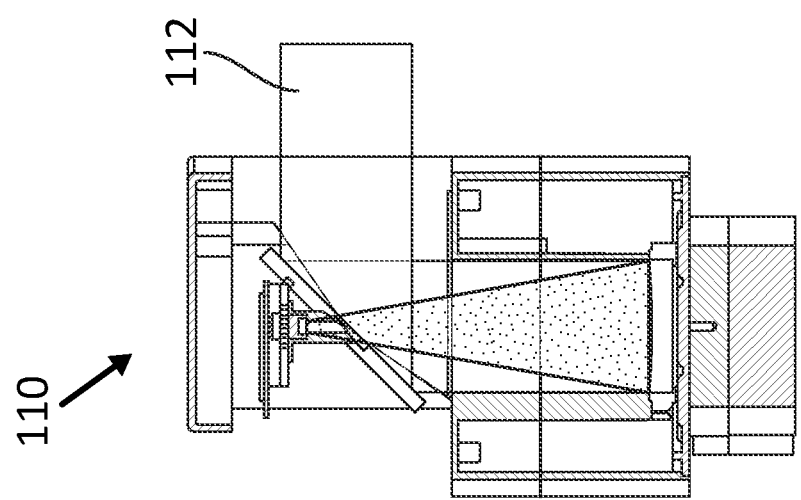
FIG. 1D

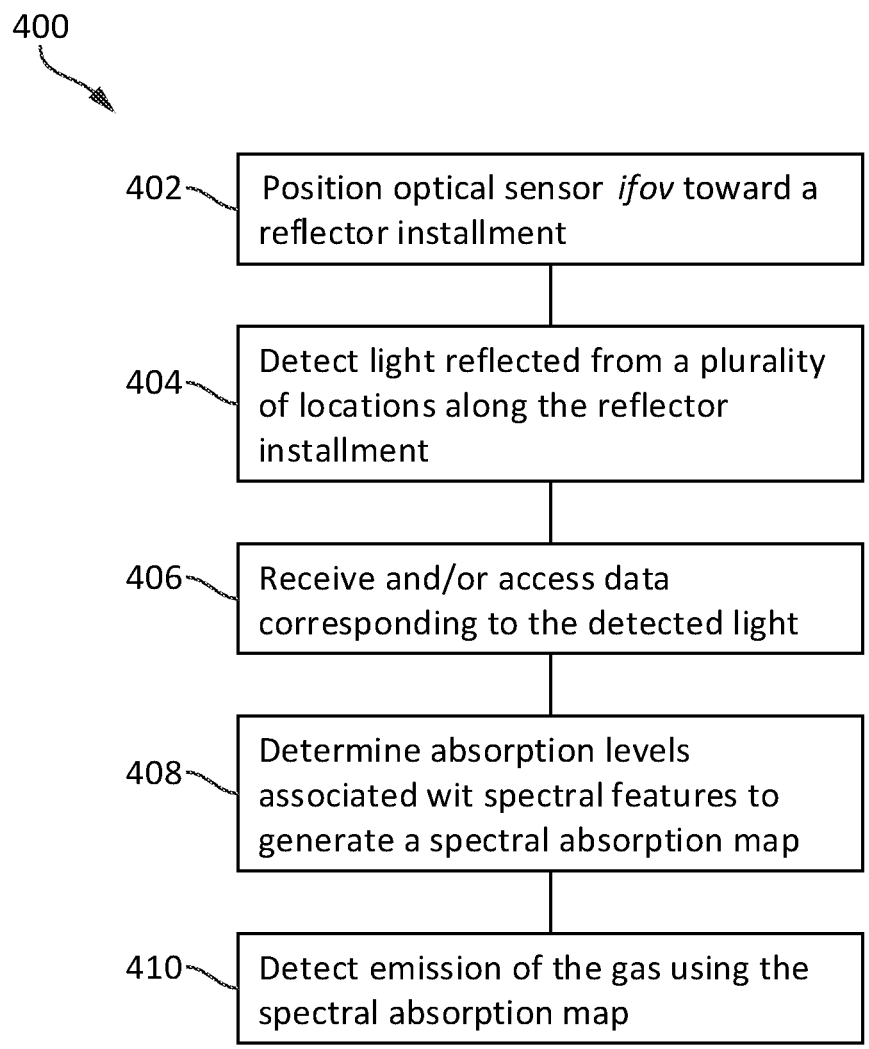

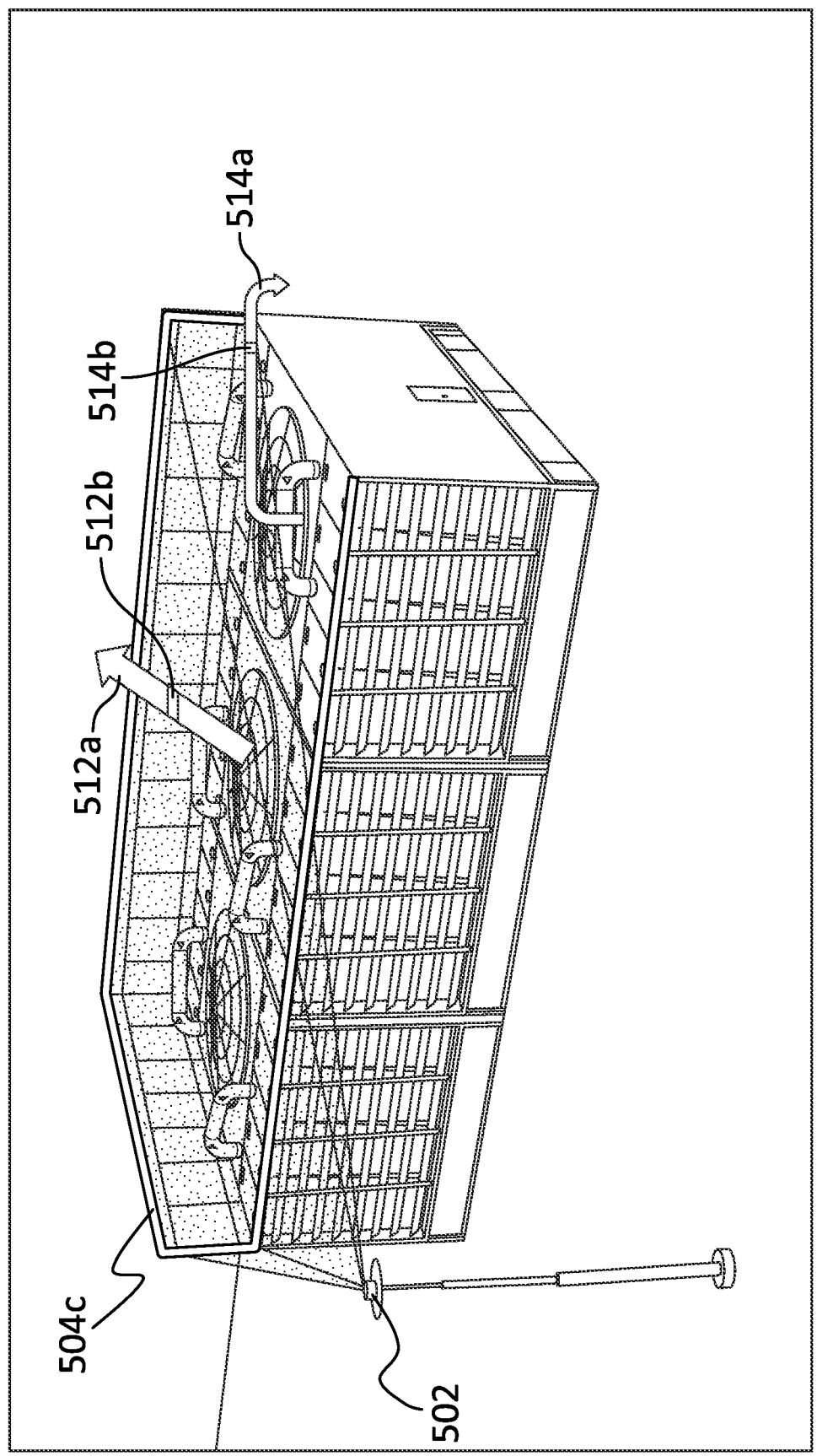

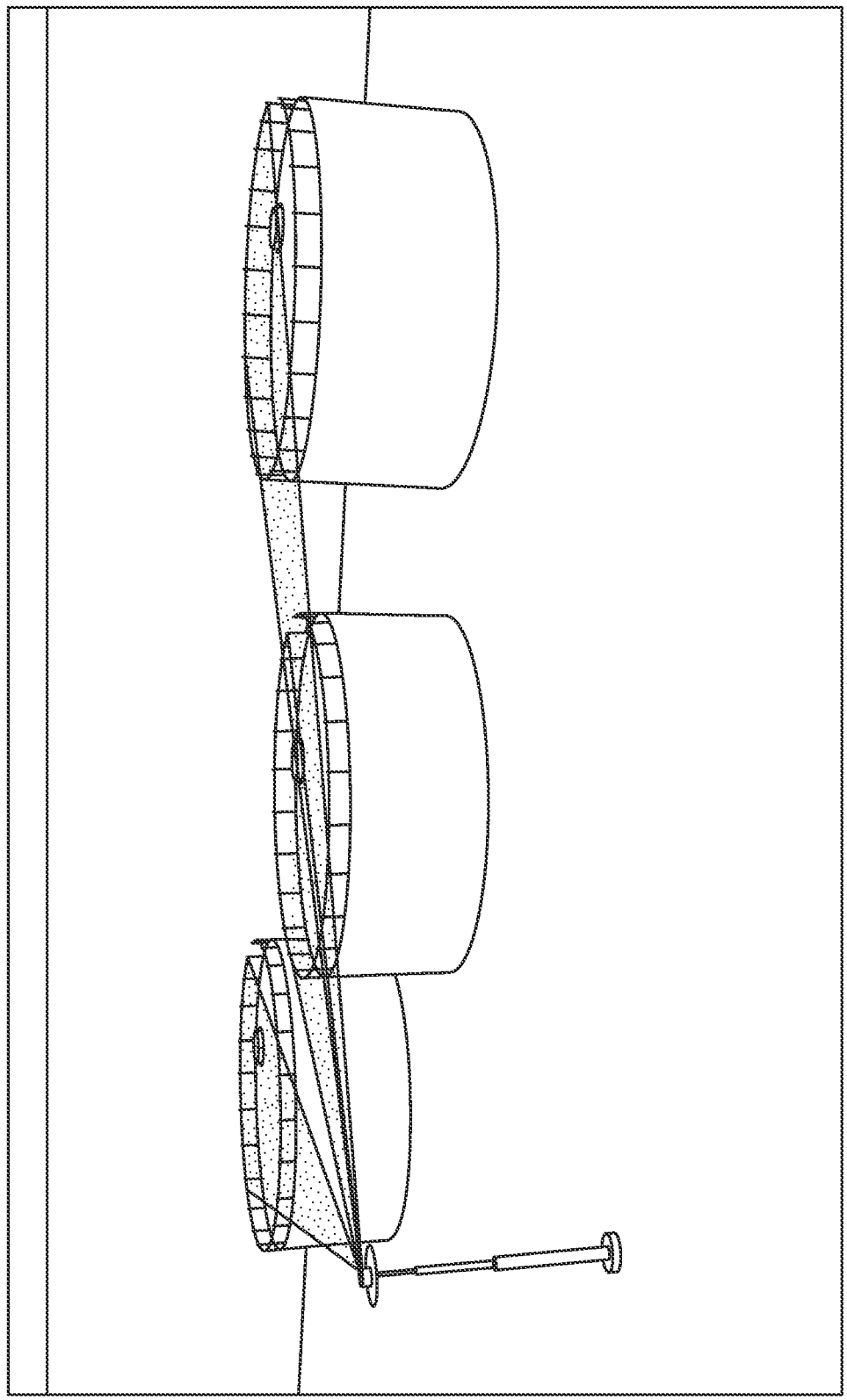

SYSTEMS AND METHODS FOR LEAK MONITORING VIA MEASUREMENT OF OPTICAL ABSORPTION USING TAILORED REFLECTOR INSTALLMENTS

CROSS-REFERENCE TO RELATED APPLICATIONS

This application is a national stage application, filed under 35 U.S.C. § 371, of International Patent Application No. PCT/US2020/014990, filed on Jan. 24, 2020, which claims priority to and benefit of U.S. patent application Ser. No. 16/413,272 (now issued as U.S. Pat. No. 10,976,245), entitled "Systems and Methods for Leak Monitoring via Measurement of Optical Absorption Using Tailored Reflector Installments" and filed May 15, 2019, and U.S. Provisional Patent Application No. 62/797,065, entitled "Systems and Methods for Leak Monitoring via Measurement of Optical Absorption Using Tailored Reflector Installments" and filed Jan. 25, 2019, the content of each of which is hereby incorporated by reference herein in its entirety.

FIELD OF THE INVENTION

This invention relates generally to methods, systems, and apparatus for detection of emission of gas, e.g., methane, other hydrocarbons, carbon dioxide or ammonia, via measurement of optical absorption and tailored reflector installments. In particular, in certain embodiments, this invention relates to methods, systems, and apparatus for detection, localization and quantification of emission of multiple gases from within a site to be monitored via a scanning illuminator co-located with an optical sensor in combination with the tailored reflector installment.

BACKGROUND OF THE INVENTION

Natural gas leaks create both safety and environmental hazards, and occur along the entire gas supply chain from the well to the street (so-called upstream, midstream, and downstream sectors). Methane, the primary constituent of natural gas, is combustible in air, and is also a potent greenhouse gas. Other hydrocarbons found in natural gas, as well as vapors emanating from liquids separated from gas and oil, include ethane, propane, butane, pentane, hexane, octane, ethylene and heavier hydrocarbons, which form volatile organic compounds that generate smog which is a health hazard. Thus, there are compelling reasons to detect leaks of gases comprising, for example, methane and other hydrocarbons, so that such leaks can be repaired. In addition, methane and carbon dioxide are of significance due to their forcing effects on climate change. Thus, detecting and quantifying these emissions are of environmental importance. Conventional point and line detectors for gases have limited spatial coverage for detection as they rely on wind or air movements to transport the gas towards the point or line detector. Such air currents can easily transport the gas away from point detectors and around the open sensing path of line detectors. For gas safety applications a high degree of asset coverage is desired, in order to maximize the degree of certainty that a gas leak from assets of interest is detected under all circumstances. Thus, a solution that increases the degree of detection coverage for assets in a given area is very desirable.

Beyond merely detecting the presence of leaking gas, localizing leaks to particular assets (or particular components) and quantifying the leak rate (e.g., emission flux of leaking gas) are important for allowing repair of leaks to be performed rapidly, and in a prioritized fashion. Quantification of leak rate also allows the impact (e.g., environmental impact) of leaking gas to be assessed. Detection, localization, and quantification of gas leaks is challenging, since leak monitoring and/or inspection typically need to be performed over wide areas, and from a safe and practical standoff distance.

Accordingly, there exists a need for improved systems and methods for detection, localization, and quantification of gas leaks. In particular, there is a need for systems and methods that allow for effective gas leak monitoring and/or inspection to be performed over wide areas in complex environments, and even in the presence of interfering background signals such as, for example, water vapor or steam. Cost effective solutions are particularly important, as they can be broadly adopted and utilized.

SUMMARY OF THE INVENTION

Presented herein are systems and methods directed to a multispectral absorption-based imaging approach that provides for rapid and accurate detection, localization, and quantification of gas emission from within a site to be monitored. The imaging technology described herein utilizes an optical sensor and broadband illumination in combination with specialized reflector installments mounted about the site. The optical sensor detects light from a plurality of sampled locations along the reflector installment, for example by imaging multiple sampled locations at a time and/or scanning an instantaneous field of view (ifov) of the optical sensor. Lines-of-sight from the optical sensor to sampled locations along the reflector installment sweep out an "optical curtain" partially enclosing and/or forming a boundary near various assets to be monitored (e.g., well-pads, compressor stations and compressor coolers, gathering stations, fracking rigs, LNG engines, platforms, tankers, landfills, temporary work sites including repairs of underground pipelines, and the like). If a leak is present, emitted gas crosses the optical curtain resulting in optical absorption that can be used to detect the leak, localize, and even obtain quantitative measures characterizing it, such as an emanating mass flux.

Detection based on the reflector installments and the optical curtains they provide for can be combined with measurements utilizing reflection of ambient light (e.g., sunlight) from sufficiently reflective and/or well illuminated (e.g., by natural sunlight) locations off of the reflector installments in a hybrid fashion. Such hybrid imaging approaches can provide, not only for efficient low-cost and low-power monitoring of a variety of assets across a site, but also allows for improvement in image processing and gas detection techniques. In particular, as described in further detail herein, data obtained from ambient light-based measurements can be used in combination with measurements taken using light reflected off of reflector installments to improve detection and reduce false positives, complete spatial representations of detected gas plumes, and provide additional/more complete inputs into modelling techniques used to localize leak sources and quantify leakage rates.

Accordingly, by strategically positioning tailored reflector installments, assets can be monitored for emissions of gases such as hydrocarbons (e.g., methane) emanating from vents, hatches, pipes, and other leaking components. The technology may be applied to monitoring assets in the oil and gas industry, petrochemical industry, and LNG transfer operations to vessels and vehicles, in environments that are outdoors, indoors, on shore, and off shore. Accordingly, the approaches described herein have implications in both environmental and safety monitoring applications.

In particular, in certain embodiments, the systems and methods described herein detect light within one or more specific spectral bands of interest that are selected to overlap with spectral features of various compounds to be detected. As light travels to the sensor, it may be absorbed by intervening gas (e.g., produced by a leak). Absorption of light by gas produces spectral signatures that are indicative of and specific to various compounds (e.g., hydrocarbons) that are present in the gas. Accordingly, by detecting light absorption in a spectrally sensitive manner (e.g., using various spectral filters placed in front of one or more detectors) different gases and compounds present therein can be detected and identified. As the optical sensor is scanned along the reflector installment, a multispectral absorption map can be created and used to detect and quantify gas leaks.

In certain embodiments, spectral bands within the short-wave infrared (SWIR) region (e.g., from about 1.0 to 2.6 microns) are of particular interest. This wavelength range includes spectral features associated with a number of important hydrocarbon compounds, such as methane, ethane, propane, butane, pentane, hexane, octane, ethylene and other hydrocarbons, as well as carbon dioxide and ammonia, and also offers advantages such as reduced atmospheric water vapor absorption and the possibility of sensitive detection without needing to use specialized (e.g., liquid nitrogen cooled) detectors.

In particular, thermal IR gas cameras suitable for gas leak detection and leak localization (single spectral band or multispectral) are available, but are very expensive (US$100,000 or more). Such cameras detect and image methane and other hydrocarbons, but rely on the temperature difference between the gas and background objects in the scene. Specifically, they utilize emitted IR radiation (also referred to as thermal emissions or thermal radiation) of gas and of objects in the mid-wave and long-wave infrared region (about 3 microns to 12 microns) as part of their approach to gas detection and towards creating a visual image of gas.

A significant shortcoming of such thermal emission based approaches is that they requires sufficient temperature contrast between the thermal radiation of a background object and the gas passing in front of said object. It is often the case that the gas emissions lack sufficient thermal contrast (particularly in cold weather outdoors) to reliably detect the gas. For example, due to the lack of thermal contrast, thermal IR gas cameras are not effective in detecting gas emissions due to underground leaks that are percolating through ground surface materials. Thermal-based imaging in the mid- and/or long-wave IR spectral domain also suffers from spectral mixing or confusion due to the varying emission spectrum of the background object or material, which is challenging to measure absolutely or to estimate in a complex environment. This causes great difficulty in attempts to automate the detection of emissions with computer algorithms and causes frequent false positive alarms by such computer algorithms. Automatic detection of emissions by a computer algorithm is highly desirable as it significantly reduces or eliminates the cost of human operators, especially for permanently installed cameras. Moreover, thermal IR gas cameras frequently confuse water vapor and steam with gas since water vapor absorption bands and gas absorption bands overlap in many regions of the mid-wave and longwave infrared spectrum. Moreover, thermal imaging cameras measure temperature differences and as such have to infer column density of gas present by indirect computational techniques. This often causes a larger error in estimating emission flux in comparison with methods that directly measure column density of gas.

Instead, the approaches described herein utilize multi-spectral imaging in the short-wave infrared (SWIR) spectral region. There are significant advantages in using a multi-spectral short-wave IR (SWIR) sensor to image and quantify gas emissions. Such sensors do not rely on thermal contrast or on measuring thermal radiation emitted by bodies or by gas, and instead form imagery of gas based on the absorption of SWIR light provided in natural sunlight or by an artificial illuminator. The detected light is, accordingly, fundamentally distinct in terms of its physical origin and behavior. In particular, while black body radiators at ambient temperatures are prevalent on earth, they emit radiation primarily in the mid- and long-wave infrared spectral regions, but do not emit meaningful amounts of radiation in the SWIR band. Moreover, SWIR sensors can also detect methane and other hydrocarbons in the presence of steam and water vapor, unlike most thermal IR gas cameras. SWIR gas scanning imagers also cost significantly less than thermal IR gas cameras.

Moreover, by increasing the amount of light that is directed back, from either a dedicated illumination source or ambient light, including solar illumination, use of tailored reflector installments offers a flexible and relatively inexpensive way to significantly increase range on detection systems, e.g., without needing to dramatically increase a power of an illumination source. Imaging systems designed in accordance with the approaches described herein can, accordingly, be widely implemented for gas emission monitoring of various sites of interest. For example, in certain embodiments, a reflective material (e.g., glass bead or prismatic retroreflective tape, retroreflective paint, loose retro-reflector spheres or crystals, etc.) can be placed on and/or nearby various assets of interest, such as compressors, gas storage tanks, or vehicles. Tailored panels and/or frames can also be mounted on, or so as to partially surround, assets to be monitored. Such reflective panels can also be mounted onto relocatable structures, such as posts mounted on stands or wheeled platforms, such that they may be deployed temporarily at work sites. Thus, the approaches described herein can be utilized anywhere that can accommodate permanent or temporary installation of an optical sensor and the placement of a reflective material and/or sections on or near assets or areas to be monitored for gas emissions.

Accordingly, by providing imaging technologies capable of performing rapid and effective multi-spectral absorption-based imaging over wide areas and at distance, the systems and methods described herein overcome a number of challenges associated with previous systems and methods for detecting gas leaks and facilitate a variety of gas leak, emissions, and safety monitoring applications.

In one aspect, the invention is directed to a method of generating a spectral absorption map for detecting emission of gas comprising one or more compounds of interest [e.g., hydrocarbon compounds (e.g., methane, ethane, propane, butane, pentane, hexane, octane, ethylene, and other hydrocarbons); e.g., other compounds such as carbon dioxide and ammonia], the method comprising: (a) positioning an instantaneous field of view (ifov) of an optical sensor toward a reflector installment mounted about a site to be monitored; (b) detecting (e.g., in a spectrally selective manner), with one or more detectors of the optical sensor, light within one or more spectral bands of interest [e.g., the one or more spectral bands of interest lying within the short-wave infrared (SWIR) spectrum (e.g., ranging from about 1.0 to 2.6 microns); e.g., the one or more spectral bands of interest lying within the visible through near-infrared spectrum (e.g., ranging from about 0.4 to 1.0 microns)], the detected light having been reflected from a plurality of sampled locations on the reflector installment [e.g., at least a portion of the plurality of sampled locations spaced sufficiently close (e.g., no greater than 1 meter apart; e.g., no greater than 50 cm apart; e.g., no greater than 25 cm apart; e.g., no greater than 10 cm apart; e.g., no greater than 1 cm apart) so as to provide a spatial resolution and/or angular resolution (e.g., between neighboring lines-of-sight from sampled locations to the optical sensor) (e.g., such that an angle between adjacent lines of sight from the optical sensor to neighboring sampled locations is sufficiently small (e.g., no greater than 0.1 radians; e.g., no greater than 0.05 radians; e.g., no greater than 0.01 radians; e.g., no greater than 0.001 radians; e.g., no greater than 10-4 radians; e.g., no greater than 5×10-5 radians)) commensurate with (e.g., sufficiently fine to detect; e.g., smaller than) a characteristic size of the emission of the gas (e.g., of a typical cloud or plume)] and captured within the ifov of the optical sensor, wherein at least a portion of the one or more spectral bands of interest overlap with one or more spectral features associated with [e.g., spectral absorption due to (e.g., and indicative of presence of)] the one or more compounds of interest {e.g., thereby detecting light travelling along lines-of-sight from each sampled location to the optical sensor and/or an illumination source (e.g., co-located with the optical sensor), to form an optical curtain (e.g., a surface substantially confined to a 2D plane; e.g., a surface not confined to a 2D plane and varying in 3D space) at least partially enveloping, and/or forming at least a partial boundary of, at least a portion of the site, or creating a surface that divides a site into multiple sectors [e.g., such that the optical curtain partially encloses a volume (e.g., comprising one or more assets being monitored), and/or forms an at least partial boundary of a volume (e.g., comprising one or more assets being monitored), from within which the emission of the gas can be detected; e.g., whereby gas emitted from within the volume crosses the optical curtain (formed by the lines-of-sight from each sampled location to the optical sensor), e.g., whereby gas emitted from one sector crosses the optical curtain into the other sector, resulting in detectable absorption (e.g., within at least a portion of the one or more spectral bands of interest) of light reflected from locations along the reflector installment as the light travels back to the optical sensor]}; (c) receiving and/or accessing, by a processor of a computing device, data corresponding to the detected light reflected from the plurality of sampled locations (e.g., wherein the plurality of sampled locations along the reflector installment define a surface corresponding to a segment of the reflector installment); and (d) determining, by the processor, for each of at least a portion of the plurality of sampled locations, an absorption level associated with (e.g., due to) at least one of the one or more spectral features using the detected light, thereby generating a spectral absorption map comprising a plurality of absorption levels, each associated with a particular sampled location and spectral feature.

In certain embodiments, the method comprises (e) detecting [e.g., by the processor (e.g., automatically)] the emission of the gas from within the site to be monitored using the generated spectral absorption map.

In certain embodiments, step (e) comprises detecting the emission of the gas by automatically analyzing, by the processor, the absorption levels of the spectral absorption map [e.g., by comparing at least a portion of the absorption levels (e.g., associated with a single spectral feature; e.g., associated with multiple spectral features) with one or more threshold values; e.g., by identifying regions of pixels (each pixel corresponding to a particular sampled location) wherein a measure of an absorption level in the region (e.g., a minimum, a median, a mean, etc.) is above a particular threshold value].

In certain embodiments, the method comprises using the absorption levels of the spectral absorption map to determine, by the processor, for each of at least a portion of the plurality of sampled locations, a column density [e.g., a value representing, for a particular sampled location, a number of gas molecules in between (e.g., along a line of sight) the optical sensor and the particular sampled location] of one or more of the compounds of interest [e.g., thereby creating an image representing gas concentration across a region of space in between the optical sensor and the reflector installment, the image comprising a plurality of pixels, each corresponding to a particular sampled location and having a value representing the column density determined for the particular sampled location].

In certain embodiments, the method comprises directing a beam of illumination from an illumination source (e.g., an illumination source co-located with the optical sensor) and toward the reflector installment; and scanning the beam of illumination across at least a portion of the reflector installment, thereby illuminating the plurality of sampled locations (e.g., wherein the beam of illumination illuminates one or more of the sampled locations at a time as it is scanned) (e.g., such that the detected light is light from the illumination source that is reflected back to the optical sensor by the reflector installment).

In certain embodiments, the method comprises scanning the beam of illumination in a continuous fashion across a portion of a target region comprising the reflector installment, thereby illuminating the plurality of sampled locations along the reflector installment as well as other locations within the target region, not necessarily on the reflector installment.

In certain embodiments, the illumination source is a broadband source, such that the beam of illumination has a spectral bandwidth spanning a plurality of spectral features of [e.g., spectral absorption due to (e.g., and indicative of presence of)] the one or more compounds of interest [e.g., wherein the beam of illumination has a spectral bandwidth of at least 200 nanometer (e.g., at least 500 nanometers; e.g., at least 1000 nanometers; e.g. at least 2000 nanometers)]. In certain embodiments, the illumination source is a broadband short-wave infrared (SWIR) source [e.g., having a bandwidth of approximately 500 nanometer or more in the SWIR region (e.g., ranging from about 1.0 microns to 2.6 microns)].

In certain embodiments, the method comprises scanning the ifov of the optical sensor across the portion of the reflector installment in a synchronized fashion with the beam of illumination (e.g., so as to maintain overlap between illuminated locations on the reflector installment and the ifov of the sensor) and detecting, within the one or more spectral bands of interest, with the one or more detectors, the light reflected from each of the sampled locations along the reflector installment as the ifov is scanned [e.g., wherein the ifov captures light reflected from one or more of the sampled locations at time as it is scanned (e.g., wherein the ifov captures light reflected from a single sampled location at a time; e.g., wherein the ifov captures light from a plurality of sampled locations at a time (e.g., the one or more detectors comprising a plurality of pixels for sampling a plurality of spatial locations at a time))].

In certain embodiments, the illumination source is co-located with (e.g., and mechanically coupled to) the optical sensor [e.g., both located in close proximity to each other; e.g., both using a same rotatable mirror to receive and/or send light, e.g., mounted together on a rotation stage or a pan-tilt stage)], and wherein the method comprises scanning the beam of illumination and the ifov in tandem.

In certain embodiments, the ifov and the beam of illumination are scanned using mechanically coupled mirrors.

In certain embodiments, the method comprises scanning the ifov of the optical sensor across the portion of the reflector installment and detecting, within the one or more spectral bands of interest, with the one or more detectors, light reflected from each of the sampled locations along the reflector installment as the ifov is scanned [e.g., wherein the ifov captures light reflected from one or more of the sampled locations at time as it is scanned (e.g., wherein the ifov captures light reflected from a single sampled location at a time; e.g., wherein the ifov captures light from a plurality of sampled locations at a time (e.g., the one or more detectors comprising a plurality of pixels for sampling a plurality of spatial locations at a time)); e.g., wherein ambient light (e.g., sunlight) is sufficient to generate detectable signal (e.g., and no dedicated illumination source is needed)].

In certain embodiments, step (b) comprises detecting light from a plurality of image locations within a target region, wherein the target region comprises the reflector installment (e.g., the reflector installment is positioned within the target region) and the image locations comprise the plurality of sampled locations on the reflector installment, as well as other locations within the target region, not necessarily on the reflector installment (e.g., by scanning the ifov of the optical sensor in a continuous fashion across a portion of the target region).

In certain embodiments, step (c) comprises receiving and/or accessing data corresponding to the detected light from the plurality of image locations within the target region; and step (d) comprises determining, for each of the plurality of image locations (e.g., the plurality of sampled locations along the reflector installment, as well as other locations, not necessarily on the reflector installment), an absorption level associated with (e.g., due to) at least one of the one or more spectral features using the detected light, such that the generated spectral absorption map comprises a plurality of absorption levels, each associated with a particular image location and spectral feature.

In certain embodiments, the reflector installment comprises one or more continuous reflective sections of sufficient size to span a plurality of the sampled locations [e.g., two or more of the sampled locations are on a same, continuous, reflective surface; e.g., each continuous reflective section is at least twice (e.g., at least five times; e.g., at least ten times; e.g., at least 20 times) as large as an individual ifov of each of the one or more detectors along at least one dimension].

In certain embodiments, the reflector installment comprises one or more continuous reflective sections each comprising a plurality of individual retro-reflective elements (e.g., the reflection sections are panels comprised over many tiny retro-reflectors that cover extended strips or areas, as opposed to discreet corner cube reflectors that occupy points not areas or strips).

In certain embodiments, the one or more detectors comprise an array detector comprising a plurality of pixels and aligned to image a spatial region comprising two or more of the sampled locations (e.g., a two-dimensional focal plane array detector aligned to image a two-dimensional spatial region; e.g., a two-dimensional focal plane array detector aligned to image a one-dimensional spatial region; e.g., a one-dimensional array detector).

In certain embodiments, the one or more detectors are aligned to image a single spatial location at a time (e.g., a point detector comprising a single pixel; e.g., an array detection (e.g., a quadrant detector) comprising a plurality of pixels aligned to detect light from a substantially same spatial location (e.g., each pixel detecting light from within a different spectral band of interest)].

In certain embodiments, the reflector installment comprises one or more reflective sections mounted in proximity to (e.g., behind with respect to a location of the optical sensor; e.g., at least partially encircling; e.g., encircling), and/or mounted on, one or more assets [(e.g., one or more well pads; e.g., one or more compressor coolers; e.g., one or more fracking rigs; one or more liquid natural gas engines (e.g., of a ship); e.g., one or more floating liquid natural gas platforms; e.g., one or more liquid natural gas tankers; e.g., liquid natural gas loading/unloading equipment)] within the site (e.g., wherein the site is an interior site; e.g., wherein the site is an off-shore site; e.g., wherein the site is a liquid natural gas loading site; e.g., wherein the site is a temporary repair operations site; e.g., wherein the site is a plant undergoing commissioning and/or turnaround).

In certain embodiments, the reflector installment comprises one or more reflective sections, each comprising a reflective surface [e.g., the reflective surface having a reflectivity of greater than or equal to 50% (e.g., greater than or equal to 80%) across one or more spectral bands of interest] [e.g., a retroreflective surface (e.g., glass bead or prismatic retroreflective panels, retroreflective tape, a surface painted with retroreflective paint, a surface comprising retroreflective crystals (e.g., a surface to which loose retroreflective spheres or crystals are attached), etc.) (e.g., having a retro-reflective gain of greater than or equal to 10 (e.g., with respect to a diffuse reflector) across one or more spectral bands of interest)].

In certain embodiments, the reflector installment comprises one or more retro-reflective surfaces [e.g., glass bead or prismatic retroreflective panels, retroreflective tape, a surface painted with retroreflective paint, a surface comprising retroreflective crystals (e.g., a surface to which loose retroreflective spheres or crystals are attached), etc.; e.g., having a retro-reflective gain of greater than or approximately equal to 10 (e.g., with respect to a diffuse reflector) (e.g., greater than or approximately equal to 100)].

In certain embodiments, the optical sensor is positioned within 250 meters of a furthest portion of the reflector installment (e.g., within 100 meters of the furthest portion of the reflector installment; e.g., within 50 meters of the furthest portion of the reflector installment; e.g., within 25 meters of the furthest portion of the reflector installment).

In certain embodiments, for each of one or more of the sampled locations along the reflector installment, an angle of incidence and/or exitence from a line of sight from the optical sensor to the sampled location along the reflector installment (e.g., the angle measured between a surface normal and the line of sight) is greater than 1 degree (e.g., greater than 5 degrees; e.g., greater than 10 degrees; e.g., greater than 20 degrees).

In certain embodiments, the reflector installment comprises one or more reflective surfaces, each having a minimum dimension sufficiently large to span, for each of the one or more detectors of the optical sensor, a projection of an individual ifov of the detector onto the reflective surface (e.g., such that an angle subtended by the minimum dimension of the reflective surface from a location of the optical sensor is greater than or approximately equal to the angular extent of the ifov).

In certain embodiments, the method comprises oversampling of the sensor ifov along at least one dimension (e.g., the minimum dimension) of each of the one or more reflective surfaces [e.g., to ensure that the projection of the individual ifov of each detector falls entirely on each reflective surface while scanning the sensor ifov over the reflective surfaces (e.g., wherein the minimum dimension of each reflective surface is comparable to the spot size of projection of the detector ifov at a maximum design operating range)].

In certain embodiments, the reflector installment comprises one or more approximately planar reflective surfaces (e.g., retro-reflective surfaces) [e.g., wherein the approximately planar surfaces are oriented approximately vertically or horizontally (e.g., and/or substantially perpendicular to a plane passing through the optical sensor and above the site to be monitored (e.g., such that the planar reflective surfaces are not tilted extremely up or down, towards the sky or ground)) (e.g., one or more vertical and/or horizontal strip retro-reflectors) (e.g., each spanning an edge of one or more compressor coolers)].

In certain embodiments, the reflector installment comprises a frame comprising (e.g., covered with) a reflective surface (e.g., a retro-reflective surface) [e.g., the frame mounted behind and encircling a boundary of a site to be monitored (e.g., enclosing at least a portion of one or more tanks to be monitored); e.g., wherein the optical sensor is positioned within the site and the frame encircles the site (e.g., to provide for 360 degree coverage)] [e.g., said frame consisting of approximately vertical posts and horizontal crossbars to which retro-reflective surfaces (e.g., retro-reflective panels and/or tapes) are affixed].

In certain embodiments, the reflector installment comprises one or more reflective surfaces (e.g., retro-reflective surfaces) (e.g., curved surfaces) each mounted along at least a portion of an edge of a tank to be monitored (e.g., a plurality of reflective surfaces, each reflective surface mounted along at least a portion of an edge of a tank and/or group of tanks to be monitored).

In certain embodiments, the reflector installment comprises one or more reflective surfaces (e.g., retro-reflective surfaces) mounted along walls of an interior site to be monitored (e.g., under a ceiling, e.g., to monitor gas accumulation).

In certain embodiments, at least a portion of the reflector installment is relocatable.

In certain embodiments, the method comprises performing steps (a) through (d) using two or more optical sensors [e.g., differently located optical sensors, positioned such that their lines-of-sight intersect; e.g., such that each optical sensor detects light from a different direction (e.g., 30 degrees or greater apart; e.g., 60 degrees or more apart; e.g., nearly 90 degrees apart) (e.g., to allow for tomographic sensing to intersect lines of integrated column density in order to localize (e.g., in three dimensions) the emission of the gas)] (e.g., scanning the ifov of each optical sensor over a corresponding portion of the reflector installment) (e.g., to generate two spectral absorption maps, e.g., and using the two spectral absorption maps to localize a location of the emission; e.g., via tomographic sensing).

In certain embodiments, the optical sensor is rotatable [e.g., wherein the method comprises performing steps (a) through (d) to scan a first portion of the reflector installment and monitor a first portion of the site, then rotating the optical sensor and performing steps (a) through (d) to scan a second portion of the reflector installment to monitor a second portion of the site].

In certain embodiments, the one or more detectors comprise one or more spectral detectors, each associated with a particular spectral band of the one or more spectral bands of interest and operable to distinguishably detect (e.g., by virtue of a spectral filter that is transmissive to wavelengths within the particular spectral band and positioned in front of the active area of the detector) light within the particular spectral band.

In certain embodiments, the one or more spectral bands of interest are within the short-wave infrared (SWIR) spectrum (e.g., ranging from about 1.0 to 2.6 microns).

In certain embodiments, the one or more detectors are operable to detect (e.g., are responsive to) light within the short-wave infrared (SWIR) spectrum.

In certain embodiments, each of at least a portion of the one or more spectral bands of interest span an extended spectral feature, comprising a plurality of absorption lines of the one or more compounds of interest [e.g., the portion of the one or more spectral bands of interest having a spectral bandwidth of about 25 nanometers or more, 50 nanometers or more, e.g., about 100 nanometers or more; e.g., about 200 nanometers or more].

In certain embodiments, step (b) comprises detecting, with the one or more detectors of the optical sensor, reflected ambient light having been reflected from a plurality of additional sampled locations and captured within the ifov of the optical sensor, the plurality of additional sampled locations within a target region comprising the reflector installment, but not on the reflector installment (e.g., the reflected ambient light having been reflected by background materials), and the data corresponding to the detected light received and/or accessed at step (c) comprises data corresponding to detected light having been reflected from (i) the sampled image locations on the reflector installment, as well as (ii) the additional sampled locations not on the reflector installment [e.g., such that the spectral absorption map comprises pixels representing absorption levels associated with sampled locations both on and off the reflector installment (e.g., both image pixels formed based on light received from tailored reflector installations as well as image pixels formed based on light received from reflection of background materials without such tailored reflector installations] [e.g., such that hydrocarbon emissions may be detected via the absorption map in a variety of fashions, such as, e.g., a single hydrocarbon gas plume detected partially against a reflector installment and partially against background materials, e.g., separate hydrocarbon gas plumes (e.g., or parts thereof spanning multiple pixels) are detected against reflector installment and background materials, and/or e.g., hydrocarbon gas plumes detected against the background materials (e.g., although tailored reflectors and background materials are being scanned)].

In certain embodiments, the method further comprises using the data corresponding to the detected light (e.g., from either the tailored reflector installments or from both the tailored reflector installments and from background materials) to quantify the emission of the gas from within the site [e.g., using the data (e.g., to determine a measure of column density of the gas) in combination with a measure of wind speed and direction (e.g., crossing the optical curtain) and/or a buoyancy of the gas; e.g., to determine at least one of a total volume of the emission of the gas, a total mass of the emission of the gas, a mass flux of the emission of the gas].

In certain embodiments, the method comprises using the data corresponding to the detected light to quantify a mass flux of the emission of the gas from within the site (e.g., from within each of at least a portion of one or more assets within the site).

In certain embodiments, the method comprises using the data corresponding to the detected light to quantify a mass flux of gas passing between a first sector and a second, neighboring (e.g., sharing a boundary with the first sector), sector (e.g., two sub-divisions, e.g., a hazardous sector and a non-hazardous sector) of the site [e.g., wherein lines of site from at least a portion of the sampled locations, to the optical sensor form a surface that sub-divides the site into the first and second sector, and or more sectors].

In another aspect, the invention is directed to a system for generating a spectral absorption map for detecting emission of gas comprising one or more compounds of interest [e.g., hydrocarbon compounds (e.g., methane, ethane, propane, butane, pentane, hexane, octane, ethylene, and other hydrocarbons); e.g., other compounds such as carbon dioxide and ammonia], the system comprising: (a) a reflector installment mounted about a site to be monitored; (b) an optical sensor positioned in proximity to the reflector installment (e.g., within 250 meters of a furthest portion of the reflector installment; e.g., within 100 meters of a furthest portion of the reflector installment; e.g., within 50 meters of a furthest portion of the reflector installment; e.g., within 25 meters of a furthest portion of the reflector installment) comprising one or more detectors, wherein: the one or more detectors are aligned and operable to detect light within one or more spectral bands of interest [e.g., wherein the one or more spectral bands of interest are within the short-wave infrared (SWIR) spectrum (e.g., ranging from about 1.0 to 2.6 microns); e.g., the one or more spectral bands of interest lying within the visible through near-infrared spectrum (e.g., ranging from about 0.4 to 1.0 microns)], at least a portion of said spectral bands of interest overlapping with one or more spectral features [e.g., spectral absorption due to (e.g., and indicative of presence of)] associated with the one or more compounds of interest, and the one or more detectors are aligned to detect light reflected from a plurality of sampled locations on the reflector installment [e.g., at least a portion of the plurality of sampled locations spaced sufficiently close (e.g., no greater than 1 meter apart; e.g., no greater than 50 cm apart; e.g., no greater than 25 cm apart; e.g., no greater than 10 cm apart; e.g., no greater than 1 cm apart) so as to provide a spatial resolution and/or angular resolution (e.g., between neighboring lines-of-sight from sampled locations to the optical sensor) (e.g., such that an angle between adjacent lines of sight from the optical sensor to neighboring sampled locations is sufficiently small (e.g., no greater than 0.1 radians; e.g., no greater than 0.05 radians; e.g., no greater than 0.01 radians; e.g., no greater than 0.001 radians; e.g., no greater than $10^{-4}$ radians; e.g., no greater than $5 \times 10^{-5}$ radians)) commensurate with (e.g., sufficiently fine to detect; e.g., smaller than) a characteristic size of the emission of the gas (e.g., of a typical cloud or plume)] and captured within an instantaneous field of view (ifov) of the optical sensor {e.g., thereby detecting light travelling along lines-of-sight from each sampled location to the optical sensor and/or an illumination source (e.g., co-located with the optical sensor), to form an optical curtain (e.g., a surface substantially confined to a 2D plane; e.g., a surface not confined to a 2D plane and varying in 3D space) at least partially enveloping, and/or forming at least a partial boundary of, at least a portion of the site [e.g., such that the optical curtain partially encloses a volume (e.g., comprising one or more assets being monitored), and/or forms an at least partial boundary of a volume (e.g., comprising one or more assets being monitored), from within which the emission of the gas can be detected; e.g., whereby gas emitted from with the volume crosses optical curtain (formed by the lines-of-sight from each sampled location to the optical sensor), resulting in detectable absorption (e.g., within at least a portion of the one or more spectral bands of interest) of light reflected from locations along the reflector installment as the light travels to the optical sensor]}; (c) a processor of a computing device; and (d) a memory having instructions stored thereon, wherein the instructions, when executed by one processor, cause the processor to: receive and/or access, data corresponding to the detected light from each of the plurality of sampled locations (e.g., wherein the plurality of sampled locations along the reflector installment define surface corresponding to a surface of the reflector installment); and determine, for each of at least a portion of the plurality of sampled locations, an absorption level associated with (e.g., due to) at least one of the one or more spectral features using the detected light, thereby generating a spectral absorption map comprising a plurality of absorption levels, each associated with a particular sampled location and spectral feature.

In certain embodiments, the instructions further cause the processor to detect (e.g., automatically) the emission of the gas from with the site to be monitored using the generated spectral absorption map.

In certain embodiments, the instructions cause the processor to detect the emission of the gas by automatically analyzing the absorption levels of the spectral absorption map [e.g., by comparing at least a portion of the absorption levels (e.g., associated with a single spectral feature; e.g., associated with multiple spectral features) with one or more threshold values; e.g., by identifying regions of pixels (each pixel corresponding to a particular sampled location) wherein a measure of an absorption level in the region (e.g., a minimum, a median, a mean, etc.) is above a particular threshold value].

In certain embodiments, the instructions cause the processor to use the absorption levels of the spectral absorption map to determine, for each of at least a portion of the plurality of sampled locations, a column density [e.g., a value representing, for a particular sampled location, a number of gas molecules in between (e.g., along a line of sight) the optical sensor and the particular sampled location] of one or more of the compounds of interest [e.g., thereby creating an image representing gas concentration across a region of space in between the optical sensor and the reflector installment, the image comprising a plurality of pixels, each corresponding to a particular sampled location and having a value representing the column density determined for the particular sampled location].

In certain embodiments, the system comprises a scanning illuminator aligned and operable to emit and direct a structured illumination beam (e.g., wherein the scanning illuminator is co-located with the optical sensor) towards the reflector installment and scan the structured illumination beam across at least a portion of the reflector installment, thereby illuminating the plurality of sampled locations (e.g., wherein the beam of illumination illuminates one or more of the sampled locations at a time as it is scanned) (e.g., such that the detected light is light from the illumination source that is reflected back to the optical sensor by the reflector installment).

In certain embodiments, the scanning illuminator is operable to scan the beam of illumination in a continuous fashion across a portion of a target region comprising the reflector installment, thereby illuminating the plurality of sampled locations along the reflector installment as well as other locations within the target region, not necessarily on the reflector installment.

In certain embodiments, the scanning illuminator is a broadband source, such that the beam of illumination has a spectral bandwidth spanning a plurality of spectral features of [e.g., spectral absorption due to (e.g., and indicative of presence of)] the one or more compounds of interest [e.g., wherein the beam of illumination has a spectral bandwidth of at least 200 nanometer (e.g., at least 500 nanometers; e.g., at least 1000 nanometers)]. In certain embodiments, the scanning illuminator comprises a broadband short-wave infrared (SWIR) source [e.g., having a bandwidth of approximately 500 nanometer or more in the SWIR region (e.g., ranging from about 1.0 microns to 2.6 microns)].

In certain embodiments, the system comprises an optical sensor scanner operable to scan the ifov of the optical sensor across the portion of the reflector installment in a synchronized fashion with the beam of illumination (e.g., so as to maintain overlap between illuminated locations on the reflector installment and the ifov of the sensor) and so as to detect, with the one or more detectors, within the one or more spectral bands of interest, the light reflected from each of the sampled locations along the reflector installment as the ifov is scanned [e.g., wherein the ifov captures light reflected from one or more of the sampled locations at time as it is scanned (e.g., wherein the ifov captures light reflected from a single sampled location at a time; e.g., wherein the ifov captures light from a plurality of sampled locations at a time (e.g., the one or more detectors comprising a plurality of pixels for sampling a plurality of spatial locations at a time))].

In certain embodiments, the scanning illuminator is co-located with (e.g., and mechanically coupled to) the optical sensor [(e.g., both located in close proximity to each other; e.g., both using a same rotatable mirror to receive and/or send light; e.g., mounted together on a rotation stage or a pan-tilt stage)], such that both the beam of illumination and the ifov are scanned in tandem.

In certain embodiments, the ifov and the beam of illumination are scanned using mechanically coupled mirrors.

In certain embodiments, the system comprises an optical sensor scanner operable to scan the ifov of the optical sensor across at least a portion of the reflector installment, so as to detect, with the one or more detectors, within the one or more spectral bands of interest, light reflected from each of the sampled locations along the reflector installment as the ifov is scanned [e.g., wherein the ifov captures light reflected from one or more of the sampled locations at time as it is scanned (e.g., wherein the ifov captures light reflected from a single sampled location at a time; e.g., wherein the ifov captures light from a plurality of sampled locations at a time (e.g., the one or more detectors comprising a plurality of pixels for sampling a plurality of spatial locations at a time)) e.g., wherein ambient light (e.g., sunlight) is sufficient to generate detectable signal (e.g., and no dedicated illumination source is needed)].

In certain embodiments, the reflector installment comprises one or more continuous reflective sections of sufficient size to span a plurality of the sampled locations [e.g., two or more of the sampled locations are on a same, continuous, reflective surface; e.g., each continuous reflective section is at least twice (e.g., at least five times; e.g., at least ten times; e.g., at least 20 times) as large as an individual ifov of each of the one or more detectors along at least one dimension].

In certain embodiments, the reflector installment comprises one or more continuous reflective sections each comprising a plurality of individual retro-reflective elements (e.g., the reflection sections are panels comprised over many tiny retro-reflectors that cover extended strips or areas, as opposed to discreet corner cube reflectors that occupy points not areas or strips).

In certain embodiments, the one or more detectors comprise an array detector comprising a plurality of pixels and aligned to image a spatial region comprising two or more of the sampled locations (e.g., a two-dimensional focal plane array detector aligned to image a two-dimensional spatial region; e.g., a two-dimensional focal plane array detector aligned to image a one-dimensional spatial region; e.g., a one-dimensional array detector).

In certain embodiments, the one or more detectors are aligned to image a single spatial location at a time [e.g., a point detector comprising a single pixel; e.g., an array detection (e.g., a quadrant detector) comprising a plurality of pixels aligned to detect light from a substantially same spatial location (e.g., each pixel detecting light from within a different spectral band of interest)].

In certain embodiments, the reflector installment comprises one or more reflective sections mounted in proximity to (e.g., behind with respect to a location of the optical sensor; e.g., at least partially encircling; e.g., encircling), and/or mounted on, one or more assets [(e.g., one or more well pads; e.g., one or more compressor coolers; e.g., one or more fracking rigs; one or more liquid natural gas engines (e.g., of a ship); e.g., one or more floating liquid natural gas platforms; e.g., one or more liquid natural gas tankers; e.g., liquid natural gas loading/unloading equipment)] within the site (e.g., wherein the site is an interior site; e.g., wherein the site is an off-shore site; e.g., wherein the site is a liquid natural gas loading site; e.g., wherein the site is a temporary repair operations site; e.g., wherein the site is a plant undergoing commissioning and/or turnaround).

In certain embodiments, the reflector installment comprises one or more reflective sections, each comprising a reflective surface [e.g., the reflective surface having a reflectivity of greater than or equal to 50% (e.g., greater than or equal to 80%) across one or more spectral bands of interest] [e.g., a retroreflective surface (e.g., glass bead or prismatic retroreflective panels, retroreflective tape, a surface painted with retroreflective paint, a surface comprising retroreflective crystals (e.g., a surface to which loose retroreflective spheres or crystals are attached), etc.) (e.g., having a retroreflective gain of greater than or equal to 10 (e.g., with respect to a diffuse reflector) across one or more spectral bands of interest)].

In certain embodiments, the reflector installment comprises one or more retroreflective surfaces [e.g., glass bead or prismatic retroreflective panels, retroreflective tape, a surface painted with retroreflective paint, a surface comprising retroreflective crystals (e.g., a surface to which loose retroreflective spheres or crystals are attached), etc.; e.g., having a retroreflective gain of greater than or approximately equal to 10 (e.g., with respect to a diffuse reflector) (e.g., greater than or approximately equal to 100)].

In certain embodiments, the optical sensor is positioned within 250 meters of a furthest portion of the reflector installment (e.g., within 100 meters of the furthest portion of the reflector installment; e.g., within 50 meters of the furthest portion of the reflector installment; e.g., within 25 meters of the furthest portion of the reflector installment).

In certain embodiments, for each of one or more of the sampled locations along the reflector installment, an angle of incidence and/or exitence from a line of sight from the optical sensor to the sampled location along the reflector installment (e.g., the angle measured between a surface normal and the line of sight) is greater than 1 degree (e.g., greater than 5 degrees; e.g., greater than 10 degrees; e.g., greater than 20 degrees).

In certain embodiments, the reflector installment comprises one or more reflective surfaces, each having a minimum dimension sufficiently large to span, for each of the one or more detectors of the optical sensor, a projection of an individual ifov of the detector onto the reflective surface (e.g., such that an angle subtended by the minimum dimension of the reflective surface from a location of the optical sensor is greater than or approximately equal to the angular extent of the ifov).

In certain embodiments, the system comprises an optical sensor scanner operable to scan the sensor ifov in a manner that over-samples along at least one dimension (e.g., the minimum dimension) of each of the one or more reflective surfaces [e.g., to ensure that the projection of the individual ifov of each detector falls entirely on each reflective surface while scanning the sensor ifov over the reflective surfaces (e.g., wherein the minimum dimension of each reflective surface is comparable to the spot size of projection of the detector ifov at a maximum design operating range)].

In certain embodiments, the reflector installment comprises one or more approximately planar reflective surfaces (e.g., retroreflective surfaces) [e.g., wherein the approximately planar surfaces are oriented approximately vertically or horizontally (e.g., and substantially perpendicular to a plane passing through the optical sensor and above the site to be monitored (e.g., such that the planar reflective surfaces are not tilted extremely up or down, towards the sky or ground)) (e.g., one or more vertical and/or horizontal line retro-reflectors) (e.g., each spanning an edge of one or more compressor coolers)].

In certain embodiments, the reflector installment comprises a frame comprising (e.g., covered with) a reflective surface (e.g., a retroreflective surface) [e.g., mounted behind and encircling a boundary of a site to be monitored (e.g., enclosing at least a portion one or more tanks to be monitored); e.g., wherein the optical sensor is positioned within the site and the frame encircles the site (e.g., to provide for 360 degree coverage)] [e.g., said frame consisting of approximately vertical posts and horizontal crossbars to which retroreflective surfaces (e.g., retroreflective panels and/or tapes) are affixed].

In certain embodiments, the reflector installment comprises one or more reflective surfaces (e.g., retroreflective surfaces) (e.g., curved surfaces) each mounted along at least a portion of an edge of a tank to be monitored (e.g., a plurality of reflective surfaces, each reflective surface mounted along at least a portion of an edge of a tank and/or group of tanks to be monitored).

In certain embodiments, the reflector installment comprises one or more reflective surfaces (e.g., retroreflective surfaces) mounted along walls of an interior site to be monitored (e.g., under a ceiling, e.g., to monitor gas accumulation).

In certain embodiments, at least a portion of the reflector installment is relocatable.

In certain embodiments, the system comprises two or more optical sensors [e.g., differently located optical sensors, positioned such that their lines of sight intersect; e.g., such that each optical sensor detects light from a different direction (e.g., 30 degrees or greater apart; e.g., 60 degrees or more apart; e.g., nearly 90 degrees apart) (e.g., to allow for tomographic sensing to intersect lines of integrated column density in order to localize (e.g., in three dimensions) the emission of the gas)], and two optical sensor scanners, each associated with one of the optical sensors and operable to scan the ifov of the associated optical sensor over a corresponding portion of the reflector installment (e.g., and wherein the instructions cause the processor to generate two spectral absorption maps, e.g., and use the two spectral absorption maps to localize a location of the emission; e.g., via tomographic sensing).

In certain embodiments, the optical sensor and optical sensor scanner are rotatable [e.g., mounted on a rotatable stage (e.g., so that they can scan a first portion of the reflector installment and monitor a first portion of the site, then be rotated to scan a second portion of the reflector installment to monitor a second portion of the site)].

In certain embodiments, the one or more detectors comprise one or more spectral detectors, each associated with a particular spectral band of the one or more spectral bands of interest and operable to distinguishably detect (e.g., by virtue of a spectral filter that is transmissive to wavelengths within the particular spectral band and positioned in front of the active area of the detector) light within the particular spectral band.

In certain embodiments, the one or more spectral bands of interest are within the short-wave infrared (SWIR) spectrum (e.g., ranging from about 1.0 to 2.6 microns).

In certain embodiments, the one or more detectors are operable to detect (e.g., are responsive to) light within the short-wave infrared (SWIR) spectrum In certain embodiments, each of at least a portion of the one or more spectral bands of interest span an extended spectral feature, comprising a plurality of absorption lines of the one or more compounds of interest [e.g., the portion of the one or more spectral bands of interest having a spectral bandwidth of about 25 nanometers or more, e.g., about 50 nanometers or more, e.g., about 100 nanometers or more; e.g., about 200 nanometers or more].

In certain embodiments, the one or more detectors are aligned and operable to detect reflected ambient light (e.g., sunlight) having been reflected from a plurality of additional sample locations and captured within the ifov of the optical sensor, the plurality of additional sample locations within the target region, but not on the reflector installment (e.g., the reflected ambient light having been reflected by background materials) and the data corresponding to the detected light further comprises data corresponding to the reflected ambient light [e.g., such that the spectral absorption map comprises pixels representing absorption levels associated with sampled locations both on and off the reflector installment (e.g., both image pixels formed based on light received from tailored reflector installations as well as image pixels formed based on light received from reflection of background materials without such tailored reflector installations] [e.g., such that hydrocarbon emissions may be detected via the absorption map in a variety of fashions, such as, e.g., a single hydrocarbon gas plume detected partially against a reflector installment and partially against background materials, e.g., separate hydrocarbon gas plumes (e.g., or parts thereof spanning multiple pixels) are detected against reflector installment and background materials, and/ or e.g., hydrocarbon gas plumes detected against the background materials (e.g., although tailored reflectors and background materials are being scanned)].

In certain embodiments, the instructions cause the processor to use the data corresponding to the detected light (e.g., from either the tailored reflector installments or from both the tailored reflector installments and from background materials) to quantify the emission of the gas from within the site [e.g., to use the data e.g., to determine a measure of column density of the gas) in combination with a measure of wind speed (e.g., crossing the optical curtain) and/or a buoyancy of the gas; e.g., to determine at least one of a total volume of the emission of the gas, a total mass of the emission of the gas, a mass flux of the emission of the gas].

In certain embodiments, the instructions cause the processor to use the data corresponding to the detected light to quantify a mass flux of the emission of the gas from within the site (e.g., from within each of at least a portion of one or more assets within the site).

In certain embodiments, the instructions cause the processor to use the data corresponding to the detected light to quantify a mass flux of gas passing between a first sector and a second, neighboring (e.g., sharing a boundary with the first sector), sector (e.g., two sub-divisions, e.g., a hazardous sector and a non-hazardous sector) of the site [e.g., wherein lines of site from at least a portion of the sampled locations, to the optical sensor form a surface that sub-divides the site into the first and second sector, and or more sectors].

In another aspect, the invention is directed to a reflector installment comprising one or more retroreflective sections (e.g., one or more retro-reflector panels and/or surfaces covered in retroreflective material (e.g., tape)), each mounted along a portion of an edge of an asset (e.g., a tank comprising one or more hydrocarbon compounds) to be monitored for gas emission, wherein: each retroreflective section is oriented substantially in a vertical direction, extending upwards with respect to a top of the asset to which it is mounted (e.g., and behind the asset with respect to an observation location where an optical sensor is or may be positioned); and a surface of each retroreflective section that is oriented inwards from the edge of the asset has a retroreflective gain greater than about 10 (e.g., greater than about 20; e.g., greater than about 50; e.g., greater than about 100) (e.g., in comparison with respect to a diffuse reflector) across one or more spectral bands of interest (e.g., across wavelength ranging from 1.0 to 2.6 microns).

In certain embodiments, each retroreflective section extends along at least about 10% of a perimeter (e.g., along at least 20% of the perimeter; e.g., along at least 50% of the perimeter) of the asset (e.g., a top of a tank).

In another aspect, the invention is directed to a reflector installment comprising a frame comprising (e.g., covered with) a retroreflective surface having a retroreflective gain greater than about 10 (e.g., greater than about 20; e.g., greater than about 50; e.g., greater than about 100) (e.g., in comparison with respect to a diffuse reflector) across one or more spectral bands of interest (e.g., across wavelength ranging from 1.0 to 2.6 microns), wherein said frame is mounted behind and encircling a boundary of a site to be monitored [e.g., enclosing at least a portion one or more assets to be monitored; e.g., wherein the frame encircles an optical sensor is positioned within the site (e.g., to provide for 360 degree coverage)] [e.g., said frame consisting of approximately vertical posts and horizontal crossbars to which retroreflective surfaces (e.g., retroreflective panels and/or tapes) are affixed].

In another aspect, the invention is directed to a reflector installment comprising one or more approximately planar retroreflective sections, wherein: each approximately planar retroreflective section is oriented approximately vertically or horizontally (e.g., and substantially perpendicular to a plane passing through the optical sensor and above the site to be monitored (e.g., such that the planar surfaces are not tilted extremely up or down, towards the sky or ground)) (e.g., is a vertical or horizontal line retro-reflectors); each approximately planar retroreflective section spans an edge of one or more assets (e.g., one or more compressor coolers); and a surface of each approximately planar retroreflective section that is oriented inwards from an edge of the asset has a retroreflective gain greater than about 10 (e.g., greater than about 20; e.g., greater than about 50; e.g., greater than about 100) (e.g., in comparison with respect to a diffuse reflector) across one or more spectral bands of interest (e.g., across wavelength ranging from 1.0 to 2.6 microns).

In another aspect, the invention is directed to a method of generating a spectral absorption map for detecting emission of gas comprising one or more compounds of interest [e.g., hydrocarbon compounds (e.g., methane, ethane, propane, butane, pentane, hexane, octane, ethylene, and other hydrocarbons); e.g., other compounds such as carbon dioxide and ammonia], the method comprising: (a) positioning an instantaneous field of view (ifov) of an optical sensor toward a reflector installment mounted about a site to be monitored and within a target region; (b) directing a beam of illumination from an illumination source (e.g., an illumination source co-located with the optical sensor) and toward the reflector installment (e.g., wherein the beam of illumination illuminates one or more of the sampled locations at a time as it is scanned) (e.g., such that the detected light is light from the illumination source that is reflected back to the optical sensor by the reflector installment); (c) scanning the beam of illumination across at least a portion of the reflector installment, thereby illuminating a plurality of sample locations on the reflector installment (e.g., wherein the beam of illumination illuminates one or more of the sampled locations at a time as it is scanned); (d) detecting (e.g., in a spectrally selective manner), with one or more detectors of the optical sensor, light within one or more spectral bands of interest [e.g., the one or more spectral bands of interest lying within the short-wave infrared (SWIR) spectrum (e.g., ranging from about 1.0 to 2.6 microns); e.g., the one or more spectral bands of interest lying within the visible through near-infrared spectrum (e.g., ranging from about 0.4 to 1.0 microns)], at least a portion of which overlap with one or more spectral features associated with [e.g., spectral absorption due to (e.g., and indicative of presence of)] the one or more compounds of interest, wherein the detected light comprises: (i) reflected illumination light corresponding to light from the beam of illumination having been reflected from the plurality of sample locations on the reflector installment and captured within the ifov of the optical sensor {e.g., thereby detecting light travelling along lines-of-sight from each sampled location to the optical sensor and illumination source (e.g., co-located with the optical sensor), e.g. to form an optical curtain (e.g., a surface substantially confined to a 2D plane; e.g., a surface not confined to a 2D plane and varying in 3D space) at least partially enveloping, and/or forming at least a partial boundary of, at least a portion of the site, or creating a surface that divides a site into multiple sectors [e.g., such that the optical curtain partially encloses a volume (e.g., comprising one or more assets being monitored), and/or forms an at least partial boundary of a volume (e.g., comprising one or more assets being monitored), from within which the emission of the gas can be detected; e.g., whereby gas emitted from within the volume crosses the optical curtain (formed by the lines-of-sight from each sampled location to the optical sensor), e.g., whereby gas emitted from one sector crosses the optical curtain into the other sector, resulting in detectable absorption (e.g., within at least a portion of the one or more spectral bands of interest) of light reflected from locations along the reflector installment as the light travels back to the optical sensor]}, and (ii) reflected ambient light having been reflected from a plurality of additional sample locations and captured within the ifov of the optical sensor, the plurality of additional sample locations lying within the target region, but not on the reflector installment (e.g., thereby detecting light traveling along additional lines-of-sight from each additional sampled location to the optical sensor); (e) receiving and/or accessing, by a processor of a computing device, data corresponding to the detected light, comprising both (i) the reflected illumination light and (ii) the reflected ambient light (e.g., wherein the plurality of sampled locations along the reflector installment define a surface corresponding to a segment of the reflector installment and the plurality of additional sampled locations define surfaces within a boundary of the segment of the reflector installment and/or surfaces outside (e.g., nearby) the reflector installment); and (f) determining, by the processor, for each of (i) at least a portion of the plurality of sampled locations on the reflector installment and (ii) at least a portion of the plurality of additional sample locations, an absorption level associated with (e.g., due to) at least one of the one or more spectral features using the detected light, thereby generating a spectral absorption map comprising a plurality of absorption levels, each associated with a: (i) a particular sampled location on the reflector installment or a particular additional sampled location and (ii) a spectral feature.

In certain embodiments, the method comprises (g) detecting [e.g., by the processor (e.g., automatically)] the emission of the gas from within the site to be monitored using the generated spectral absorption map.

In certain embodiments, step (g) comprises detecting the emission of the gas by automatically analyzing, by the processor, the absorption levels of the spectral absorption map [e.g., by comparing at least a portion of the absorption levels (e.g., associated with a single spectral feature; e.g., associated with multiple spectral features) with one or more threshold values; e.g., by identifying regions of pixels (each pixel corresponding to a particular sampled location) wherein a measure of an absorption level in the region (e.g., a minimum, a median, a mean, etc.) is above a particular threshold value].

In certain embodiments, the method comprises using the absorption levels of the spectral absorption map to determine, by the processor, for each of at least a portion of the plurality of sampled locations, a column density [e.g., a value representing, for a particular sampled location, a number of gas molecules in between (e.g., along a line of sight) the optical sensor and the particular sampled location] of one or more of the compounds of interest [e.g., thereby creating an image representing gas concentration across a region of space in between the optical sensor and the reflector installment, the image comprising a plurality of pixels, each corresponding to a particular sampled location and having a value representing the column density determined for the particular sampled location In certain embodiments, step (g) comprises comparing (i) a first set of one or more absorption levels associated with one or more specific sampled locations on the reflector installment with (ii) a second set of one or more absorption levels associated with one or more specific additional sampled locations in a vicinity of the one or more specific sampled locations on the reflector installment to identify the absorption levels of the first set and/or the second set as indicative of gas emission (e.g., a true positive) or noise (e.g., a false positive) (e.g., based on expectation that a gas emission signal associated with sampled locations on the reflector installment will have a correlated signal associated with nearby additional sampled locations off of the reflector installment, and vice versa).

In certain embodiments, the method comprises: using a first set of one or more absorption levels associated with one or more specific sampled locations on the reflector installment to identify, within the absorption map, an initial portion of a gas plume boundary; and using the initial portion of the gas plume boundary to identify, within the absorption map, one or more absorption levels associated with one or more specific additional sampled locations as indicative of gas emission and combining them with the initial portion of identified initial portion of the gas plume boundary to identify a region (e.g., a 2D region) within the absorption map as corresponding to the gas plume (e.g., to complete the identification of the gas plume boundary; e.g., to generate a 2D representation of a detected gas plume).

In certain embodiments, the method comprises using the identified region corresponding to the gas plume to determine a location and/or leak rate of a gas leak from which the gas plume originates (e.g., by combining shape information from the identified region with wind speed and/or direction measurements; e.g., by using a 2D shape of the identified region as an input to a fluid dynamics model).

In another aspect, the invention is directed to a system for generating a spectral absorption map for detecting emission of gas comprising one or more compounds of interest [e.g., hydrocarbon compounds (e.g., methane, ethane, propane, butane, pentane, hexane, octane, ethylene, and other hydrocarbons); e.g., other compounds such as carbon dioxide and ammonia], the system comprising: (a) a reflector installment mounted about a site to be monitored within a target region; (b) a scanning illuminator positioned in proximity to the reflector installment (e.g., with 250 meters of a furthest portion of the reflector installment; e.g., within 100 meters of a furthest portion of the reflector installment; e.g., within 50 meters of a furthest portion of the reflector installment; e.g., within 25 meters of a furthest portion of the reflector installment) aligned and operable to emit and direct a structured illumination beam towards the reflector installment and scan the structured illumination beam across at least a portion of the reflector installment, thereby illuminating a plurality of sampled locations (e.g., wherein the beam of illumination illuminates one or more of the sampled locations at a time as it is scanned); (c) an optical sensor positioned in proximity to the reflector installment (e.g., wherein the scanning illuminator is co-located with the optical sensor) comprising one or more detectors, wherein: the one or more detectors are aligned and operable to detect light within one or more spectral bands of interest [e.g., wherein the one or more spectral bands of interest are within the short-wave infrared (SWIR) spectrum (e.g., ranging from about 1.0 to 2.6 microns); e.g., the one or more spectral bands of interest lying within the visible through near-infrared spectrum (e.g., ranging from about 0.4 to 1.0 microns)], at least a portion of said spectral bands of interest overlapping with one or more spectral features [e.g., spectral absorption due to (e.g., and indicative of presence of)] associated with the one or more compounds of interest, and the one or more detectors are aligned to detect: (i) reflected illumination light corresponding to light from the beam of illumination having been reflected from the plurality of sample locations on the reflector installment and captured within the ifov of the optical sensor {e.g., thereby detecting light travelling along lines-of-sight from each sampled location to the optical sensor and/or an illumination source (e.g., co-located with the optical sensor), to form an optical curtain (e.g., a surface substantially confined to a 2D plane; e.g., a surface not confined to a 2D plane and varying in 3D space) at least partially enveloping, and/or forming at least a partial boundary of, at least a portion of the site [e.g., such that the optical curtain partially encloses a volume (e.g., comprising one or more assets being monitored), and/or forms an at least partial boundary of a volume (e.g., comprising one or more assets being monitored), from within which the emission of the gas can be detected; e.g., whereby gas emitted from with the volume crosses optical curtain (formed by the lines-of-sight from each sampled location to the optical sensor), resulting in detectable absorption (e.g., within at least a portion of the one or more spectral bands of interest) of light reflected from locations along the reflector installment as the light travels to the optical sensor]}, and (ii) reflected ambient light having been reflected from a plurality of additional sample locations and captured within the ifov of the optical sensor, the plurality of additional sample locations within the target region, but not on the reflector installment (d) a processor of a computing device; and (e) a memory having instructions stored thereon, wherein the instructions, when executed by one processor, cause the processor to: receive and/or access data corresponding to the detected light, comprising both (i) the reflected illumination light and (ii) the reflected ambient light; and determine, for each of (i) at least a portion of the plurality of sampled locations on the reflector installment and (ii) at least a portion of the plurality of additional sample locations, an absorption level associated with (e.g., due to) at least one of the one or more spectral features using the detected light, thereby generating a spectral absorption map comprising a plurality of absorption levels, each associated with: (i) a particular sampled location on the reflector installment or a particular additional sampled location and (ii) a spectral feature.

In certain embodiments, the instructions cause the processor to detect (e.g., automatically) the emission of the gas from within the site to be monitored using the generated spectral absorption map.

In certain embodiments, the instructions cause the processor to detect the emission of the gas by automatically analyzing the absorption levels of the spectral absorption map [e.g., by comparing at least a portion of the absorption levels (e.g., associated with a single spectral feature; e.g., associated with multiple spectral features) with one or more threshold values; e.g., by identifying regions of pixels (each pixel corresponding to a particular sampled location) wherein a measure of an absorption level in the region (e.g., a minimum, a median, a mean, etc.) is above a particular threshold value].

In certain embodiments, the instructions cause the processor to use the absorption levels of the spectral absorption map to determine, for each of at least a portion of the plurality of sampled locations, a column density [e.g., a value representing, for a particular sampled location, a number of gas molecules in between (e.g., along a line of sight) the optical sensor and the particular sampled location] of one or more of the compounds of interest [e.g., thereby creating an image representing gas concentration across a region of space in between the optical sensor and the reflector installment, the image comprising a plurality of pixels, each corresponding to a particular sampled location and having a value representing the column density determined for the particular sampled location].

In certain embodiments, the instructions cause the processor to detect the emission of the gas by comparing (i) a first set of one or more absorption levels associated with one or more specific sampled locations on the reflector installment with (ii) a second set of one or more absorption levels associated with one or more specific additional sampled locations in a vicinity of the one or more specific sampled locations on the reflector installment to identify the absorption levels of the first set and/or the second set as indicative of gas emission (e.g., a true positive) or noise (e.g., a false positive) (e.g., based on expectation that a gas emission signal associated with sampled locations on the reflector installment will have a correlated signal associated with nearby additional sampled locations off of the reflector installment, and vice versa).

In certain embodiments, the instructions cause the processor to: use a first set of one or more absorption levels associated with one or more specific sampled locations on the reflector installment to identify, within the absorption map, an initial portion of a gas plume boundary; and use the initial portion of the gas plume boundary to identify, within the absorption map, one or more absorption levels associated with one or more specific additional sampled locations as indicative of gas emission and combining them with the initial portion of identified initial portion of the gas plume boundary to identify a region (e.g., a 2D region) within the absorption map as corresponding to the gas plume (e.g., to complete the identification of the gas plume boundary; e.g., to generate a 2D representation of a detected gas plume).

In certain embodiments, the instructions cause the processor to use the identified region corresponding to the gas plume to determine a location and/or leak rate of a gas leak from which the gas plume originates (e.g., by combining shape information from the identified region with wind speed and/or direction measurements; e.g., by using a 2D shape of the identified region as an input to a fluid dynamics model).

Features of embodiments described with respect to one aspect of the invention may be applied with respect to another aspect of the invention.

BRIEF DESCRIPTIONS OF THE DRAWINGS

The foregoing and other objects, aspects, features, and advantages of the present disclosure will become more apparent and better understood by referring to the following description taken in conjunction with the accompanying drawings, in which.

Figure 1A:
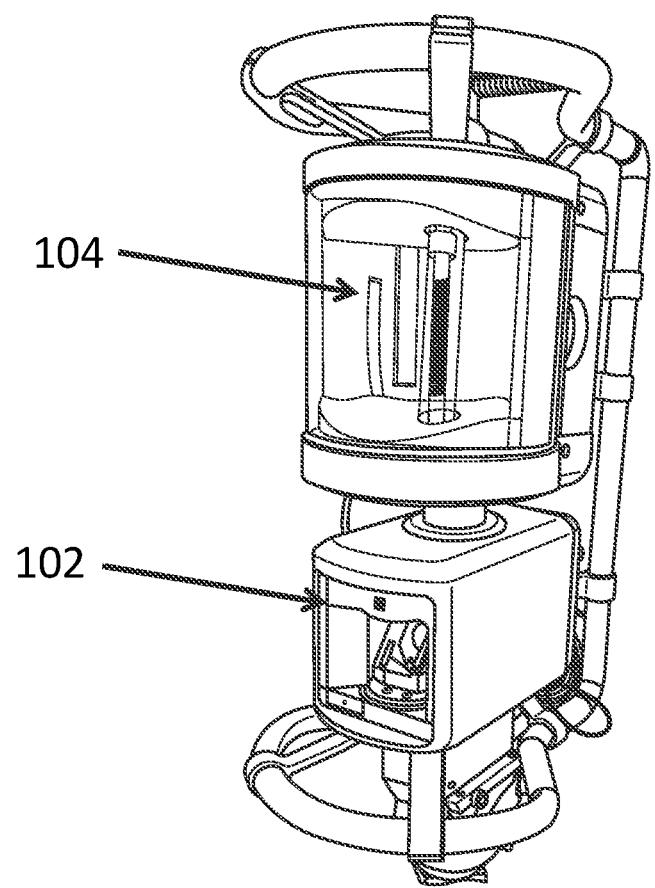
FIG. 1A is an image of a prototype multispectral short wave infrared (SWIR) scanning optical gas sensor and illuminator where the sensor and the illuminator are scanned separately, mounted in a protective cage, according to an illustrative embodiment.
Figure 1E:
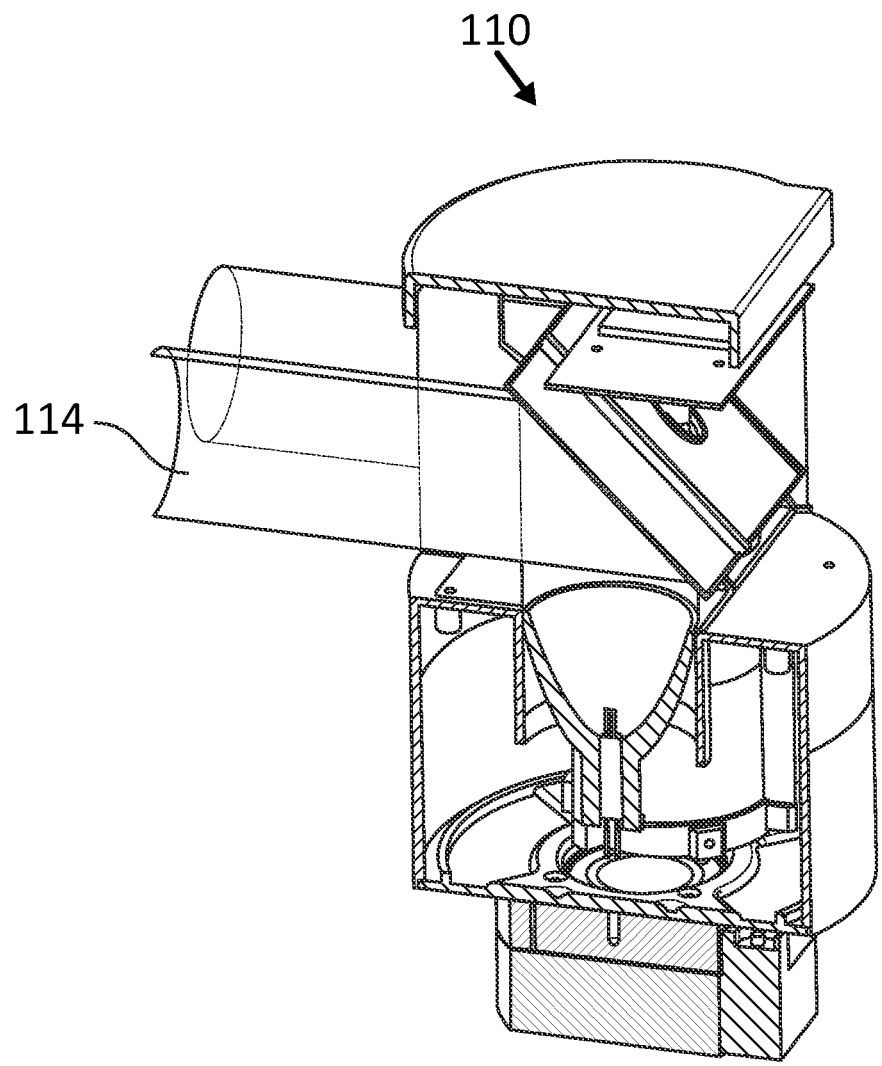
FIG. 1B is a schematic showing a front views of a prototype multispectral short wave infrared (SWIR) scanning optical gas sensor and illuminator arranged as an optical sensor scanner and mounted on a rotatable stage, according to an illustrative embodiment.
Figure 2A:
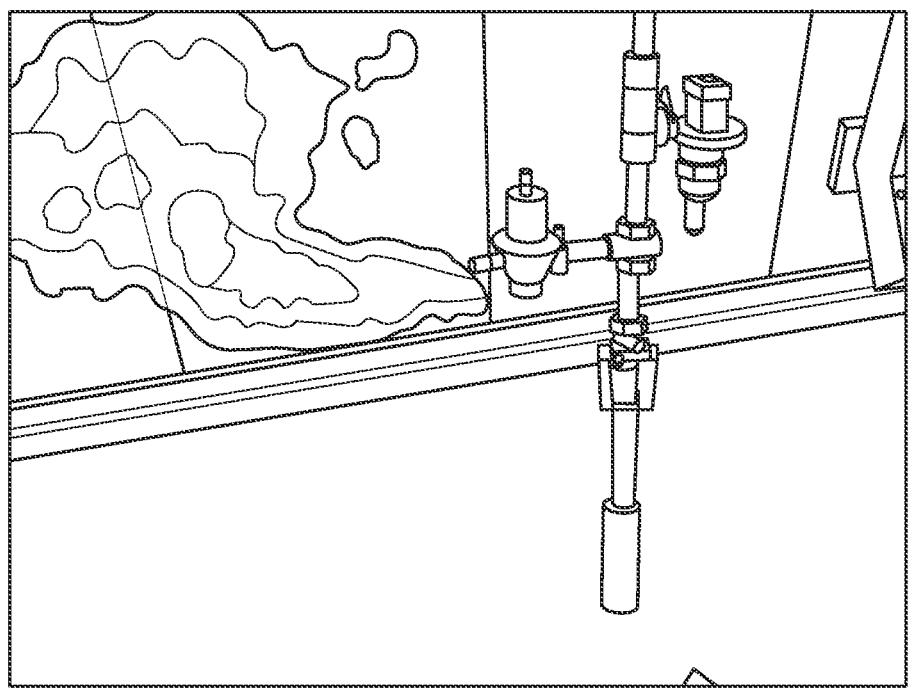

FIG. 1C is a schematic showing a cross sections of the prototype SWIR scanning optical gas sensor and illuminator shown in FIG. 1B and shown mounted on a rotatable stage 1B FIG. 1D is a schematic illustrating an optical path to the optical gas sensor (also referred to as camera) of the prototype SWIR scanning optical gas sensor and illuminator shown in FIG. 1B FIG. 1E is a schematic illustrating an optical path from the illuminator of the prototype SWIR scanning optical gas sensor and illuminator shown in FIG. 1B FIG. 2A is an example image showing SWIR absorption imagery of a natural gas leak overlaid on a visible camera image.

Figure 2B:
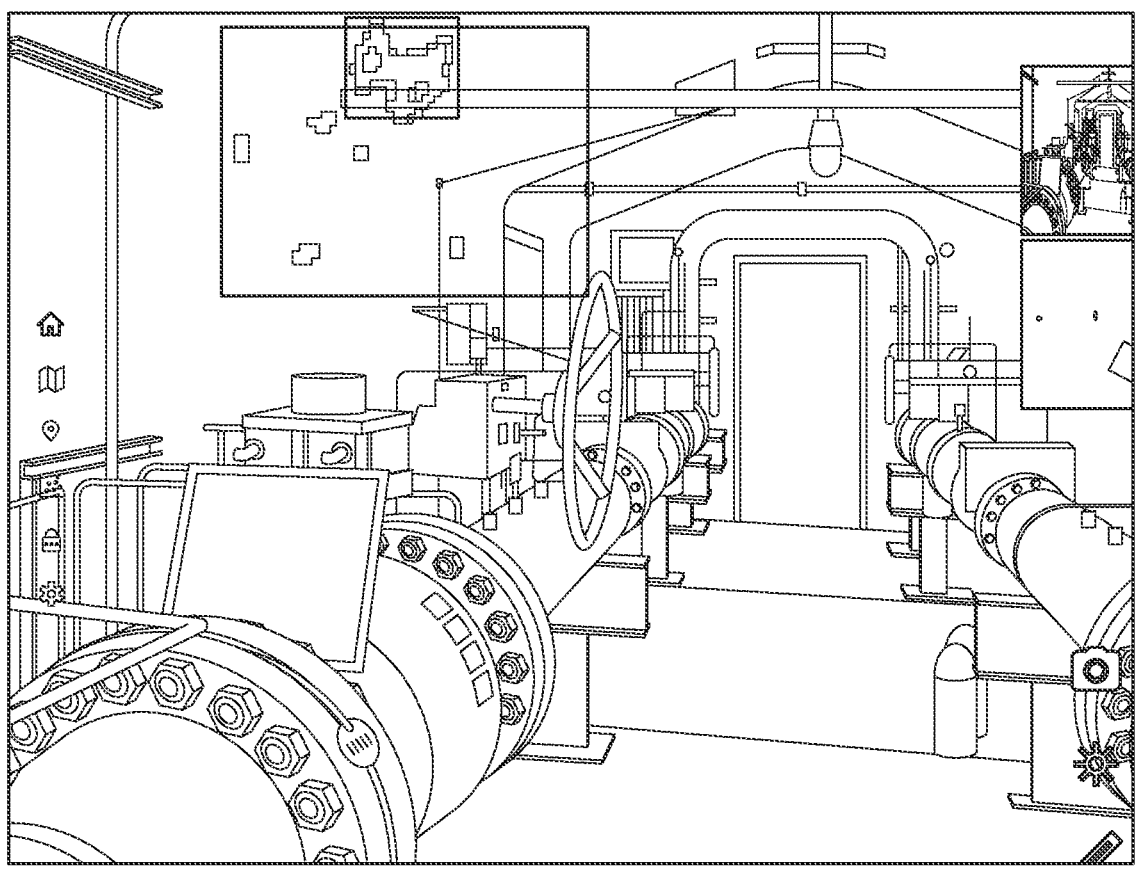

FIG. 2B is an example image showing SWIR absorption imagery of gas accumulation overlaid on a visible camera image.

Figure 3:
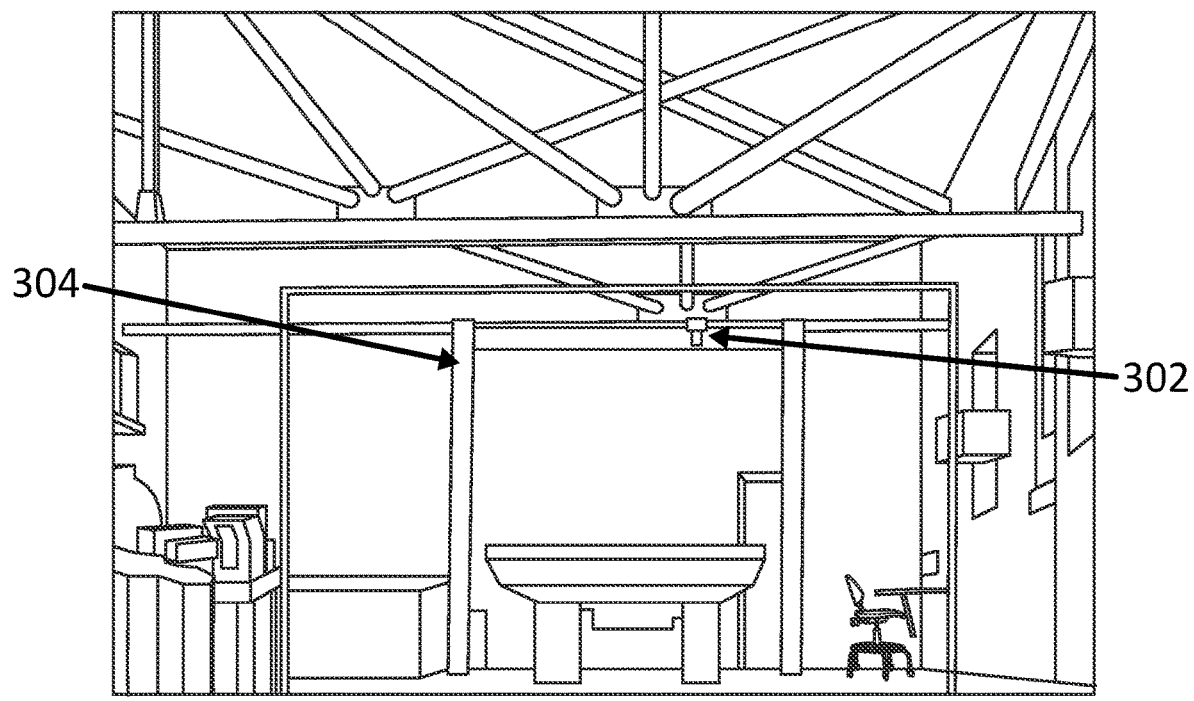

FIG. 3 is an image of an experimental reflector installment comprising a frame covered in retroreflective material that is scanned using the sensor embodiment shown in FIG. 1 to detect emission of gas, in accordance with an illustrative embodiment.

FIG. 4 is a block flow diagram showing a process for detecting gas leaks via the tailored reflector installment approaches described herein, according to an illustrative embodiment.

Figure 5A:
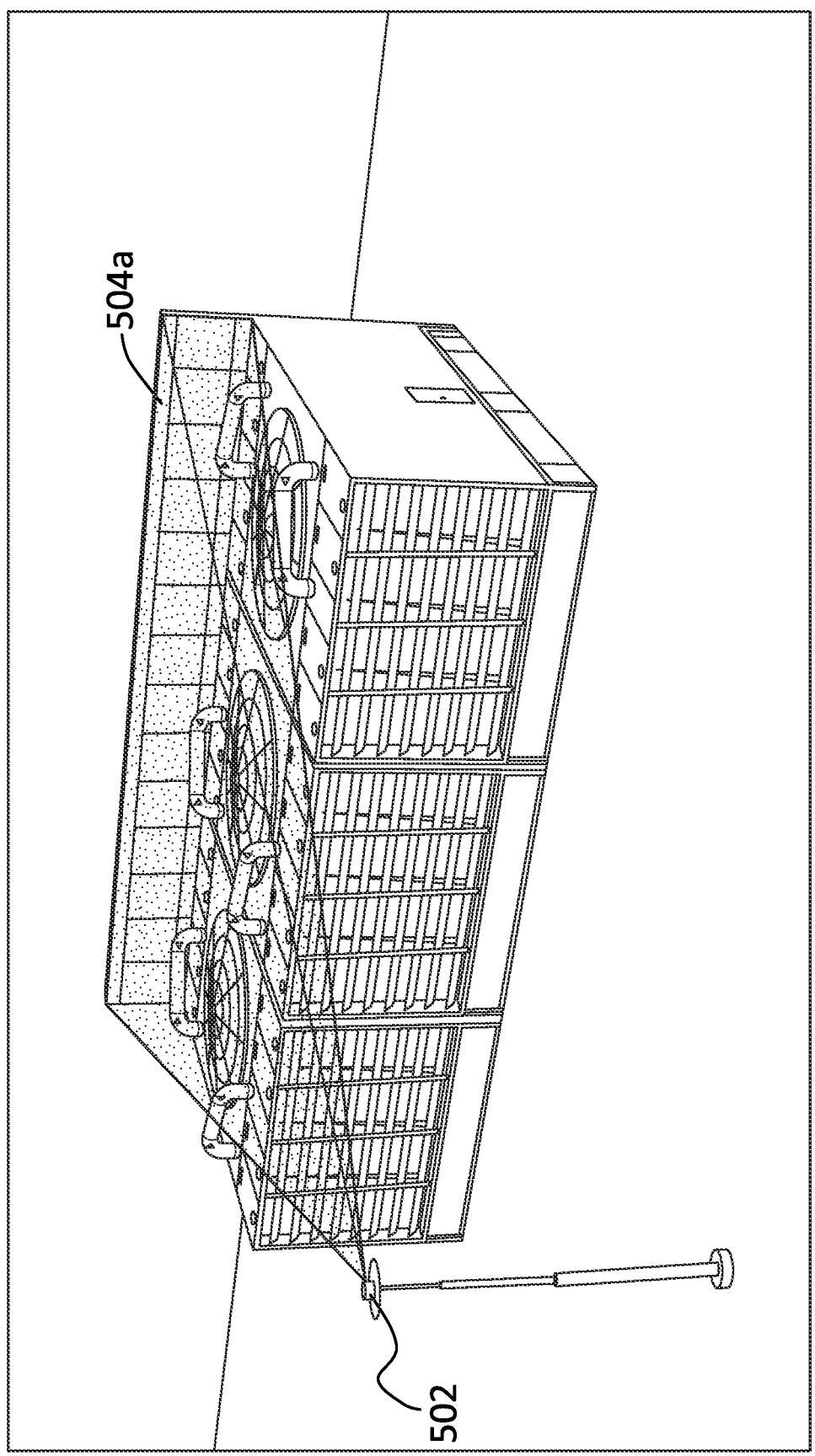

FIG. 5A is a schematic illustrating compressor coolers covered by a horizontal optical curtain formed via retro-reflective back panels and a scanning optical gas sensor and co-located illuminator, according to an illustrative embodiment.

Figure 5B:
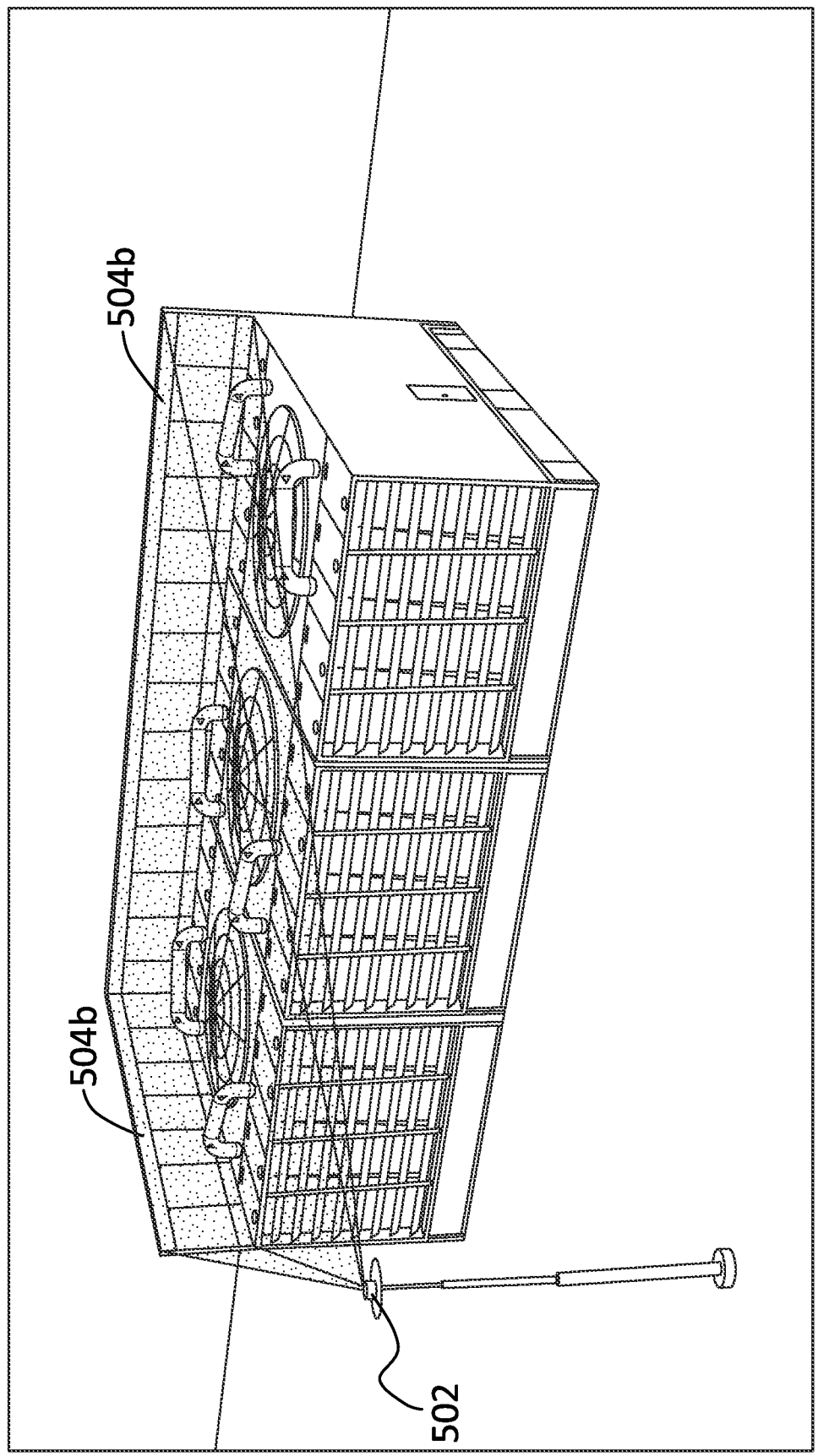

FIG. 5B is a schematic illustrating compressor coolers covered by a horizontal optical curtain formed via retro-reflective back and side panels and a scanning optical gas sensor and co-located illuminator, according to an embodiment.

Figure 5C:
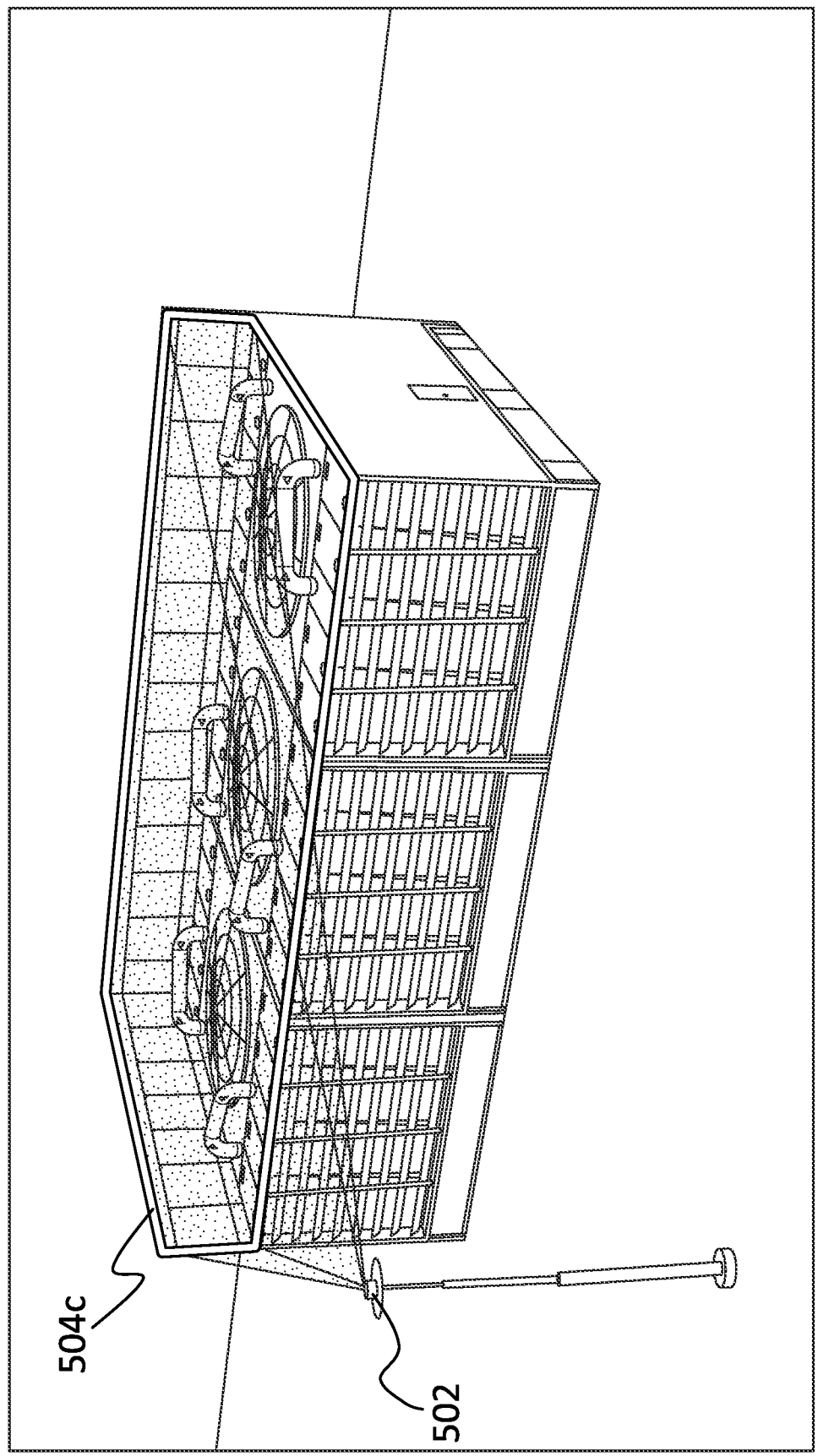

FIG. 5C is a schematic illustrating compressor coolers similar to those of FIG. 5B, with an optical curtain formed via retroreflective tape placed around a border of the tops of the compressor coolers and a scanning optical gas sensor and co-located illuminator, according to an illustrative embodiment.

FIG. 5D is a schematic illustrating detection of gas emitted from the compressor coolers via the optical curtain formed by the retroreflective tape scheme shown in FIG. 5C, according to an illustrative embodiment.

FIG. 6 is a schematic illustrating multiple tank hatches being monitored using retro-reflective panels mounted against railings along a perimeter of each tank hatch and a scanning optical gas sensor and co-located illuminator, according to an embodiment.

Figure 7A:
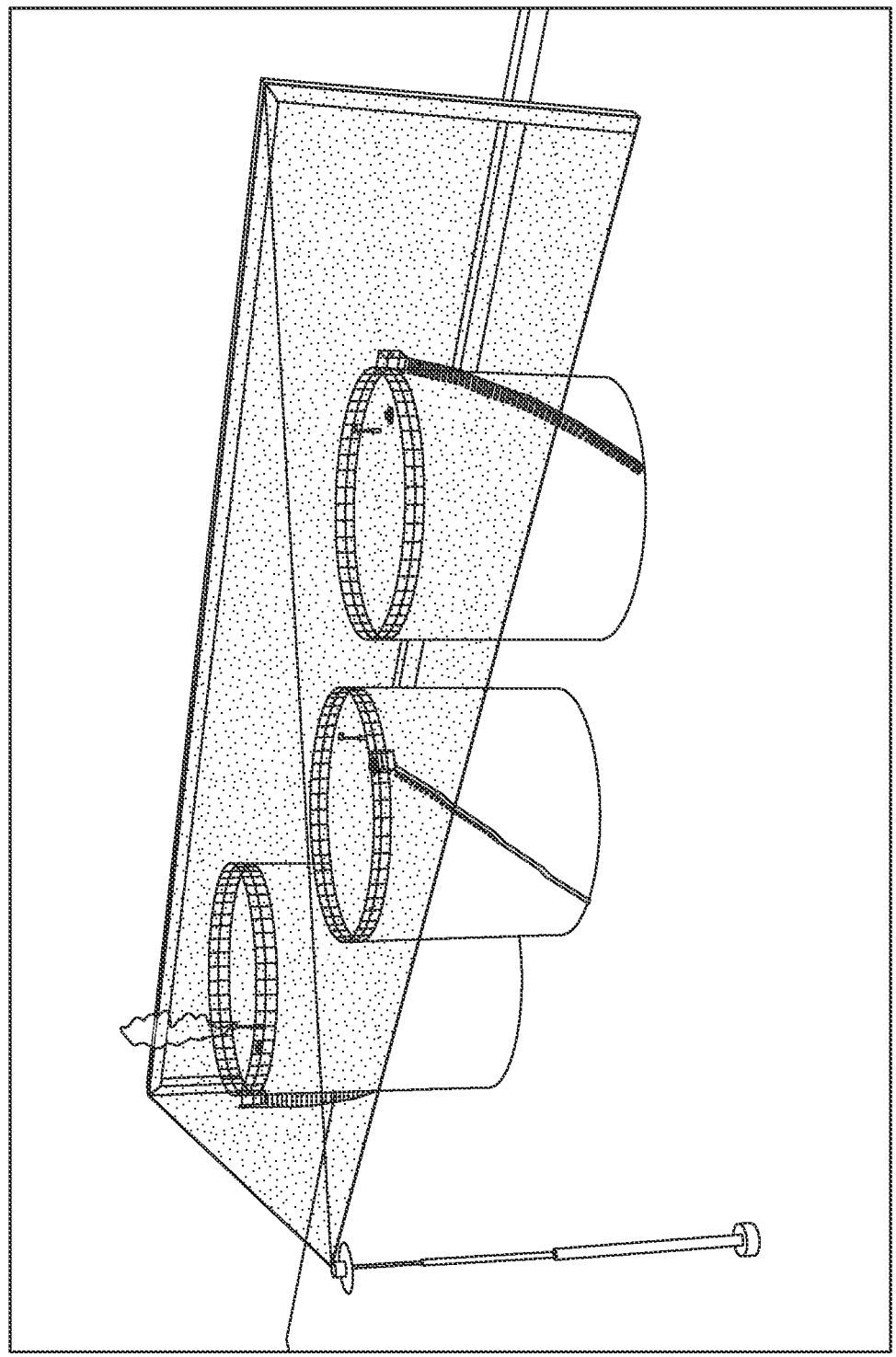

FIG. 7A is a schematic illustrating an optical curtain partially enclosing multiple tanks, according to an illustrative embodiment. The optical curtain is formed using a frame comprising retro-reflective posts and a crossbar, which form the top and sides of the curtain. A vertex of the optical curtain is at the scanning optical gas sensor and co-located illuminator. Vented gas may, for example, rise vertically through a top of the optical curtain.

Figure 7B:
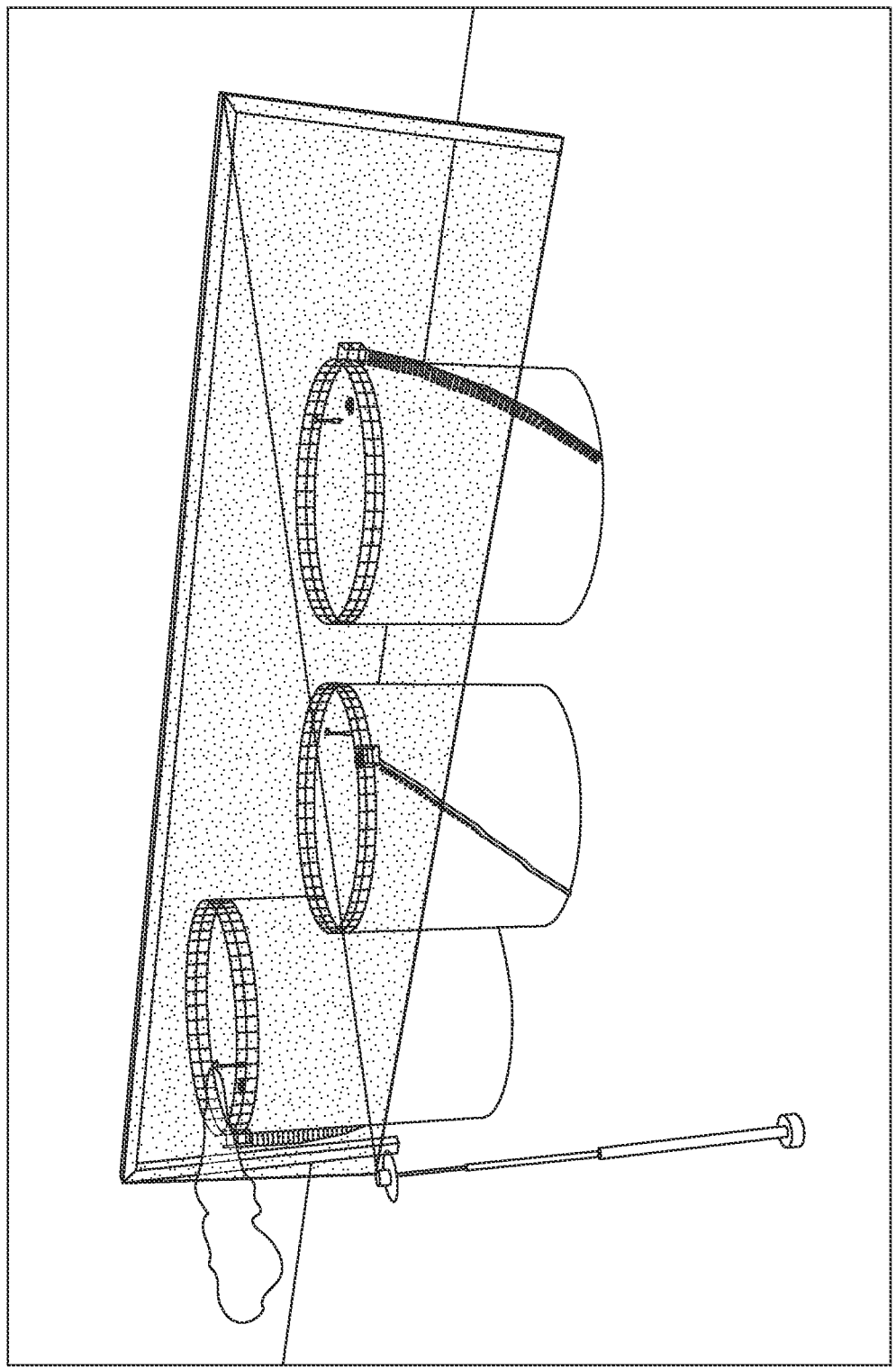

FIG. 7B is a schematic illustrating an optical curtain as in FIG. 7A, wherein vented gas disperses horizontally due to ambient winds, according to an illustrative embodiment.

Figure 8A:
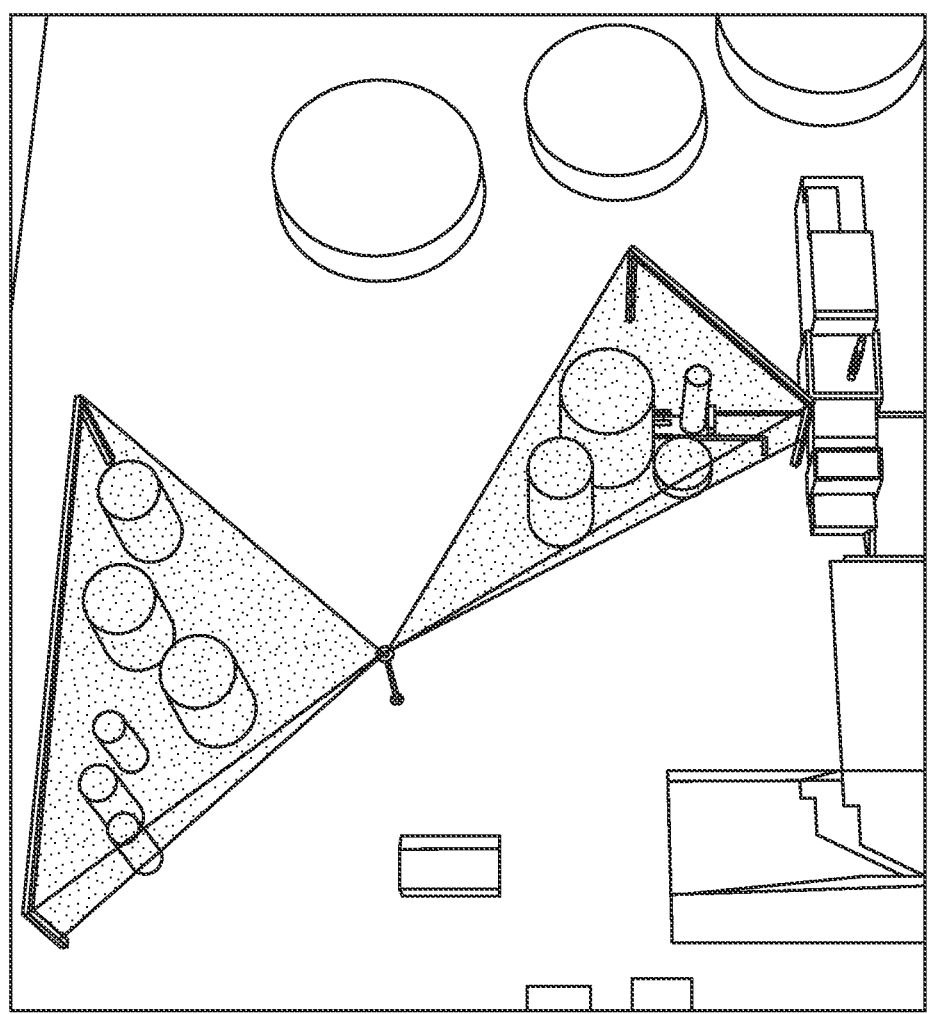

FIG. 8A is a schematic illustrating a top-down view of two monitored areas, each covered by optical curtains formed via a frame comprising retro-reflective posts and crossbars, along with a single scanning optical gas sensor and co-located illuminator, according to an illustrative embodiment.

Figure 8B:
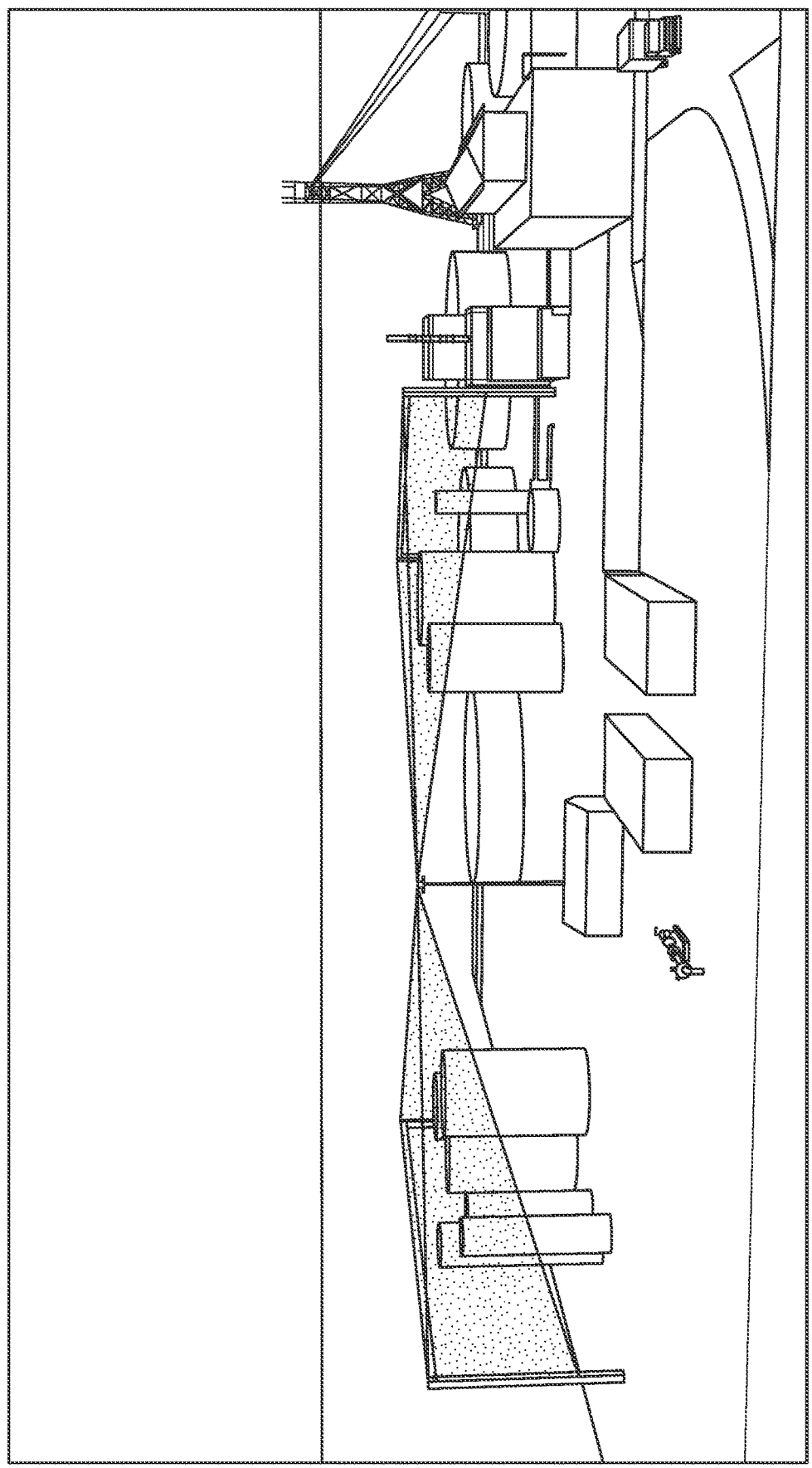

FIG. 8B is a schematic illustrating a side view of two monitored areas, each covered by optical curtains formed via a frame comprising retro-reflective posts and crossbars, along with a single scanning optical gas sensor and co-located illuminator, according to an illustrative embodiment.

Figure 9:
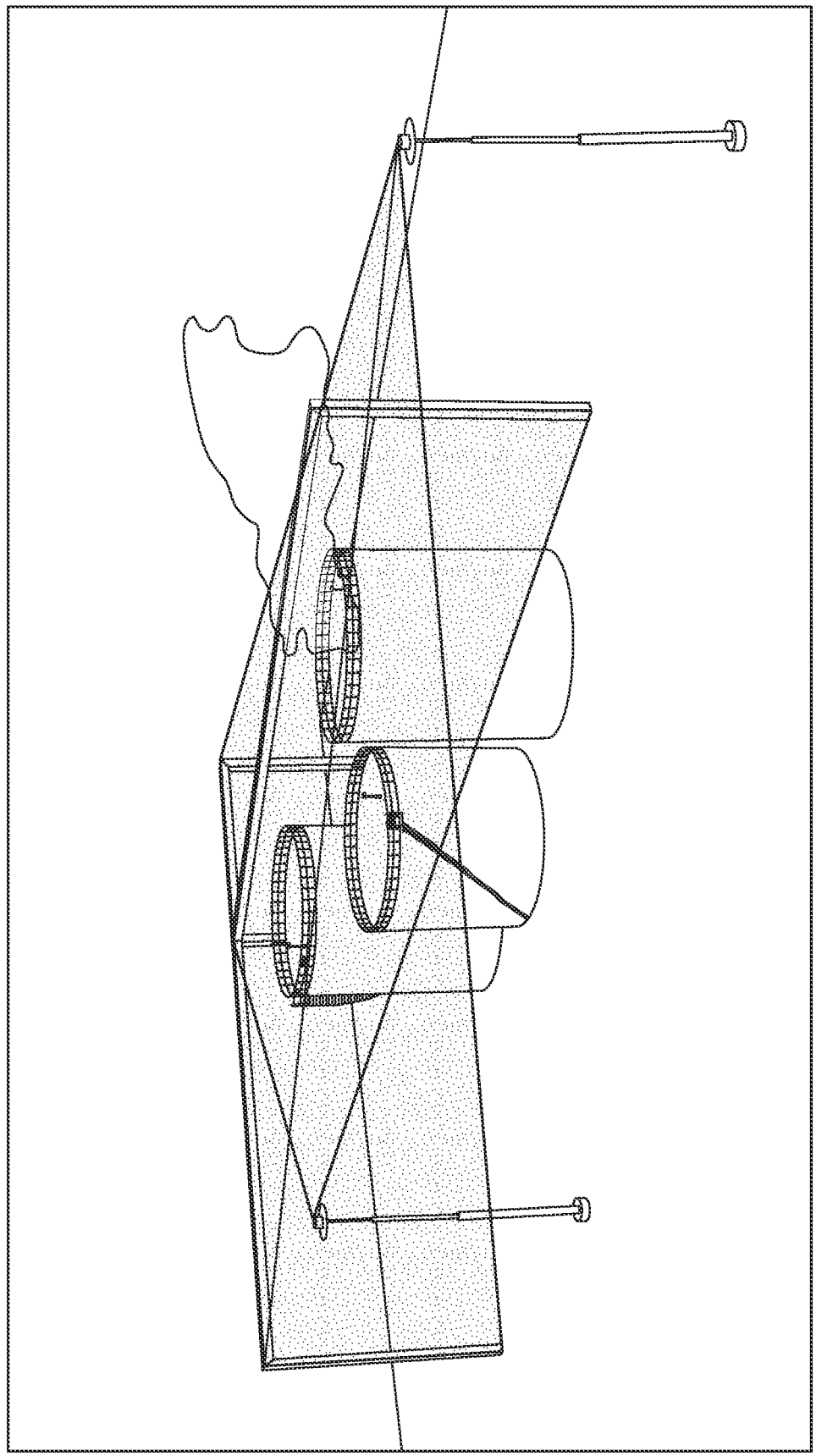

FIG. 9 is a schematic illustrating two optical sensors and co-located illuminators with two sets of retro-reflective posts and crossbars, each forming an optical curtain to enclose a group of multiple tanks to be monitored, according to an illustrative embodiment. The optical curtains cover a top and four sides about the group of tanks and allows for localization of leaks, as well as estimation of leak concentration and emission flux, in certain embodiments.

Figure 10A:
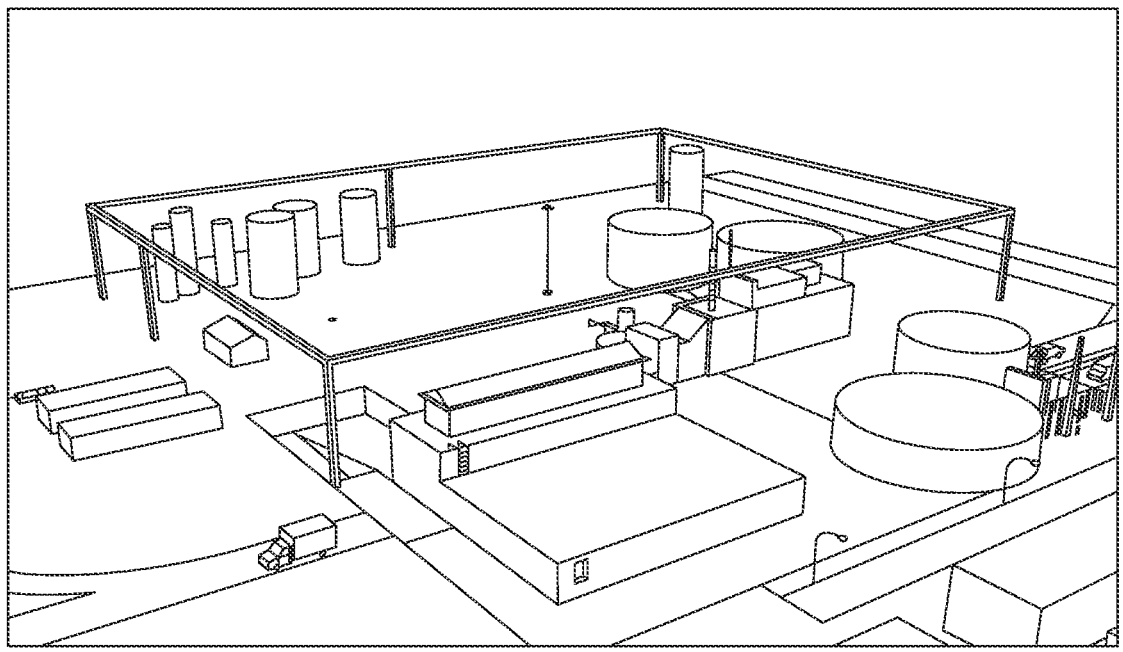

FIG. 10A is a schematic illustrating 360 degree coverage of assets by an optical curtain formed via a frame comprising retro-reflective posts and crossbars that surround an area, along with a single scanning optical gas sensor and co-located illuminator, according to an illustrative embodiment. In the embodiment shown in the figure, the scanning optical sensor and co-located illuminator are centrally mounted atop a tall mast.

Figure 10B:
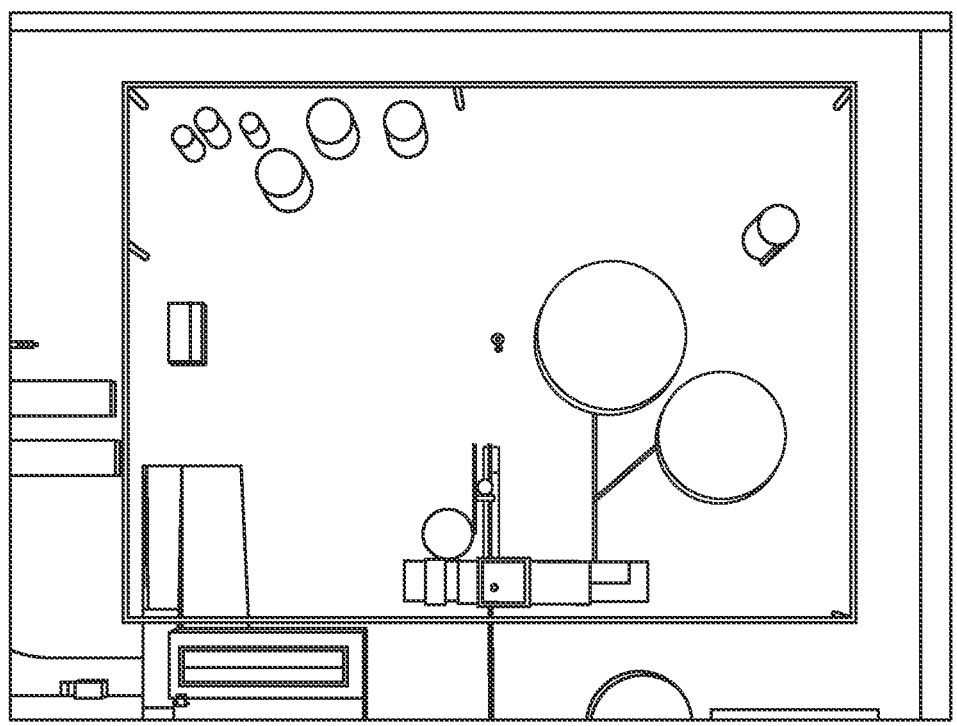

FIG. 10B is a schematic illustrating a top-down view of the embodiment shown in FIG. 10A.

Figure 11:
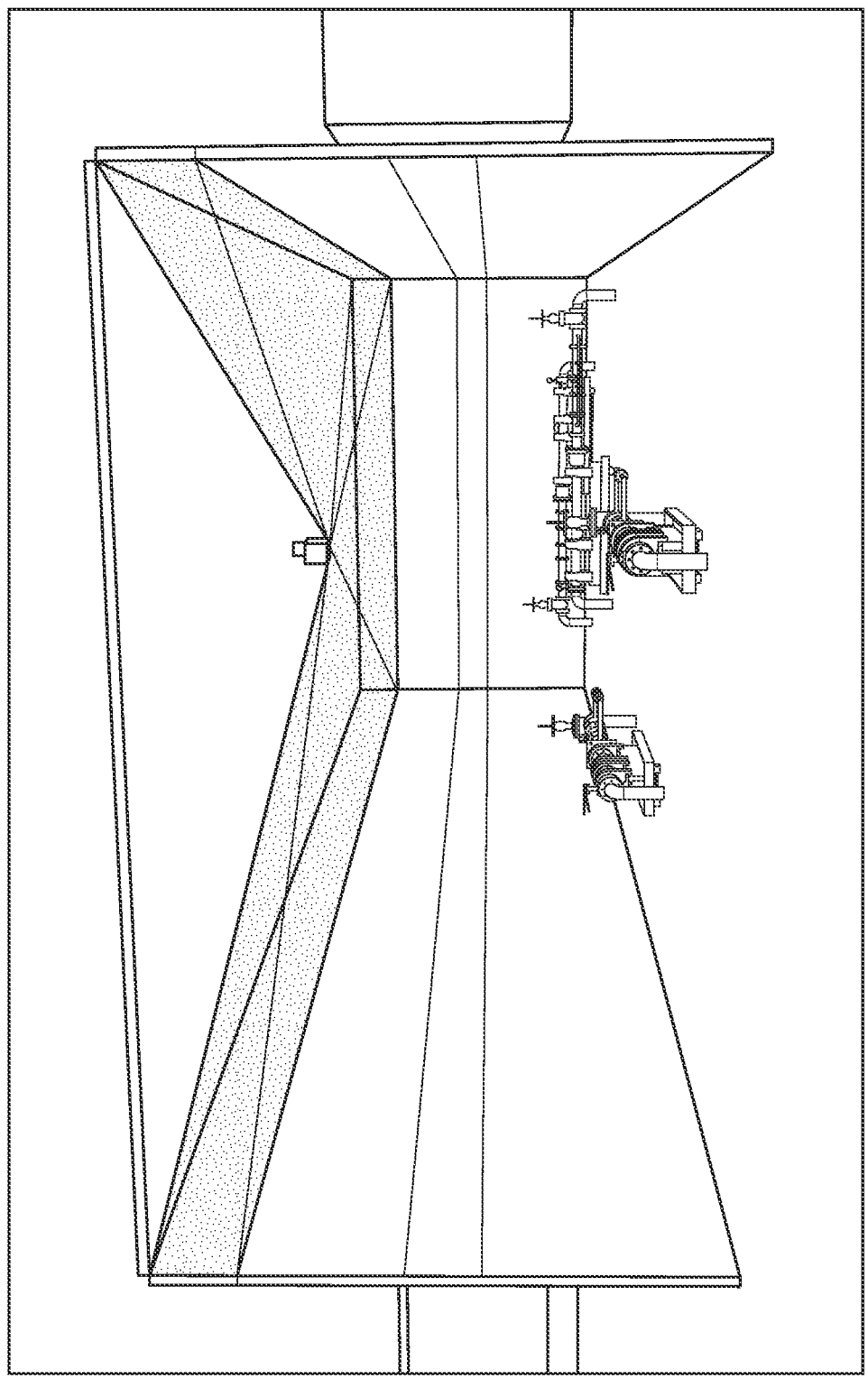

FIG. 11 is a schematic illustrating a system for monitoring for gas accumulating near a ceiling of an enclosed (or semi-enclosed) area using retro-reflective material mounted on interior walls along with a scanning optical gas sensor and co-located illuminator mounted to the ceiling, according to an illustrative embodiment.

Figure 12:
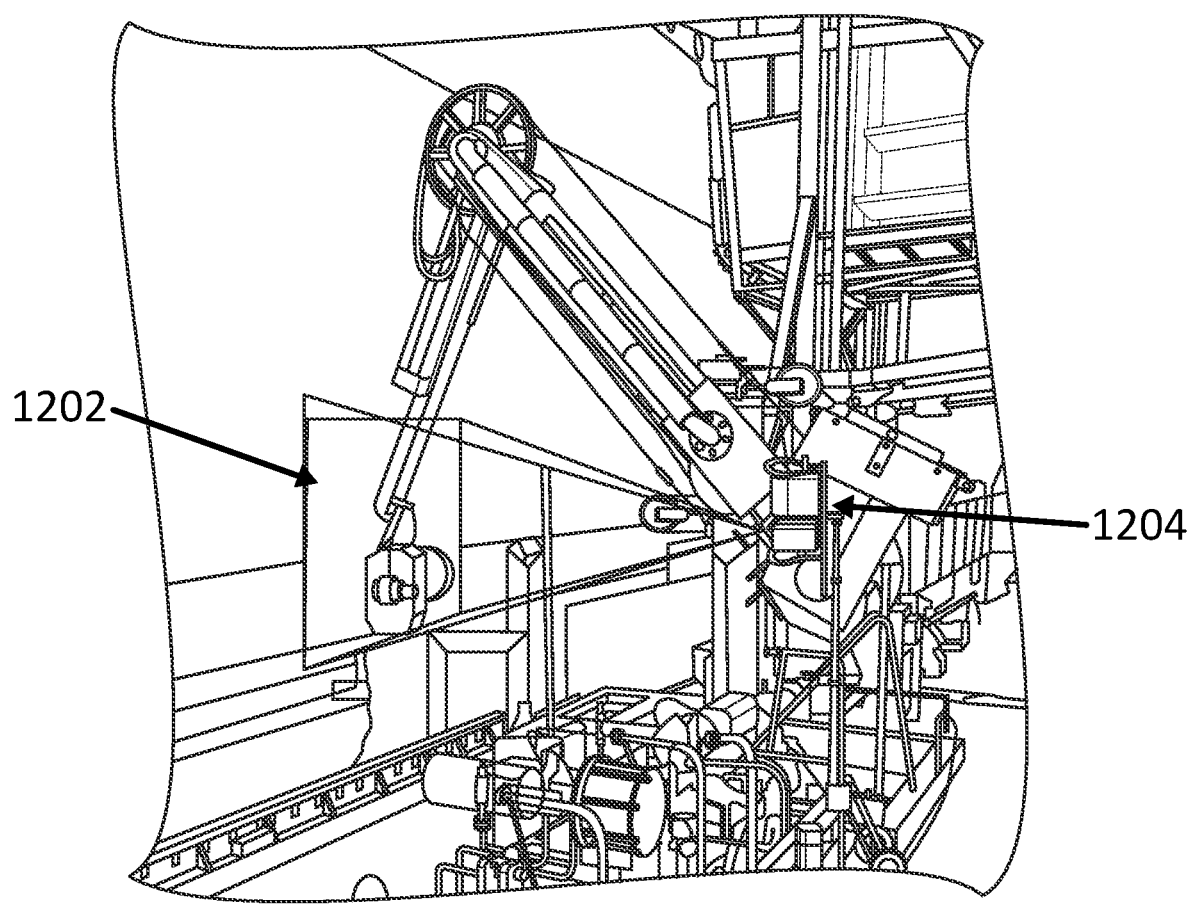

FIG. 12 is schematic showing an approach for monitoring LNG transfer onto a vessel using a retro-reflective blanket mounted around the a fueling portal of the vessel, and a nearby scanning optical gas sensor and co-located illuminator having line of sight to the fueling portal, according to an illustrative embodiment.

Figure 13:
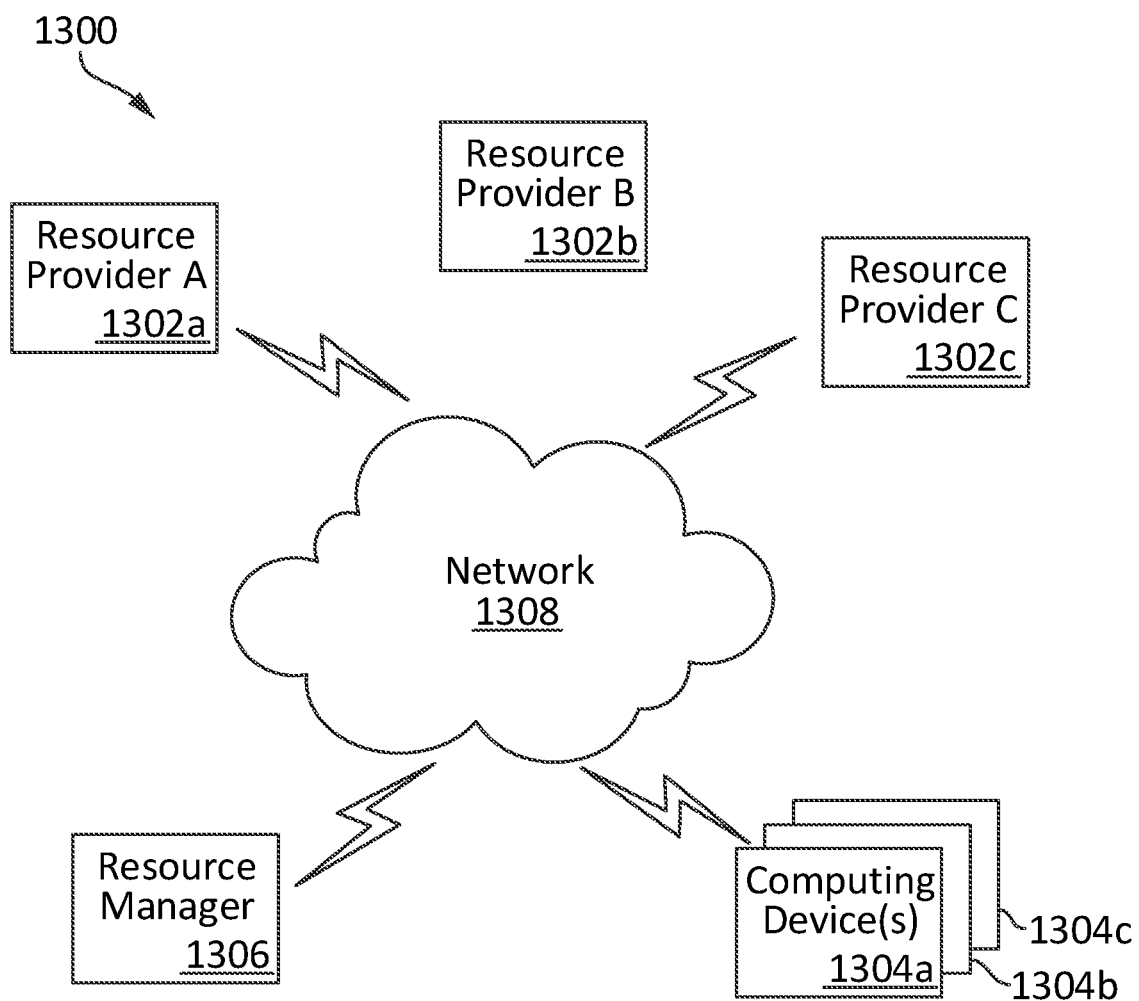
Figure 14:
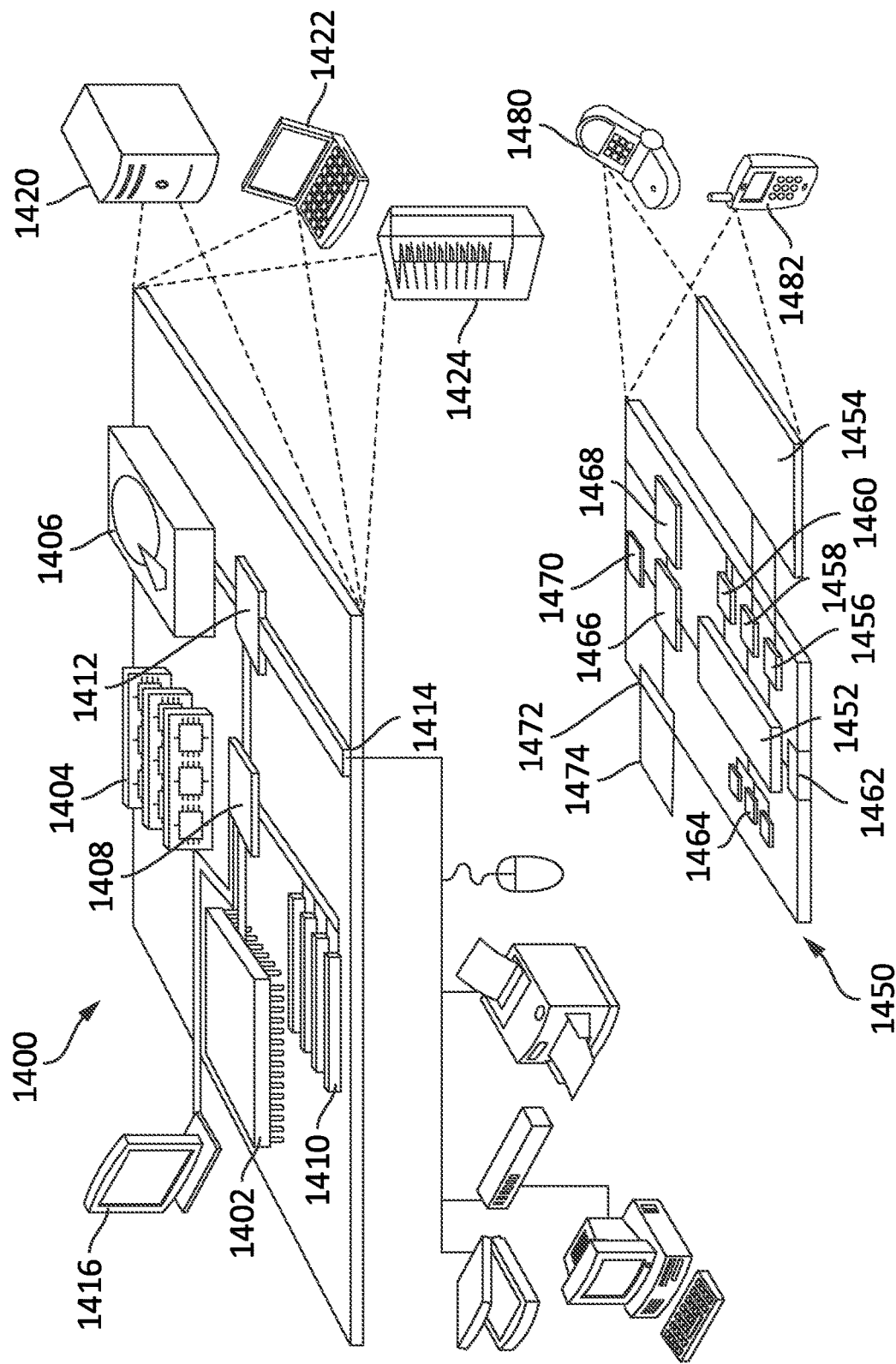

FIG. 13 is a block diagram of an exemplary cloud computing environment, used in certain embodiments FIG. 14 is a block diagram of an example computing device and an example mobile computing device used in certain embodiments.

Figure 15A:
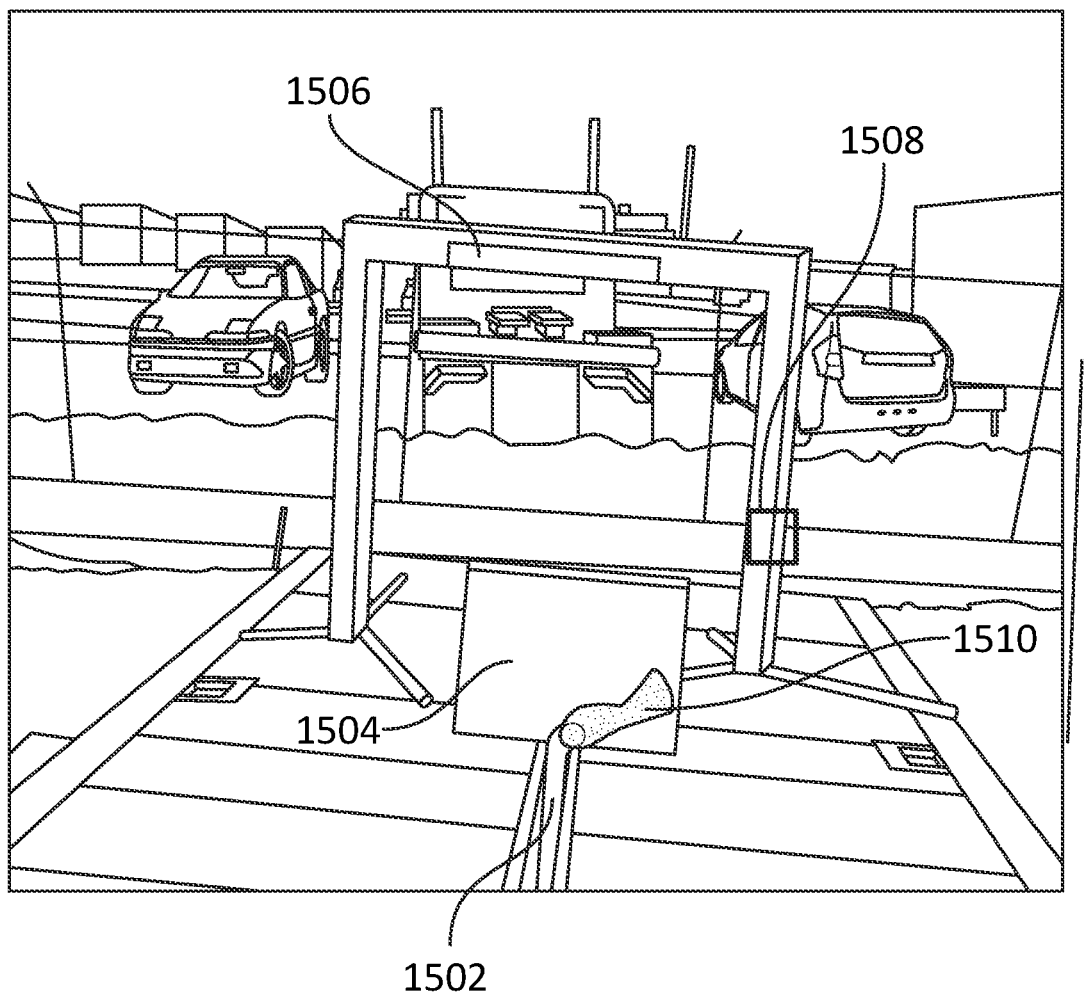

FIG. 15A is a visible camera image with SWIR spectral imaging data overlaid demonstrating a three sided optical curtain for gas detection at a 5 meter distance.

Figure 15B:
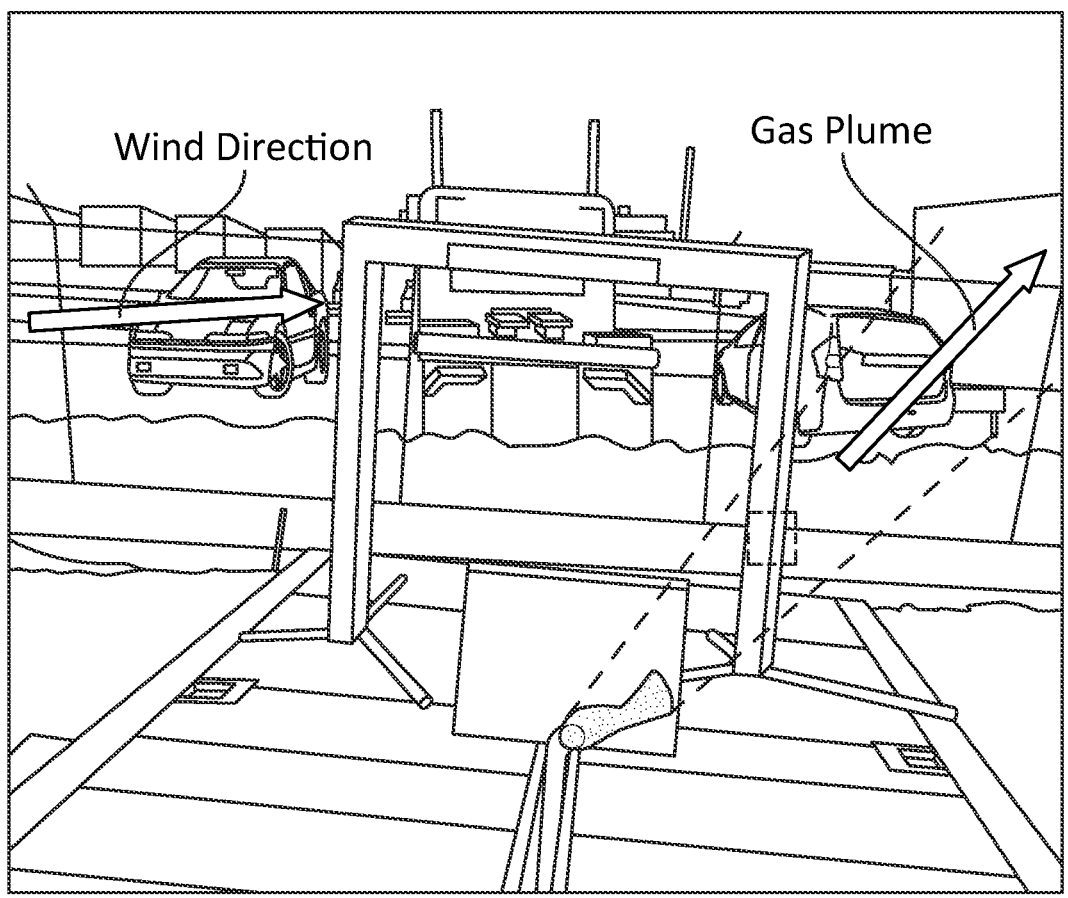

FIG. 15B is an annotated version of the image shown in FIG. 15A illustrating the interaction between wind and an emitted gas plume.

Figure 16:
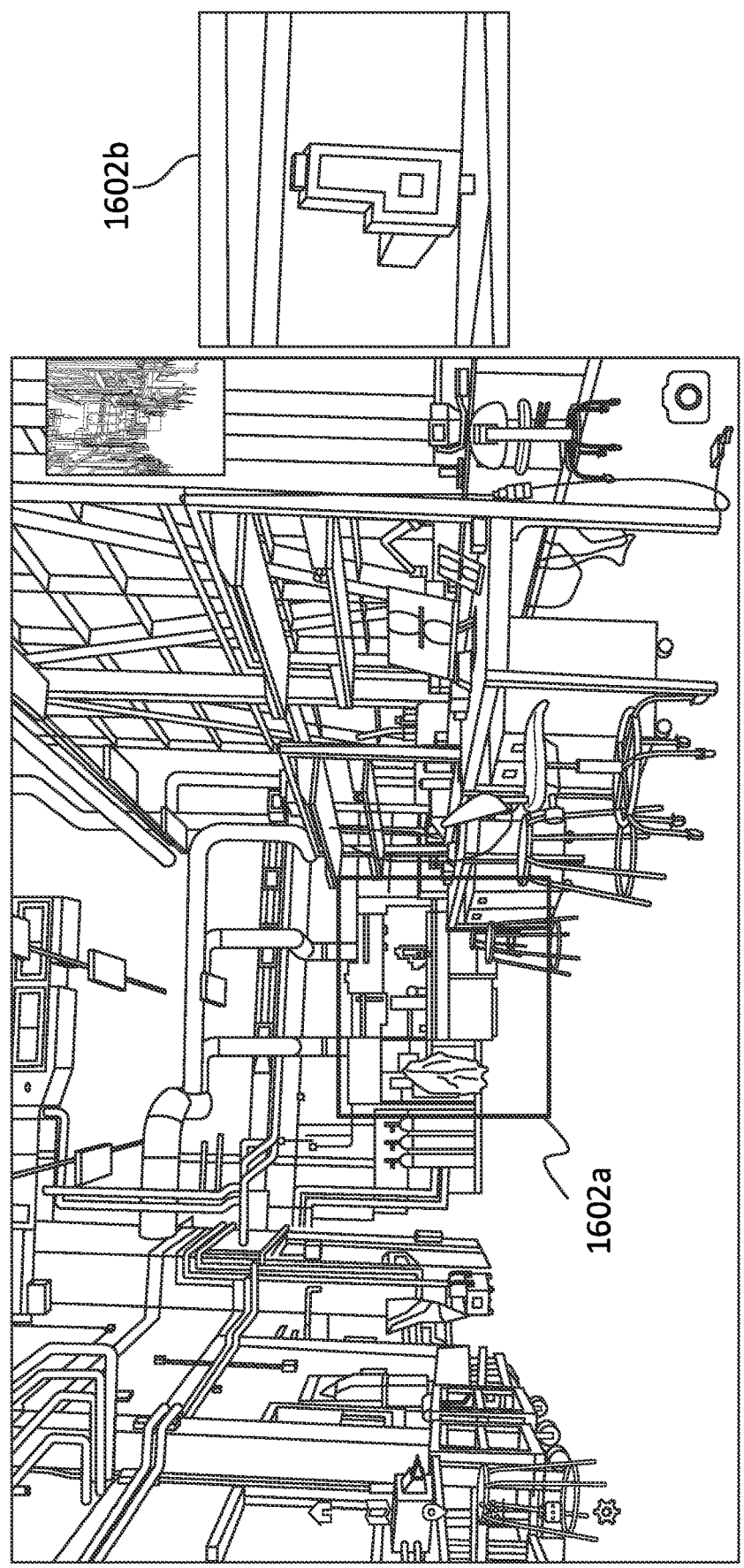

FIG. 16 is a visible image with SWIR spectral imaging data overlaid demonstrating detection of gas emission at a 20 meter distance.

Figure 17:
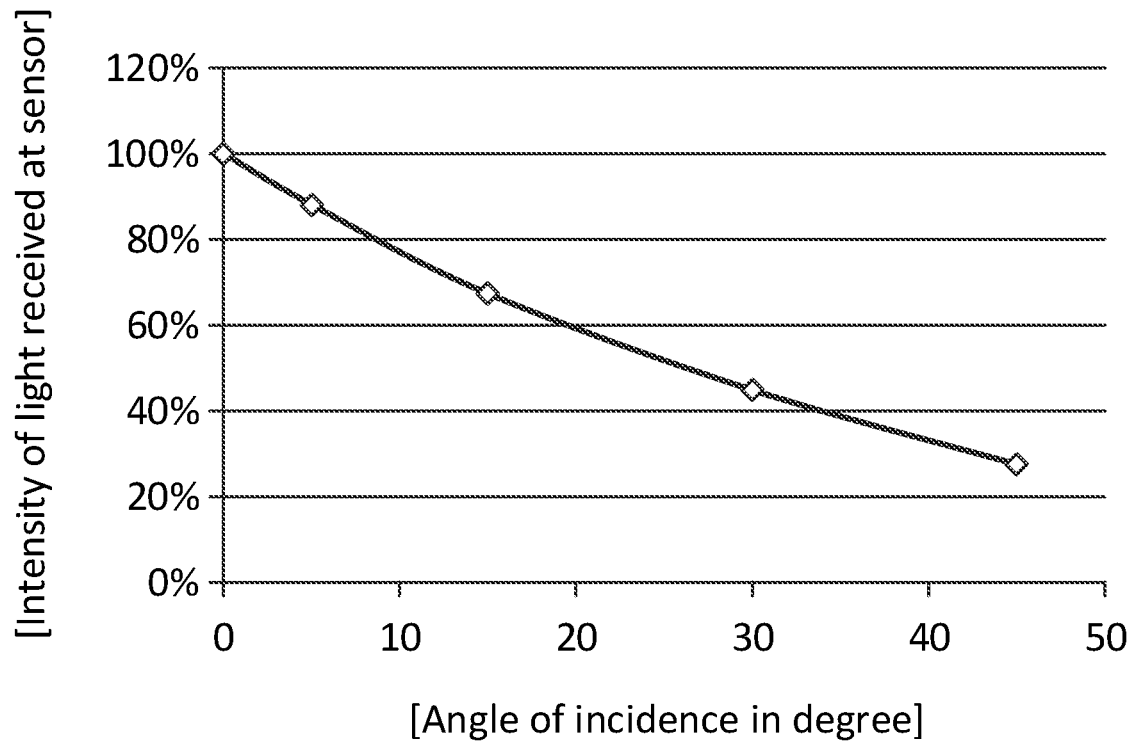

FIG. 17 is a graph showing angular dependence of light reflection from 3M™ Engineering Grade Prismatic (EGP) Reflective Sheeting 3430 in the 2250 nm-2350 nm band, measured from a 20 m distance.

Figure 18:
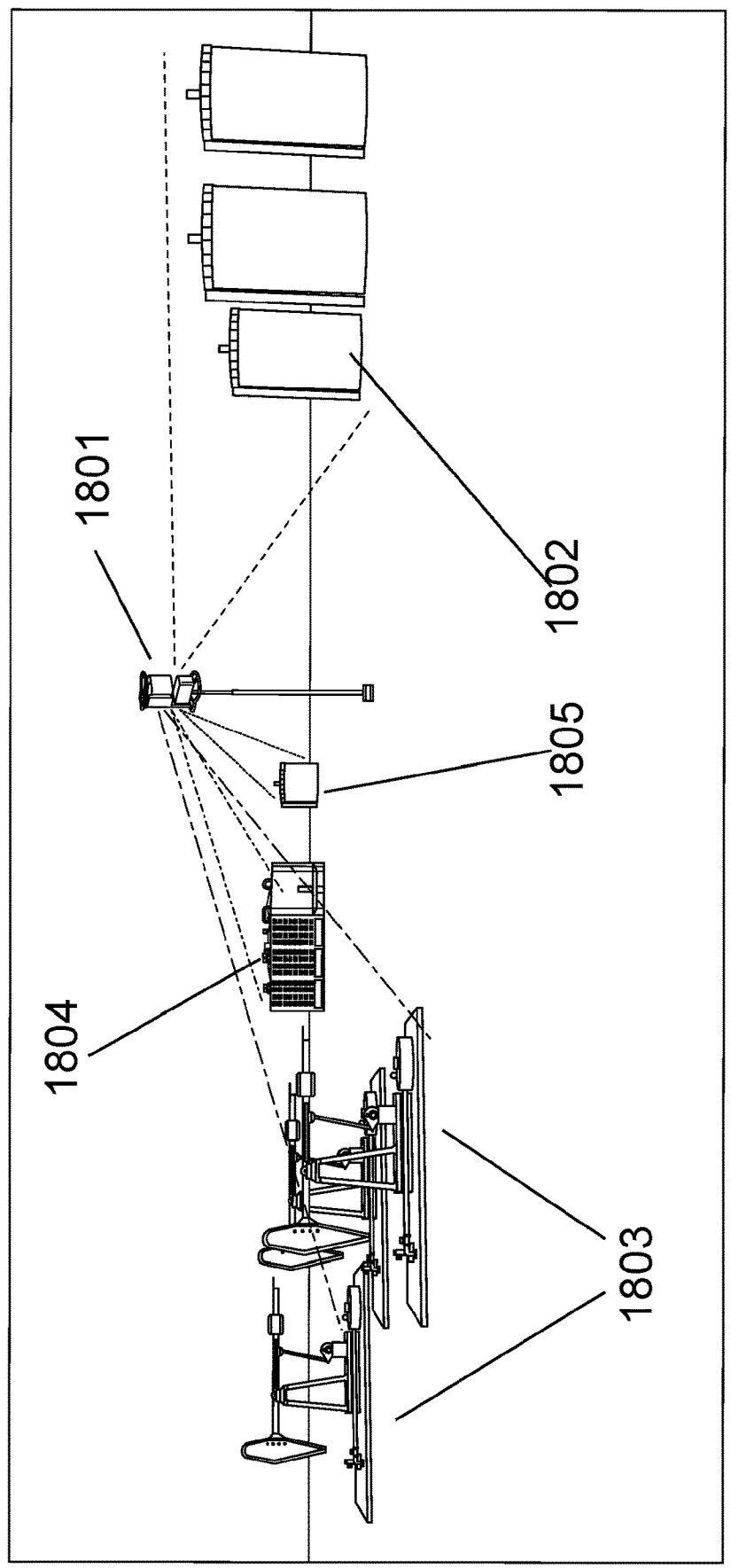

FIG. 18 is a schematic showing an optical sensor and co-located illuminator mounted on a pole and monitoring for gas leaks from four groups of assets located in separated areas across a site, according to an illustrative embodiment.

Figure 19A:
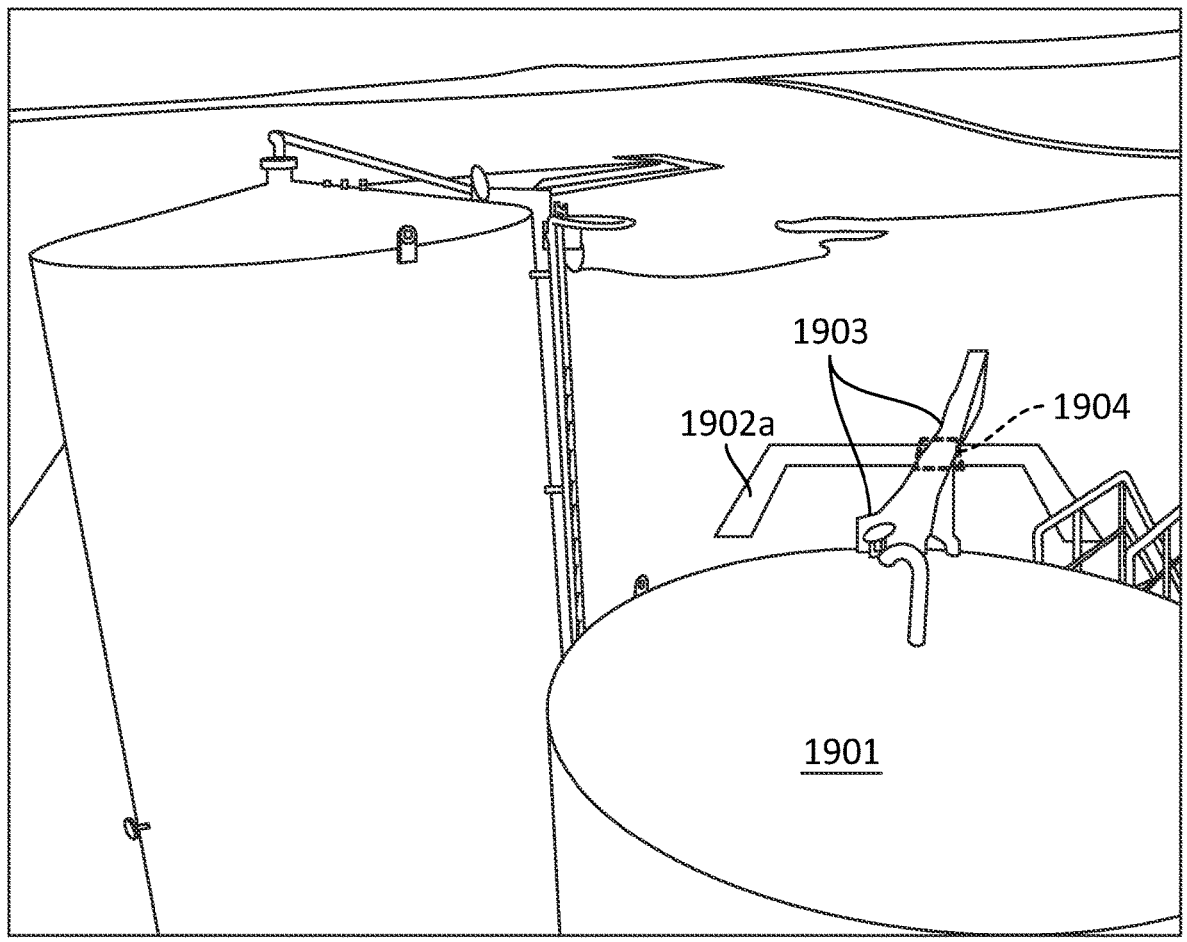

FIG. 19A is an image of column density of a hydrocarbon gas plume emitted from a storage tank as observed from the viewpoint of a co-located sensor and illuminator mounted on a mast, according to an illustrative embodiment. In the image the hydrocarbon cloud is shown as detected partially against a reflector installment and partially based on reflected sunlight against diffuse background. A conceptual representation of an arch shaped reflector installment mounted onto the ground behind the tank is shown.

Figure 19B:
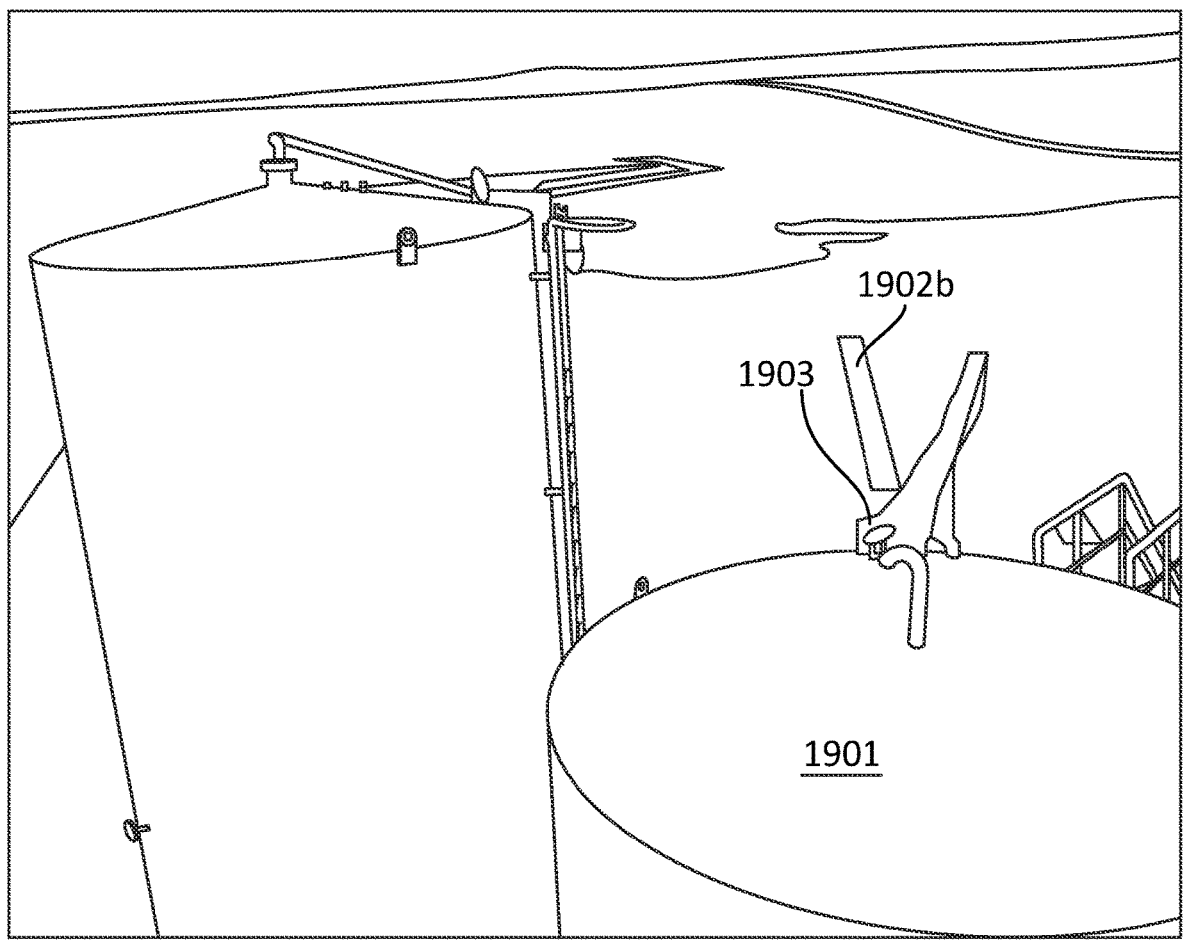

FIG. 19B is an image of column density of a hydrocarbon gas plume emitted from a storage tank as observed from the viewpoint of a co-located sensor and illuminator mounted on a mast, according to an illustrative embodiment. In the image the hydrocarbon cloud is shown as detected entirely based on reflected sunlight against diffuse background, although a reflector installment is present in the target region. A conceptual representation of line shaped reflector installment mounted onto the ground behind the tank is shown.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

Definitions

Asset: As used herein, the term "asset" refers to an object to be monitored for gas emission. In certain embodiments, assets refer to structures used for storage and/or transport of compounds of interest, such as various hydrocarbon compounds, including, but not limited to, methane, ethane, propane, butane, pentane, hexane, octane, heavier hydrocarbons or ethylene. Examples of assets include, without limitation, well pads, compressors and compressor coolers, storage or processing tanks, offshore installations, fracking rigs, liquid natural gas engines (e.g., of a ship), floating liquid natural gas platforms, liquid natural gas tankers, liquid natural gas loading/unloading equipment, above or underground pipelines, landfills, bitumen, or oilsand mines.

Reflector installment: As used herein, the term "reflector installment" refers to one or more sections of reflective material (e.g., retroreflective material) mounted within and/or about a site (e.g., comprising one or more assets or areas, such as temporary work sites, of interest) to be monitored for gas emission. The reflector installment may be permanently (e.g., adhered) or temporarily (e.g., a portable blanket or relocatable posts) affixed onto or placed nearby desired locations.

Mounted about: As used herein with reference to a reflector installment, the term "mounted about" refers to the permanent or temporary placing or installation of objects or material with, around, or on a new structure, a pre-existing structure, or a vehicle.

Spectral feature: As used herein, the term "spectral feature" refers to a group of one or more absorption lines associated with a particular compound of interest. In certain embodiments, a spectral feature comprises multiple (e.g., a plurality) of nearby absorption lines of the particular compound of interest (e.g., the spectral feature is an extended, or broadband spectral feature). In certain embodiments, such multiple nearby absorption lines are broad and overlap, producing a spectral feature comprising multiple partially overlapping absorption peaks. In certain embodiments, a bandwidth (e.g., full-width half maximum) of a spectral feature is about 25 nanometer or more. In certain embodiments, a bandwidth (e.g., full-width half maximum) of a spectral feature is about 100 nanometer or more.

Spectral bandwidth, bandwidth: As used herein, the terms "spectral bandwidth" and "bandwidth" are used interchangeably to refer to a wavelength interval over which a spectrally varying quantity, such as a power or intensity of light that is radiated, transmitted, or detected, has an appreciable amplitude, for example above a particular minimum threshold value. In certain embodiments, the minimum threshold value is a fraction of a maximum amplitude, such as a half-maximum, $1/e$, or $1/e^2$.

DETAILED DESCRIPTION

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and apparatus are described as having, including, or comprising specific components, or where processes and methods are described as having, including, or comprising specific steps, it is contemplated that, additionally, there are articles, devices, systems, and apparatus of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Documents are incorporated herein by reference as noted.

Headers are provided for the convenience of the reader— the presence and/or placement of a header is not intended to limit the scope of the subject matter described herein.

The ability to continuously monitor large sized assets for methane emissions remains a significant challenge in the oil and gas, utility, petrochemical, and heavy industries. Natural gas compressors often leak methane from worn compressor seals. Oil well batteries and tank farms store crude oil that contains various hydrocarbon liquids and methane gas, and the methane can separate from the liquids venting out at the top of the tank. Oil and gas wells may include produced water tanks that leak Methane and/or VOCs. Some oil or gas wells also release significant amounts of methane and/or VOCs via casing vent gas at intermittent and unpredictable times. LNG loading operations leak methane. Repair operations of underground pipelines, including the pinpointing of leak sites, lead to venting of natural gas that creates safety concerns. Valves and flanges in wells, separators, dehydrators, compressors, tanks, refineries and petrochemical plants develop leaks of methane, ethane, VOCs, ethylene, other hydrocarbon gases, or liquid vapors. The presence of wind in outdoor environments limits the effectiveness of conventional point and line detectors for gases. Buoyant gases such as methane can form explosive atmospheres under ceilings inside buildings that are difficult to detect. Measurements are often collected in a highly localized fashion only and in units of concentration such as for example ppm (as opposed to a unit of emission flux of gas such as for example g/min) and do not allow conclusions about the size of a leak (e.g., the severity of the leak) and what priority a reaction to a leak should be given.

Accordingly, there is a need to provide a cost effective solution to monitoring these and other asset types in order to detect and localize emission of methane and other gases or hydrocarbon liquid vapors, and to quantify the resulting emission flux. Commercially available gas detection solutions exist in the form of point sampling gas "sniffers", open path infrared (IR) line sensors, and thermal IR gas cameras. Point samplers cannot provide wide area coverage and do not respond until gas migrates from the leak site to the location of the sampler. Open path IR line sensors provide a means to detect gas passing through the single line of sight between the IR transmitter (e.g., laser or Xenon flash tube) and the detector receiver. Some open path IR sensors combine the emitter and detector into a single housing, and utilize a calibrated reflector placed in the field to establish the single line of sight of the system. Such sensors provide very limited coverage and rely on winds to carry gas emissions across the fixed IR path of the device. They also require precise and stable alignment of the transmitter and receiver (or reflector) assemblies. To create an optical detection line (sometimes referred to as a "fence") around an asset requires the installation of multiple such devices at significant expense, and this approach still relies on wind to transport gas through the line of an IR path. Moreover, such line sensors cannot localize the leak along the open sensing path, nor localize the source of the leak, nor quantify the emission flux.

Thermal IR gas cameras suitable for gas leak detection and leak localization (single spectral band or multispectral) are available, but are very expensive (US$100,000 or more). Such cameras detect and image methane and other hydrocarbons, but rely on the temperature difference between the gas and background objects in the scene. Specifically, they utilize emitted IR radiation (also referred to as thermal emissions or thermal radiation) of gas and of objects in the mid-wave and long-wave infrared region (about 3 microns to 12 microns) as part of their approach to gas detection and towards creating a visual image of gas.

A significant shortcoming of such thermal emission based approaches is that they requires sufficient temperature contrast between the thermal radiation of a background object and the gas passing in front of said object. It is often the case that the gas emissions lack sufficient thermal contrast (particularly in cold weather outdoors) to reliably detect the gas. For example, due to the lack of thermal contrast, thermal IR gas cameras are not effective in detecting gas emissions due to underground leaks that are percolating through ground surface materials. Thermal-based imaging in the mid- and/or long-wave IR spectral domain also suffers from spectral mixing or confusion due to the varying emission spectrum of the background object or material, which is challenging to measure absolutely or to estimate in a complex environment. This causes great difficulty in attempts to automate the detection of emissions with computer algorithms and causes frequent false positive alarms by such computer algorithms. Automatic detection of emissions by a computer algorithm is highly desirable as it significantly reduces or eliminates the cost of human operators, especially for permanently installed cameras. Moreover, thermal IR gas cameras frequently confuse water vapor and steam with gas since water vapor absorption bands and gas absorption bands overlap in many regions of the mid-wave and longwave infrared spectrum. Moreover, thermal imaging cameras measure temperature differences and as such have to infer column density of gas present by indirect computational techniques. This often causes a larger error in estimating emission flux in comparison with methods that directly measure column density of gas.

Instead, the approaches described herein utilize multispectral imaging in the short-wave infrared (SWIR) spectral region. There are significant advantages in using a multispectral short-wave IR (SWIR) sensor to image and quantify gas emissions. Such sensors do not rely on thermal contrast or on measuring thermal radiation emitted by bodies or by gas, and instead form imagery of gas based on the absorption of SWIR light provided in natural sunlight or by an artificial illuminator. The detected light is, accordingly, fundamentally distinct in terms of its physical origin and behavior. In particular, while black body radiators at ambient temperatures are prevalent on earth, they emit radiation primarily in the mid- and long-wave infrared spectral regions, but do not emit meaningful amounts of radiation in the SWIR band. Moreover, SWIR sensors can also detect methane and other hydrocarbons in the presence of steam and water vapor, unlike most thermal IR gas cameras. SWIR gas scanning imagers also cost significantly less than thermal IR gas cameras.

A major limitation of previous SWIR systems is in operational range. Many practicable applications for installed or relocatable SWIR sensors relevant to detecting hydrocarbon leaks require an operational range of at least 25 m, and, in certain embodiments, preferably, 50 m, or 100 m or 250 m, as well as the ability to operate during daytime and night time. Moreover, many sites do not have electrical power available and it is therefore highly desirable to design systems with low power demands (such as below 100 W, below 50 W, below 25 W or below 10 W electric power) that can be operated with a low-cost solar cell and co-located battery.

Providing these desirable features, particularly in combination, however, poses a significant challenge. In particular, in systems that rely on producing artificial SWIR illumination and detecting its reflection off of natural materials in the environment, power requirements for the illuminator can be prohibitive, since they increase approximately as a square function of the distance of the material to the illumination source and co-located sensor. For example, the configuration shown in FIG. 1A has an illumination power of approximately 350 W electrical input power and a maximum detection range for methane of approximately 3 m to 5 m (depending on the reflectance of the specific background material in the scene). and leak rate).). The illuminator shown in FIG. 1A is constructed to project a stripe on the ground.

Three conventional approaches to increase operational distances are, (i) to increase the electrical power into the illuminator, (ii) changing the illuminator design so as to illuminate (and scan) a single point, as opposed to a stripe, thereby concentrating the illumination, and (iii) to use of ambient sunlight (e.g., daylight) reflected off the background for illumination (instead of the artificial IR light source). There are, however, drawbacks to each.

With regard to increase in electrical power, while some improvements in optical design of the illuminator are possible relative to the design of FIG. 1A, the increase in power as a square function of distance will quickly overwhelm these improvements and make further increases on range impracticable. For example, a scaled up configuration of the design shown in FIG. 1A with an 5000 W electrical input power would yield a detection range of approximately 15 m to 20 m (depending on reflectance of background materials). and leak rate).). A solar cell and battery combination powering such a system would be large, expensive and not practicable.

Changing the illuminator design to provide more concentrated point illumination that can be scanned offers some improvement, but does not overcome the governing square law scaling function. FIG. 1B shows an example of an optical sensor scanner. Changing the illuminator design of FIG. 1A to an optical sensor scanner reduces the power requirement by approximately factor of 64 for a detection distance of 3 m to 5 m. The distance can then be increased again as illustrated above, however the same square function will still apply. A system with 25 m or more range might still require over one hundred W of broadband illumination power. Such steep power requirements are, again, expensive and prohibitive to desirable solar cell and battery based systems.

Imaging approaches that utilize ambient light, as opposed to artificial illumination, eliminate the illuminator and its steep power requirements. A SWIR multispectral scanning sensor based on ambient sunlight has been described in PCT Application No. PCT/US17/33157, entitled "Hydrocarbon Leak Imaging and Quantification Sensor" and filed May 17, 2017 (FIG. 4C of PCT/US17/33157 shows example sample imagery obtained utilizing ambient sunlight), as well as PCT Application No. PCT/US18/22943, entitled "Scanning IR Sensor for Gas Safety and Emissions Monitoring" and filed Mar. 16, 2018 (see, e.g., FIG. 22B therein), the contents of each of which are hereby incorporated by reference in their entirety. Images can be obtained by cameras placed on the ground at tens of meters or even a hundred meter distance at low power consumption as no power is required for an illuminator. A principal disadvantages of this approach, however, is that it relies on direct or diffuse sunlight, such that gas cannot be detected reliably or at all at night or in shadows of objects due to the absence of reflected SWIR light.

The approaches described herein overcome the challenges associated with providing for long range SWIR sensing at low power. Instead of relying in the reflectance of existing materials in a scene the approaches described herein leverage relatively inexpensive retro-reflective materials to significantly enhance the return of SWIR light from an illuminator back to an optical sensor (e.g., camera), thereby significantly extending the operational range of a SWIR sensor. Either the optical sensor (e.g., camera) or illuminator or both may be designed as scanning or non-scanning (see, for example, PCT Application No. PCT/US17/33157, entitled "Hydrocarbon Leak Imaging and Quantification Sensor" and filed May 17, 2017, PCT Application No. PCT/US18/22943, entitled "Scanning IR Sensor for Gas Safety and Emissions Monitoring" and filed Mar. 16, 2018, and PCT Application No. PCT/US18/50760, entitled "Systems and Methods for Multispectral Imaging and Gas Detection Using a Scanning Illuminator and Optical Sensor" and filed Sep. 12, 2018, the contents of each of which are hereby incorporated by reference in their entirety). In the case of a non-scanning SWIR camera utilizing optics of sufficient field of view to cover an area of interest, one implementation is to utilize a scanning SWIR illuminator in order to project light primarily along the reflective surfaces, thereby reducing the power requirements of the illuminator, e.g., a scanning SWIR searchlight illuminator or optical sensor scanner as shown in FIG. 1B. Such a scanning illuminator can be used in the presence of ambient SWIR illumination including solar illumination.

In certain embodiments, the systems and methods described herein are directed to a multi-platform system comprising one or more gas imaging sensors, one or more illuminators and one or more reflective surfaces, such that light projected from illuminators (e.g., the sun; e.g., one or more non-scanning illuminators, one or more scanning illuminators) may traverse an intervening gas cloud and, the light, being scattered back to the sensor by the reflective surface, being detected by at least one imaging sensor. In particular, in certain embodiments, the imaging sensor and illuminator can be used to create an "optical curtain" over a designated area.

Various embodiments of multispectral sensors and illuminators may be used in the tailored reflector installment approaches described herein. These include scanning multispectral SWIR imaging sensors and broadband scanning illuminators projecting structured beams of illumination (e.g., having planar striped beam patterns). Examples of these sensors are described in further detail in PCT Application No. PCT/US17/33157, entitled "Hydrocarbon Leak Imaging and Quantification Sensor" and filed on May 17, 2017, PCT Application No. PCT/US18/22943, entitled "Scanning IR Sensor for Gas Safety and Emissions Monitoring" and filed on Mar. 16, 2018, and, PCT Application No. PCT/US18/50760, entitled "Systems and Methods for Multispectral Imaging and Gas Detection Using a Scanning Illuminator and Optical Sensor" and filed on Sep. 12, 2018, the contents of each of which are hereby incorporated by reference in their entirety. In certain embodiments, a combined and co-located optical sensor scanner and scanning illuminator are used. This approach greatly simplifies synchronizing scanning of the optical sensor ifov and the illumination spot and ensuring that they overlap substantially. FIGS. 1B-1E are schematics showing an example prototype of such a system. The schematics in FIG. 1B show the combined sensor scanner and scanning illuminator. As shown, a single housing 110 comprises both the optical sensor scanner and scanning illuminator, with closely aligned detection 112 and illumination 114 paths. FIG. 1C shows a cross-section of the combined optical sensor scanner and scanning illuminator, mounted on a rotatable stage 115. FIG. 1D shows the detection side optical path 112 and FIG. 1E shows the illumination path 114.

Such multispectral imaging sensors utilize optical sensors comprising one or more detectors to detect light in a spectrally sensitive manner, over multiple spectral bands of interest. For example, in certain embodiments, optical sensors used to detect light in order to obtain multispectral absorption images as described herein may include multiple detectors (e.g., spectral detectors), each aligned and operable to detect light within a particular associated spectral band. As used herein, the term "detector", as used in reference to a detector of an optical sensor, refers to an individual detector element, such as a photodiode, or, in the context of a focal plane array, which comprises multiple detector pixels, a single detector pixel.

In such an optical sensor, each detector has its own individual detector instantaneous field of view (ifov), such that light from (e.g., emitted by and/or reflected by objects within) a scene and within a particular detector's individual ifov is captured, incident on the particular detector, and detected. The overall ifov of the optical sensor corresponds to the combined ifov of the individual detectors that it comprises. As used herein with respect to an optical sensor comprising multiple detectors, the term "instantaneous field of view (ifov)", as in a "sensor ifov", an "ifov of an optical sensor", and the like, refers to the overall ifov of the optical sensor, corresponding to the combined ifov of all the individual detectors that it comprises.

Optical sensors with multiple spectral detectors, capable of detecting light over multiple spectral bands of interest within the SWIR spectral region, can be designed in a variety of fashions. For example, as described in detail in PCT Application No. PCT/US17/33157, entitled "Hydrocarbon Leak Imaging and Quantification Sensor" and filed on May 17, 2017, PCT Application No. PCT/US18/22943, entitled "Scanning IR Sensor for Gas Safety and Emissions Monitoring" and filed on Mar. 16, 2018, and, PCT Application No. PCT/US18/50760, entitled "Systems and Methods for Multispectral Imaging and Gas Detection Using a Scanning Illuminator and Optical Sensor" and filed on Sep.

12, 2018, the contents of each of which are hereby incorporated by reference in their entirety, different arrangements of spectral filters and detector elements can be used to multiplex detection both spatially and spectrally depending on particular application requirements and cost considerations. For example, in certain embodiments, different spectral filters can be placed in front of each detector of an optical sensor, so that each detector is associated with and detects light within a different spectral band. For example, a two by two array of discrete photodetectors overlaid with a mosaic of four different spectral filters can be used to detect light within four different spectral bands from a single location. To create an image and obtain multispectral data from multiple locations, the optical sensor ifov can be scanned around a region, for example about the reflector installments described herein. In certain cases, multiple detectors can be used to detect light in different spectral bands, as well as from different spatial locations simultaneously, and avoid or reduce the need for scanning to create an image. For example, multiple linear photodetector arrays overlaid with different spectral filters, or similarly, two-dimensional focal plane array (FPA) detectors overlaid with stripes of spectral filters can be used to image spatially along one dimension and spectrally along another, perpendicular, dimension. A two-dimensional image can then be obtained by scanning the sensor ifov over a single dimension. A two-dimensional FPA can also be used to obtain a two-dimensional multispectral image in the SWIR region, with multiple spectral filters positioned over different pixels of the FPA, similar to how visible cameras use a Bayer filter mosaic for visible color imaging.

As described in detail in PCT Application No. PCT/US17/33157, entitled "Hydrocarbon Leak Imaging and Quantification Sensor" and filed May 17, 2017, PCT Application No. PCT/US18/22943, entitled "Scanning IR Sensor for Gas Safety and Emissions Monitoring" and filed Mar. 16, 2018, and PCT Application No. PCT/US18/50760, entitled "Systems and Methods for Multispectral Imaging and Gas Detection Using a Scanning Illuminator and Optical Sensor" and filed Sep. 12, 2018, detecting light within multiple spectral bands can be used to determine absorption levels associated with spectral features indicative of (e.g., due to) particular hydrocarbon compounds of interest. In particular, in certain embodiments, at least a portion of the spectral bands of interest within which light is detected overlap with one or more spectral features of a particular compound of interest. In certain embodiments, at least one spectral band is used as a reference band, having few or only weak spectral features of the various compounds of interest. Comparing the intensity of light detected within a spectral band associated with a particular compound to the intensity of light within the reference band can be used to correct for factors such as spectral dependence of the illumination source, ambient environment absorption, and spectral dependence of materials off which light is reflected in order to be detected by the optical sensor. In this manner, differential optical depths representing absorption levels due to particular spectral features can be obtained, and used to detect and quantify presence of associated compounds of interest. By combining optical depths with known absorption cross sections (e.g. the physical measure of the probability of absorption by a specific molecule as published for example by the National Institute of Standards NIST) for each compound of interest the column density of such compounds of interest can be calculated for each pixel. It can be expressed for example in units of ppm-m. It may be visually represented as a color gradient overlay over an visible image of related site by mapping a colors to units of column density. A conceptual example of a color gradient representing column density is shown in FIG. 2A.

In certain embodiments, for example where ambient light (e.g., sunlight) is not sufficient, an illumination source is also used to provide artificial SWIR illumination. The illumination source may be a broadband source, producing illumination light having a spectral bandwidth spanning multiple spectral features of the various compounds of interest, for example having a bandwidth of 200 nanometers or more (e.g., 500 nanometers or more, e.g. 1000 nanometers or more, e.g. 2000 nanometers or more) in the SWIR region. The illumination source may be co-located with (but not necessarily mechanically coupled to) the optical sensor. In certain embodiments, the illuminator projects a beam of illumination that is scanned in a synchronized fashion with the ifov of the optical sensor, so as to maintain overlap between the projection of the sensor ifov and the beam of illumination. Overlap between the beam of illumination and the optical sensor can also be maintained by mechanically coupling the two.

For example, as described in detail in PCT Application No. PCT/US18/50760, entitled "Systems and Methods for Multispectral Imaging and Gas Detection Using a Scanning Illuminator and Optical Sensor" and filed Sep. 12, 2018, the illumination beam can be structured to provide a substantially uniform illumination spot that covers a portion of a target surface, such as a region of a reflector installment. In particular, the illumination beam can be structured to produce an illumination spot that has a long dimension (e.g., a length) that is substantially larger than the projection of ifov of the optical sensor onto the target surface. For example, the illumination spot may be a narrow, approximately rectangular stripe or ellipsoidal in shape. The ifov of the optical sensor can then be scanned, rapidly, along the length of the illumination spot (the fast axis), while both the ifov of the optical sensor and the illumination spot are scanned, together, at a slower rate in an approximately orthogonal direction (the slow axis). This allows the ifov of the optical sensor to be raster scanned across the scene, to form a multispectral absorption image.

Scanning of the illumination spot with the ifov of the sensor so as to maintain overlap between the two can be accomplished by using separate, synchronized scanners for slow scanning of the illumination spot and ifov. A single scanner, such as a rotational stage, on which both the illumination source and optical sensor along with its scanner (responsible for scanning along the fast axis) are mounted and maintained in fixed alignment, may also be used to maintain overlap and scan the illumination spot with the ifov along the slow axis.

An example scanning multispectral short-wave infrared (SWIR) optical sensor 102 and corresponding scanning SWIR illuminator 104 which forms a stripe of illumination are shown in FIG. 1A. This illuminator-sensor ensemble is able to form images of various hydrocarbon and other gases, including the greenhouse gases methane and carbon dioxide.

In another embodiment and in order to for example reduce the power requirement for illumination the size of the illumination spot is reduced by forming an illumination spot (as opposed to a stripe or line) that substantially overlaps and/or may exceed the size of the ifov and by scanning the illumination spot and the ifov with two adjacent mirrors in synchronicity on the fast axis. In one preferential embodiment the two mirrors are mechanically coupled and rotated at the same time as shown in FIGS. 1B to 1E. Moreover, the combination of mechanically coupled mirrors, sensor and illumination source may then be scanned along the slow axis by for example a rotating stage 115 as shown in FIG. 1C.

SWIR gas imagery provides estimates of gas column density and emission flux for multiple types of emissions including high-pressure leaks (forming gas jets), low-pressure vents (forming plumes), surface emission patches (typical of underground gas pipe leaks), and extended area surface emissions. FIGS. 2A and 2B show examples of SWIR imagery as collected with the prototype of FIG. 1A. FIG. 2A shows a 10 psig leak from a pressure relief valve outdoors in a scene with combined sunlight and shadow. FIG. 2B shows a gas cloud inside a gate station that accumulated near the ceiling. Furthermore, multiple scan paths can be used to create an "optical curtain" that envelopes an asset, such that any gas leaking from the asset must cross some area of this optical curtain, at which point it is detected via the spectral absorption of SWIR light forming the corresponding area of the optical curtain.

The approaches described herein strategically locate reflective materials, or preferably retro-reflective materials in the vicinity of assets to be monitored for gas leaks. An experimental setup illustrating an embodiment of this technology is shown in FIG. 3. A SWIR absorbing test card 302 located 6 meters in front of retro-reflective tape 304 (15 cm wide tape, forming a 3 meter arch) is detected by a SWIR scanning sensor and illuminator (e.g., FIG. 1A), at a distance of 15 meters from the retro-reflective arch. This arch was clearly visible in the multispectral SWIR imagery at a range of 25 meters, using a 350 watt scanning illuminator. By way of comparison, the same system can only achieve an operational distance of 3 m to 5 m by detecting reflected artificial IR illumination of diffuse materials such as grass, soil, concrete, gravel or painted surfaces. An imaging scan over a field of view of 60 degrees wide by 45 degrees high takes approximately 5 seconds. A full 360 degree scan would require only 30 seconds. Faster or slower scan times are possible with adjustment of system parameters.

Retro-reflective materials are engineered to return incident light back in a small cone around the incident light direction. They are typically fashioned from glass beads or prismatic reflectors resembling corner cubes acting as trihedral reflectors or by means of total internal reflection. Unlike a specular or mirror reflector, which scatters incident light primarily in accordance with Snell's law, and unlike a diffuse reflector which scatters incident light uniformly as a Lambertian scatterer, retro-reflective materials scatter light primarily in the direction of the source, within a narrow cone. Retro-reflective materials can be fashioned in the form of sheets, rolls, and tapes. Retro-reflective materials are also available as paint, coating or ink (for example various products available from Prizmalite, GlowTec, Reflectionight™) or can be constructed out of available loose retro-reflective glass beads or spheres or crystals combined with some attachment method (e.g., an adhesive paste or tape) to an object. Retro-reflective materials can be made using glass beads and prismatic shapes from plastics and metal-coated plastics. Glass beads are typically used to make retro-reflective tapes, sheets, and paints, while prismatic shapes are often used to make retro-reflective tapes and sheets, but not paints. Retro-reflectors (e.g., corner cubes) can also be designed out of a range of reflective materials like polished aluminum, gold, or other metals. Moreover, retro-reflective materials are readily available from a variety of manufacturers (e.g., 3M High Intensity Prismatic Grade Reflective Sheeting 3930) and are inexpensive as they are used for a variety of applications such as transportation signage, safety markings, clothing for safety at night, as well as other related applications involving enhancing visibility at night (e.g., in lighted areas or from vehicle lights). Notably, while conventional applications of retro-reflector materials typically involve visible light, the reflector installment approaches described herein utilize retro-reflectors in an unconventional wavelength range, the SWIR.

A major advantage of using retro-reflective materials over reflective materials is that the material does not need to be precisely aligned towards the illuminator and optical sensor (e.g., camera). The incident angle of incoming SWIR light could be 30 degrees or more off the ideal perpendicular orientation and still allow for satisfactory operation of the detector system. This feature very significantly simplifies the installation of the reflector. In contrast, an installation of an open path gas detection system with separate sender and receiver components usually requires an angular precision of installation to within +/−0.5 degrees of perpendicular orientation between emitter and receiver. Moreover, the risk of mis-alignment of a reflector during operation is virtually eliminated. Use of retro-reflective materials as described herein also makes the reflector far less susceptible to problems arising from any vibrations of a surface to which such a reflector may be attached.

In certain embodiments, the approaches described herein utilize retro-reflectors in the SWIR part of the spectrum useful for detecting methane, other hydrocarbons, ammonia, and carbon dioxide. By mounting retro-reflective materials on posts, fences, crossbars, panels, walls, floors and other existing or custom installed structures (e.g., permanently installed, e.g., temporarily installed and relocatable), and scanning or imaging these materials with a multispectral short-wave infrared (SWIR) optical sensor while scanning these materials with a co-located SWIR illuminator (while possibly taking advantage of available solar illumination), an optical curtain is constructed that spans the area formed by the retro-reflective materials and the sensor.

FIG. 4 shows an example process 400 for detecting gas emission using the reflector installment technology described herein. As shown in the example process 400, an ifov of an optical sensor can be positioned towards a reflector installment 402 and light reflected from a plurality of locations along the installment detected in a spectrally sensitive manner, within one or more spectral bands of interest 404. Data corresponding to the detected light is received and/or accessed 406 by a processor of a computing device, and used to generate a spectral absorption map 408. The spectral absorption map can then be used to detect and/or quantify emission of leaking gas 410.

FIGS. 5A-D provide illustrative embodiments of the described technology wherein compressor coolers are being monitored using an optical curtain formed using reflector installments (e.g., 504a, 504b, and 504c; in general, 504) arranged along the top and partially along the side and front of the compressor coolers. FIG. 5A shows compressor coolers covered by a horizontal optical curtain formed via retro-reflective back panels 504a and a scanning optical gas sensor and co-located illuminator 502, according to an illustrative embodiment. The co-located sensor and illuminator 502 are positioned in close proximity to each other, for example mounted next to or on top of each other. It is not necessary to strictly align and overlap the output beam from the illuminator with the returning beam that is detected by the optical sensor (e.g., shared optics for illuminator and sensor are not needed). FIG. 5B shows compressor coolers covered by a horizontal optical curtain formed via retroreflective back and side panels 504*b* and a scanning optical gas sensor and co-located illuminator, according to an embodiment.

FIG. 5C shows compressor coolers similar to those of FIG. 5B, with retro-reflective tape 504*c* placed around a border of the tops of the compressor coolers. In one embodiment, the retro-reflective tape is about 30 cm (12 inches) wide. Other widths of retro-reflective tape can also be used, however, in certain embodiment a narrowest dimension of a retro-reflective material should at least span an individual detector ifov. Since, in certain embodiments, the optical sensor comprises multiple spectral detectors (e.g., multiple pixels with different filters in front of each detector) an oversampling approach can be used to ensure that the entire ifov of each detector lands entirely on a narrow retro-reflector (e.g., a stripe or tape). For example, a detector ifov of 10 mrad produces a 25 cm projected spot at a distance of 25 m. Accordingly, sampling every 5 mrad or finer ensures that every individual spectral detector provides a full sample of the narrow reflector material as it scans across a scene. For a narrow vertically oriented strip of reflective material, horizontal oversampling is performed and, likewise, for a narrow horizontally oriented strip of reflective material, vertical oversampling is performed. This approach ensures that the retro-reflector material subtends the full ifov of each individual spectral detector of the optical sensor.

As shown in FIG. 5C, a scanning optical gas sensor and co-located illuminator 502 illuminates the tape and detects light reflected back from the tape to form an optical curtain about the tops of the compressor coolers. Turning to FIG. 5D, gas emitted from the compressor coolers crosses the optical curtain and absorbs light traveling to and reflected from locations along the retro-reflective tape. In this manner, emission (e.g., corresponding to a leak or vent) can be detected and localized, and the spectrally sensitive nature of the detection methodology described herein allows for multiple particular hydrocarbon compounds to be identified based on the spectral bands in which they absorb. For example, as shown in FIG. 5D, rising methane gas 512*a* can be detected as it crosses 512*b* the top of the optical curtain. Volatile organic compounds (VOCs) 514*a* are heavier than air, and fall as they leak or vent. As illustrated in FIG. 5D, such VOCs can be detected as they cross 514*b* the side or the front of the optical curtain.

As illustrated in the figures, and, notably, an optical curtain is formed by the assembly of light rays emanating from a scanning illuminator, reflecting back from the retro-reflective panels or strips (e.g., comprised over many tiny retro-reflectors that cover extended strips or areas, as opposed to a few discreet corner cube reflectors that correspond to single points), to a scanning optical sensor that is nearly co-located with the scanning illuminator. This construct cannot be achieved using a scanning open path laser with a collection of discreet retro-reflecting corner cubes. The resulting optical curtain provided by the extended reflective surfaces used in the approaches described herein forms a surface in space that will detect gas crossing it. Optical curtains can be used to bound assets being monitored for emissions, and to divide space into sectors wherein gas crossing between these sectors will be detected.

In certain embodiments, a single optical sensor and SWIR illuminator may be used to monitor multiple assets of interest. FIG. 6 shows an illustrative embodiment of a single system being used to monitor multiple fuel tanks using multiple optical curtains.

In certain embodiments, such optical curtains can also be constructed over the top and along the sides of assets to be monitored for gas leaks as illustrated in FIGS. 7A and 7B. A single sensor (e.g., camera) and SWIR illuminator may be used to monitor multiple areas of interest containing assets as well (e.g., as illustrated in FIGS. 8A and 8B). The sensed absorption of SWIR light at each line of sight along a scan provides an estimate of the density of the column of gas passing through that line of sight. Neighboring lines of sight along a scan provide for estimation of a total mass of gas crossing the optical curtain during a short interval of time (e.g., the time it takes for local wind to transport through the optical curtain the total mass estimated from SWIR absorption). For example, the technology could be used to quantify vented gas rising vertically (due to buoyancy and wind) through the top of the optical curtain (e.g., as in FIG. 8A) or dispersed horizontally through the side of the optical curtain (e.g., as in FIG. 8B) due to winds. Thus, combining this estimated mass from absorption at an optical curtain with estimates of gas motion induced by buoyancy and measured local wind speed and direction, enables the emission flux to be estimated.

The optical curtains formed by scanning reflector installments as described herein do not have to be continuous, but can also be formed from multiple segments (e.g., FIG. 6). Multiple segments can also be layered next to or on top of each other, or spaced apart at select locations. Segments can form a straight line or arbitrary 3-dimensional forms. Reflectors can form areas within portions of the field of view of the optical sensor (e.g., camera) and illuminator such as shown by the reflective blanket in FIG. 12. Reflectors may be installed on or as part of moveable structures or vehicles, for example to allow the temporary establishment of safety zones during plant commissioning and plant turnarounds or during repair operations indoors or outdoors. Emissions to be monitored might be released from individual locations such as shown in FIG. 7A, FIG. 7B, and FIG. 8. They may also be released as area emissions from underground or surface sources.

In certain embodiments, two or more optical sensors (e.g., cameras) may be used to envelop assets over their top and along multiple sides, and their intersecting lines of sight can be used to localize where gas passes through the optical curtain, helping to localize the source of the gas leak and to estimate the local gas concentration. FIG. 9 shows an illustrative embodiment of such an arrangement. Two optical sensor (e.g., camera)s with co-located SWIR illuminators and two sets of retro-reflective posts and crossbars form an optical curtain enclosing multiple tanks over top and on four sides localizes leaks and provide for estimates of local leak concentration and emission flux. This can also be combined with estimates of gas motion induced by buoyancy and winds, providing an estimate of emission flux from a localized region through the optical curtain. This approach to localizing gas crossing an optical curtain formed by intersecting lines of sight is a form of tomography. Absorption sensed along lines of sight from one position of the scanning optical sensor can only determine the direction towards the gas leak, but not the distance to the gas. By intersecting lines of sight from multiple directions (e.g., from two or more scanning optical sensors), one can localize where the gas is crossing the optical curtain. Combining this location on the optical curtain with the measured local wind vector enables a gas plume to be traced back to its nearby source. Unlike gas dispersion modeling over long distances and large areas, using optical curtains to bound assets allows a simple extrapolation of gas detected on a curtain back to its source by reversing the direction of the wind vector.

Wind sensors can be incorporated into the systems and reflector installment approaches described herein in a variety of manners in order to allow wind measurements (e.g., speed and direction) to be obtained and used to localize and quantify leaks. For example, a directional wind sensor (e.g., an ultrasonic wind sensor) can be placed on an asset to be monitored. Ideally, the wind sensor is placed as close to a vent or potential leak points as possible. In certain embodiments, placing a wind sensor on an asset in this manner is not practical or cost effective, especially for example when monitoring multiple assets around a facility with many vents and many possible leak points. In such cases, a wind sensor can be mounted on a mast above or near the scanning optical sensor and illuminator, and the measured speed at the location of the optical sensor/illuminator can be used when quantifying a detected leak. In certain embodiments, measurements from multiple wind sensors located around a facility (e.g., at four corners of a facility and atop the scanning optical sensor and illuminator) can be combined with models of wind flow (e.g., a dynamical model) through the facility in order to estimate wind speed and direction at any time at each potential leak location. In certain embodiments, the operating range of optical sensor (e.g., camera) with co-located SWIR illuminator is at least 25 meters, though a range of 50 meters, 100 meters or 250 meters is desirable. Mounted at a height of, for example, 10-15 meters, the sensor system could monitor large compressors and tank farms (e.g., FIGS. 10A and 10B). With the optical sensor (e.g., camera) and co-located illuminator mounted centrally in a facility at a height above the tallest structure, it is possible to monitor a facility of 100 meter scale or more. Multiple optical sensors (e.g., cameras) and SWIR Illuminators can be configured around a large facility in combination with strategically located retro-reflective posts and crossbars to create optical curtains that cover large areas of assets to monitor for gas leaks.

In the prototype SWIR sensor shown in FIG. 1A, the sensor is of the scanning type and the ifov (angle subtended by a single spectral band detector of the multispectral sensor) is 10 milliradians. Thus, the footprint of a single detector channel (and thereby the reflector dimension representing a single pixel) is 25 cm at a distance of 25 m, and 50 cm at a distance of 50 m. By doubling the focal length of the objective lens, the size of the optical footprint can be reduced by half. By trading off lens focal length, illumination power, and effective exposure time of the sensor, it is possible to increase operating range while keeping the size of the retro-reflective materials required to form one imaging pixel to an easy to install and cost-effective width (e.g., preferably 1 to 10 cm squared, 1 to 50 cm squared, or 1 to 100 cm squared). As described herein, the size of a reflective patch or segment should be at least equal to the individual ifov of a single SWIR detector. Larger size reflectors provide additional coverage area and additional detection pixels, so can serve to enhance sensitivity and confidence in the detection of gas emissions.

The scan pattern of the SWIR illuminator and sensor across the installed reflectors can be set to trace out an optical curtain, but also automatically adjust itself to repeat scans of selected regions or segments of reflectors in order to increase confidence of possible gas detections, improve localization of detected emissions, and improve estimated emission flux. Similar intelligent scanning strategies are described, for example, in PCT Application No. PCT/US18/22943, entitled "Scanning IR Sensor for Gas Safety and Emissions Monitoring" and filed Mar. 16, 2018, the content of which is hereby incorporated by reference in its entirety.

An optical sensor (e.g., camera) and illuminator will typically be configured to cover the entire field of view formed by the reflectors at an outermost distance. For example, an optical sensor (e.g., camera) with a field of view of 60 degrees×45 degrees may be configured to scan a fraction of its vertical and horizontal field of view (for example, 40 degrees×30 degrees); however, this fractional field of view will cover an area that is substantially larger than the field of view covered by retro-reflective material. In one preferred embodiment the illuminator will be of a scanning type in both the fast and the slow axis in order to reduce the required power demand for a given target distance. In another embodiment, the field of regard of the illuminator and optical sensor (e.g., camera) will be configured such as to only observe areas where the reflective materials installed, while the optical sensor (e.g., camera) senses primarily the retro-reflected light. In any scanning implementation of either optical sensor (e.g., camera) or illuminator, the scanning (if any) by the sensor must be synchronized with the scanning (if any) of the illuminator over the reflective surfaces.

For a sensed field of view subtending 60 degrees horizontally by 45 degrees vertically, a low-resolution (e.g., 10 millirad ifov) image would comprise approximately 100 columns and 75 rows (i.e., 7500 pixels), while an optical curtain created from two vertical reflective posts and one reflective crossbar would comprise approximately 250 pixels. This small amount of data can be rapidly processed in real-time in order to detect gas absorption along these 250 lines of sight, and be used to rapidly control an intelligent adaptive scanning pattern. Also possible are smaller optical curtains encompassing only for example 10, 20 or 50 pixels, optical curtains that are of curved shape as well as optical curtains directed at only one or two sides adjacent to an asset (as opposed to three or all four sides). Similarly, the same scanning optical sensor and co-located scanning illuminator may scan multiple assets located around a site, but in various directions from an installed sensor mast. Thus, it is quite possible to acquire multispectral absorption data along some thousands of lines of sight.

In certain embodiments, the systems and methods described herein detect light both from tailored reflector installments, as well as reflected sunlight from other areas in the field of view of the camera outside such reflector installment. This approach is illustrated in FIGS. 19A and 19B, and serves to combine advantages of both the tailored reflector installment techniques described herein and the advantages of monitoring based on ambient light, such as sunlight. In particular, it allows for certain assets and/or regions of a site that may not be situated near appropriate background reflectors and/or require night time monitoring to be fashioned with tailored reflector installments, (e.g., requiring continuous monitoring), while other regions and assets (e.g., assets not requiring continuous monitoring) can be monitored using reflected ambient light with the same camera. As shown in FIG. 19A and FIG. 19B, and described in further detail in Example 5 herein, gas emission crossing in between the reflector installment and optical sensor and illuminator can be detected with a high signal to noise ratio, even with negligible ambient light, while reflection off of background material, such as ground, can be used to cover a wider region when sufficient ambient light is available.

In this embodiment, an image is formed that includes both image pixels formed based on light received from tailored reflector installations as well as image pixels formed based on light received from reflection of background materials without such tailored reflector installations. The image can be formed in several fashions. For example, a single hydrocarbon gas plume may be detected partially against a reflector installment (1904 in FIG. 19A) and partially against background materials (1903 in FIG. 19A). In another example, separate hydrocarbon gas plumes (or parts thereof spanning multiple pixels) may be detected against reflector installment and background materials. In certain cases, although tailored reflectors and background materials are being scanned by the system, hydrocarbon gas plumes may be detected only against the background materials (1903 in FIG. 19B).

Data collected with the sample system in FIG. 1A shows that the signal to noise ratio (SNR) of multispectral data collected off a retro-reflector is significantly higher compared to data collected off diffuse backgrounds like concrete, asphalt, gravel, brick, grass or dirt. In cases where SNR is too low to obtain a result using daylight reflections alone, but more spatial information is required (e.g. to provide enhanced image based vials of a gas emission to a remote viewer by means of digital transmission of such image, or to reduce the likelihood of a false positive detection by a computer algorithm) than can be provided by a given retro-reflector installation, the system can be used in a hybrid mode. In this case, both the retro-reflector and immediately surrounding area are imaged in daylight with the IR emitter running. The scene is processed using both daylight reflection and retro-reflector methods in parallel and results can be improved based on the combined evidence of the two methods.

In particular, gas clouds obscuring the retro-reflector can be assumed to obscure some portion of the adjacent background. By observing a noisy signal on the reflector that is spatially connected to a noisy signal on the adjacent background, performance can be improved in a variety of situations, described below the following use cases listed in order of increasing complexity:

False Positive Rejection

In certain embodiments, data corresponding to detected light obtained for both locations on and off a reflector installment can be used in combination to facilitate rejection of false positives. In particular, combining evidence based on light reflected from locations both on and off the reflector installment can improve the separation of true gas signals from noise. In certain embodiments, this approach utilizes the expectation that a gas signal on the retro-reflector will have a correlated signal at nearby pixels off-reflector and/or vice versa.

Visualization/Spatial Representation

In certain embodiments, once the retro-reflector signal has helped to increase confidence in a true gas detection, pixels from the adjacent background can be incorporated to fill in the shape of the gas plume crossing the retro-reflector. Without the contribution of the high-SNR reflector, these background pixels may have been indistinguishable from noise. Because the predicted boundary of the gas plume is very noisy with this method, various spatial smoothing techniques can be used.

Leak Localization and Quantification

In certain embodiments, once a 2D shape of a detected (e.g., suspected) plume is determined from obtained spectral imagery (absorption map), the determined shape information can be combined with wind speed and direction measurements to predict the location and the rate of the leak. In certain embodiments, because a retro-reflector installation may provide limited spatial information (e.g., depending on its size and location relative to the location of the leak and the direction of wind), the result from the visualization step provides important context for fluid dynamics models which estimate leak rate using assumptions about how the gas is being transported away from the leak source. Additionally, although a single-pixel perimeter of retro-reflectors can technically provide a mass-transfer estimate into or out of the perimeter, a 2D spatial representation of the gas plume may be necessary to identify or approximate the location of the source of the leak and/or the direction of the extend of the plume.

In order to cover large interiors of enclosed or semi-enclosed spaces, the sensor and illuminator may be mounted on a rotating platform suspended from the ceiling of the interior space. Installing reflective surfaces along the walls near the ceiling enables the sensing system to monitor the space beneath the ceiling, e.g., for the presence of gas due to a leak inside the space (as shown in FIG. 11 or a larger area inside the room).

In a certain embodiment, the SWIR illuminator projects a narrow beam approximately matched to the narrow dimension of the installed reflective surfaces (which, as described herein, is also approximately matched to the size of the ifov's of the individual detectors of the optical sensor), and scans along the retro-reflective surfaces in a searchlight pattern (e.g., the illuminator projects a circular beam of diameter equal to the width of a narrow reflective strip or segment at the range of the strip or segment, the illuminator being scanned by a pan-tilt unit). The SWIR sensor is required to sense the corresponding locations being illuminated by the scanned searchlight illuminator. In the case of a scanning SWIR sensor, the scan can cover any field of view angle as long as it senses the reflective surfaces in synchrony with their illumination. In the case of a staring focal plane array SWIR camera, full imagery collected at video rate without moving the sensor can detect the reflected light from the scanning searchlight illuminator.

In certain embodiments, the technology may be modular or portable in nature as shown in the illustrative embodiment of FIG. 12. FIG. 12 shows monitoring the process of LNG transfer onto a vessel using a retro-reflective blanket 1202 mounted around the vessel's fueling portal, and a nearby scanning optical gas sensor with co-located illuminator 1204 having line of sight to the fueling portal. The scanning optical sensor (e.g., camera) and illuminator assembly is mounted to a mobile unit that allows for the assembly to be transported to the desired area for temporary use. The retro-reflective blanket may be either temporary or permanently affixed to the area to be monitored. Similarly, relocatable reflectors, illuminators, and sensors can be used at temporary work sites such as outdoor repair operations of above ground and underground gas and oil infrastructure, and for plant commissioning and plant turnarounds.

The technology described herein has application to (but is not limited to) monitoring assets throughout the oil and gas industry, the petrochemical and heavy industries, pulp and paper, other producing industries, coal mining, utilities, agriculture, and scientific research. It is suitable for use in environments that are outdoors, indoors, onshore, and offshore. Thus, the technology has implications for both environmental and safety monitoring applications. A partial list of emissions monitoring applications includes, without limitation:

Well pad "tenting" near residences and townships;

Fracking well and rig monitoring for detection of gas and oil spray during operations;

Outdoor monitoring of emissions from gas plants and refinery operations;

Outdoor monitoring of emissions from compressors and compressor coolers;

Monitoring of oil battery tanks and associated equipment, for example highly toxic hydrogen sulfide gas may be associated with the presence of methane;

Confined space monitoring for Coal Mine Methane before, during, and/or after mining operations;

Confined space monitoring for tanks;

Indoor monitoring of facility ceilings for methane gas accumulation and clouds;

LNG transfer operations on land monitoring for spillage and vaporization;

LNG tanker transfer operations at sea monitoring for spillage and vaporization;

Floating LNG plant operations at sea;

LNG ship engine room monitoring for gas leaks;

Offshore oil and gas platform assets monitoring for leaks and venting;

Relocatable monitoring of heavy oil production wells that intermittently vent gas;

Relocatable monitoring for leaks during plant commissioning and turnarounds;

Relocatable monitoring for leaks during repair operations of above ground oil and gas infrastructure;

Relocatable monitoring for leaks during repair operations of underground oil and gas pipelines and infrastructure;

Relocatable or installed monitoring of areas such as landfills, industrial plants, pipelines, CO2 reinjection assets, or permafrost for surface emissions of gases;

Monitoring for surface emissions in coalmines, bitumen, or oil sand monitoring applications;

Monitoring of Methane emissions due to enteric fermentation or manure management from agricultural installations (e.g. hog farms or cattle houses);

Monitoring of Ammonia emissions, for example during fertilizer production;

Monitoring of Ethylene emissions in storage facilities, petrochemical plants, and refineries;

Replacement of so called "fence line monitoring" that is currently performed by open-path line detectors with optical curtains that bound the volume of space; and Monitoring of off-shore oil and gas drilling, loading, and processing installations.

Example 1. Demonstration of Gas Detection Via a Three Sided Optical Curtain

This example demonstrates detection of gas via a three sided optical curtain. FIG. 15A shows a visible camera image of a scene comprising a pipe 1502 releasing gas and a retro-reflector installment used to create the optical curtain. The pipe 1502 is a 2 inch vent pipe leaking at a rate of approximately 20 standard cube feet per hour (SCFH). The reflector installment includes a frame 1506 having retroreflective surfaces mounted behind the pipe. 3M High Intensity Prismatic Grade Reflective Sheeting 3930 is used as the retro-reflective surface. A scanning optical sensor and illuminator directs light to locations about the retro-reflective frame 1506 and detects light reflected back to the detector, thereby forming a three-sided optical curtain. The visible camera image of FIG. 15A is taken from the vantage point of the optical sensor and illuminator, which are situated a distance of about 5 meters from the pipe 1502 and 7 m from the retroreflective frame 1506. By virtue of the three-sided optical curtain formed using the retro-reflective frame 1506, any gas that crosses the sides of the optical curtain can be detected. For example, the image in FIG. 15A is overlaid with a false color optical absorption image that allows leaking gas to be visualized based on spectral imaging data. As can be seen, a region of gas 1508 crossing a side of the optical curtain, in front of the retroreflective frame 1506 is readily detected. The detected gas 1508 is about [internal note: the reflected gas cloud likely will have a depth to it and in principle can be anywhere between the retroreflective frame and the sensor as we are measuring column density] 1 meter to the side from the source location. In this example, a reflector panel 1504 is also placed behind the release point, and a plume of gas 1510 about 1 meter behind the release location can be observed. The reflector placed behind the release location is not required, and is used in this example for illustrative purposes, to validate the detection of the leaking gas by the optical curtain formed using retro-reflector frame 1506 and to illustrate the direction of the gas plume. Accordingly, this example shows that the systems and methods described herein can be used to detect leaks using only a narrow strip of nearby reflectors, without reflectors located behind the leak source location. Moreover, by using measurements of wind speed the source of the leak can be localized, and leak rate can be quantified. In particular, FIG. 15B shows how wind direction influences the gas plume, and the resulting absorption image formed as it passes through the optical curtain. For example, as described herein, estimates of wind direction can be combined with measurements of gas at locations along optical curtains (e.g., formed via multiple viewing directions) to localize leaks via simplified extrapolation along a vector, without necessarily requiring complex dispersion modelling.

Example 2. Demonstration of Gas Detection at 20 Meters

Example 2 demonstrates gas detection at a distance of 20 meters using 3M 3930 retro-reflectors positioned behind a gas leak source. FIG. 16 shows a visible camera image of a room with an absorption image overlaid showing levels of absorption in false color. As shown in the figure, leaking gas can be seen in a region 1602a at the back of the room (inside a fume hood). An expanded view 1602b of the region shows the detected gas leak in greater detail. Accordingly, this example shows how a single, or small number of strategically positioned retro-reflectors can be used to detect gas leaks at tens of meters using a scanning multispectral optical sensor and co-located, broadband scanning illuminator.

Example 3. Rapid Scanning Over a Wide Field of View

This example demonstrates how the tailored retro-reflector installment approaches described herein can be used to allow for large fields of view to be scanned rapidly. An example is an installation using discontinuous reflectors at an oil well as depicted in FIG. 18. Such a well may typically include one or several pump jacks, measurement equipment, a separator, and tanks. A retro-reflector panel or retro-reflector stripe may be each placed behind pump jack, a separator (or, for example, in the case of an enclosed separator behind a relief vent, on top of such separator enclosure), behind measurement equipment, and behind any pressure relief valve or hatch on top of a tank. For example, in FIG. 18 shows an optical sensor and illuminator mounted on a mast 1801 and four separated locations to be monitored: storage tanks (with pressure relief valves and thief hatches) 1802, a compressor shed (with roof vents) 1805, a separator tank roof (with vent) 1804, and pump jacks 1803 are shown.

It is noted that in an installation the retro-reflector might be placed around or behind the asset to be monitored and it may be partially visually obscured from the point of view of the optical sensor (e.g., camera) (due to reasons of ease-of-installation). From the viewpoint of the optical sensor (e.g., camera) and depending on the specific installation the retro-reflector panels might visually form one-, two-, three- or four-sided optical curtains around the asset due to part of the panel being partially visually obscured. The optical sensor (e.g., camera) and illuminator may scan the four or more retro-reflector arrays in a discontinuous fashion. For example, slow scanning across one reflector panel or stripe, then fast movement to the beginning of the second panel or stripe followed by slow scanning across this second panel or stripe and so on. This approach minimizes the response time to detect a leak by maximizing the amount of time data is collected in front of retro-reflectors as opposed to sections in the field of view without retro-reflectors.

Example 4. Angular Dependence of Reflectivity of Retro-Reflector Materials

FIG. 17 shows measurement results of the angle dependence of light retro-reflection of 3M™ Engineer Grade Prismatic Reflective Sheeting 3430 in the 2250 nm-2350 nm band, in which the illuminator and spectral sensor were approximately co-located. Data was measured from a 20 m distance. It can be seen that the percentage of light received drops steadily with increasing angle of incidence of the light onto the retro-reflector. At an angle of 45 degrees approximately 27.5% of the light is received back at the sensor relative to 100% at 0 degrees incidence angle.

Notably, retro-reflector materials are conventionally used for visible light applications (e.g. transportation and construction signage, personal safety clothing, road markings) and ASTM and manufacturer specifications show performance data for visible light. The measurement provided in this example, for the 2250 to 2350 nm band within the SWIR region show that available retro-reflector materials can be used to operate out to angles of 45 degrees away from perpendicular to a reflector panel. In certain embodiments, to maximize the sensitivity of a measurement the reflector panels may be angled such as to keep them within a incidence angle limit (e.g. 10 degrees) relative to the illuminator and sensor (e.g. camera), where this limit is set based on the desired detection sensitivity.

Example 5. Hybrid Image Formation with Reflector Installments, Artificial Illumination and Ambient Sunlight In one embodiment, the gas detection system can be operated such that it inspects across a wide area (e.g. 100 m radius×360 degrees), whereby distant pieces of operational infrastructure, representing potential distant leak sources are monitored at long-range preferentially via installation of retroreflective elements, positioned such that hydrocarbon or other gas leaks transit in front of the retroreflective elements. These distant leak sources (for example at 25 m, 40 m or 50 m to 100 m or 250 m distance) can be preferentially monitored via active SWIR illumination, scanned synchronously with the detector and directed towards these retroreflector installments. This approach is preferential as, even in the presence of sufficient (e.g. able to generate an appreciable signal at the detector) ambient or passive (e.g. sunlight) illumination, the SNR of the received light at the detector that is originating from ambient illumination reflected of background materials is much lower than the SNR of active SWIR light illumination light co-located with the detector, directed towards and returned from a retro-reflector installation received at said detector. The higher SNR of the approach with active SWIR illumination and installed retro-reflectors improves the ability to detect small amounts of gas and it reduces the likelihood of false-positive detections for a given amount of gas. Other potential leak sources present across said wide area may be monitored either by a dedicated reflector installment nearby (for example in cases where monitoring during day and night is desirable) or they may be monitored by reflected ambient sunlight. This combination allows for a reduction in the cost of reflector installments while still allowing for the possibility of detecting leaks in other areas of the field-of-view of the sensor as long as sufficient daylight is present and/or the leak size is large enough to allow for detection despite the relatively lower SNR of this approach compared to active illumination and retro-reflector installments.

This hybrid combination of active and passive illumination approaches notably utilizes a scanning, area-based imaging approach to gas leak monitoring. Availability of sufficient sunlight for passive imaging at relevant distances depends on the latitude, local climate, season, and daily weather conditions present at a site. Therefore if 24-hour, continuous monitoring is required for a site or a particular piece of infrastructure, retro-reflective elements may be positioned relative to said leak source in addition to active illumination for continuous inspection coverage. Any other potential leak sources that do not require continuous monitoring may only depend on sunlight availability for regular inspection frequency.

FIGS. 19A and 19B show two examples of how detection of a gas plume using a hybrid approach can occur. In FIG. 19A a tank 1901 is shown emitting a hydrocarbon gas plume with plume sections 1903 and 1904. The gas plume is imaged by a camera with co-located illuminator (while not shown in FIG. 19A; sensor and illuminator 1801 and tank 1802 in FIG. 18 have an approximate relative location as to generate a viewpoint as depicted in FIG. 19A). The gas plume is observed and visualized using false color representing a measured absorption level and/or determined column density. The false color representation is shown overlaid on a visible camera image for context. A conceptual representation of an arch shaped reflector installment 1902a is shown mounted onto the ground behind the tank. The portion 1903 of the visualization is determined from measurements obtained using reflected sunlight against the background, while the portion 1904 of the gas plume would be detected based on SWIR light emitted by an emitter co-located with the camera (not shown) and reflected by a retro-reflector installment 1902a. In this illustrative example, retro-reflector installment 1902a is mounted about the ground (e.g., not onto the tank). Plume section 1904 would be detected at a higher signal to noise ratio than plume section 1903.

FIG. 19B shows the same tank 1901 and gas plume as in FIG. 19A, but for a different location and geometry conceptual (line shaped) reflector installment 1902b. Due to the placement of the retro-reflector installment 1902b and the prevailing wind direction the hydrocarbon cloud would not be detected against the retro-reflector 1902b even though the co-located illuminator was emitting light onto the retro-reflector installment 1902b. The gas plume 1903 is then detected entirely based on measurements obtained using reflected sunlight against the background.

In another configuration the four separated locations 1802, 1803, 1804 and 1805 shown in FIG. 18 may be monitored in a hybrid approach where for example locations 1802, 1803 and 1804 have accompanying reflector installments while location 1805 is monitored only using ambient daylight. Other combinations of monitoring separated locations with accompanying reflector installments and monitoring based on ambient light only are possible as well.

Computer System and Network Environment

As shown in FIG. 13, an implementation of a network environment 1300 for use in providing systems and methods described herein is shown and described. In brief overview, referring now to FIG. 13, a block diagram of an exemplary cloud computing environment 1300 is shown and described. The cloud computing environment 1300 may include one or more resource providers 1302a, 1302b, 1302c (collectively, 1302). Each resource provider 1302 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1302 may be connected to any other resource provider 1302 in the cloud computing environment 1300. In some implementations, the resource providers 1302 may be connected over a computer network 1308. Each resource provider 1302 may be connected to one or more computing device 1304a, 1304b, 1304c (collectively, 1304), over the computer network 1308.

The cloud computing environment 1300 may include a resource manager 1306. The resource manager 1306 may be connected to the resource providers 1302 and the computing devices 1304 over the computer network 1308. In some implementations, the resource manager 1306 may facilitate the provision of computing resources by one or more resource providers 1302 to one or more computing devices 1304. The resource manager 1306 may receive a request for a computing resource from a particular computing device 1304. The resource manager 1306 may identify one or more resource providers 1302 capable of providing the computing resource requested by the computing device 1304. The resource manager 1306 may select a resource provider 1302 to provide the computing resource. The resource manager 1306 may facilitate a connection between the resource provider 1302 and a particular computing device 1304. In some implementations, the resource manager 1306 may establish a connection between a particular resource provider 1302 and a particular computing device 1304. In some implementations, the resource manager 1306 may redirect a particular computing device 1304 to a particular resource provider 1302 with the requested computing resource.

FIG. 14 shows an example of a computing device 1400 and a mobile computing device 1450 that can be used to implement the techniques described in this disclosure. The computing device 1400 is intended to represent various forms of digital computers, such as laptops, desktops, workstations, personal digital assistants, servers, blade servers, mainframes, and other appropriate computers. The mobile computing device 1450 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1400 includes a processor 1402, a memory 1404, a storage device 1406, a high-speed interface 1408 connecting to the memory 1404 and multiple high-speed expansion ports 1410, and a low-speed interface 1412 connecting to a low-speed expansion port 1414 and the storage device 1406. Each of the processor 1402, the memory 1404, the storage device 1406, the high-speed interface 1408, the high-speed expansion ports 1410, and the low-speed interface 1412, are interconnected using various busses, and may be mounted on a common motherboard or in other manners as appropriate. The processor 1402 can process instructions for execution within the computing device 1400, including instructions stored in the memory 1404 or on the storage device 1406 to display graphical information for a GUI on an external input/output device, such as a display 1416 coupled to the high-speed interface 1408. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 1404 stores information within the computing device 1400. In some implementations, the memory 1404 is a volatile memory unit or units. In some implementations, the memory 1404 is a non-volatile memory unit or units. The memory 1404 may also be another form of computer-readable medium, such as a magnetic or optical disk.

The storage device 1406 is capable of providing mass storage for the computing device 1400. In some implementations, the storage device 1406 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1402), perform one or more methods, such as those described above. The instructions can also be stored by one or more storage devices such as computer- or machine-readable mediums (for example, the memory 1404, the storage device 1406, or memory on the processor 1402).

The high-speed interface 1408 manages bandwidth-intensive operations for the computing device 1400, while the low-speed interface 1412 manages lower bandwidth-intensive operations. Such allocation of functions is an example only. In some implementations, the high-speed interface 1408 is coupled to the memory 1404, the display 1416 (e.g., through a graphics processor or accelerator), and to the high-speed expansion ports 1410, which may accept various expansion cards (not shown). In the implementation, the low-speed interface 1412 is coupled to the storage device 1406 and the low-speed expansion port 1414. The low-speed expansion port 1414, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1400 may be implemented in a number of different forms, as shown in the figure. For example, it may be implemented as a standard server 1420, or multiple times in a group of such servers. In addition, it may be implemented in a personal computer such as a laptop computer 1422. It may also be implemented as part of a rack server system 1424. Alternatively, components from the computing device 1400 may be combined with other components in a mobile device (not shown), such as a mobile computing device 1450. Each of such devices may contain one or more of the computing device 1400 and the mobile computing device 1450, and an entire system may be made up of multiple computing devices communicating with each other.

The mobile computing device 1450 includes a processor 1452, a memory 1464, an input/output device such as a display 1454, a communication interface 1466, and a transceiver 1468, among other components. The mobile computing device 1450 may also be provided with a storage device, such as a micro-drive or other device, to provide additional storage. Each of the processor 1452, the memory 1464, the display 1454, the communication interface 1466, and the transceiver 1468, are interconnected using various buses, and several of the components may be mounted on a common motherboard or in other manners as appropriate.

The processor 1452 can execute instructions within the mobile computing device 1450, including instructions stored in the memory 1464. The processor 1452 may be implemented as a chipset of chips that include separate and multiple analog and digital processors. The processor 1452 may provide, for example, for coordination of the other components of the mobile computing device 1450, such as control of user interfaces, applications run by the mobile computing device 1450, and wireless communication by the mobile computing device 1450.

The processor 1452 may communicate with a user through a control interface 1458 and a display interface 1456 coupled to the display 1454. The display 1454 may be, for example, a TFT (Thin-Film-Transistor Liquid Crystal Display) display or an OLED (Organic Light Emitting Diode) display, or other appropriate display technology. The display interface 1456 may comprise appropriate circuitry for driving the display 1454 to present graphical and other information to a user. The control interface 1458 may receive commands from a user and convert them for submission to the processor 1452. In addition, an external interface 1462 may provide communication with the processor 1452, so as to enable near area communication of the mobile computing device 1450 with other devices. The external interface 1462 may provide, for example, for wired communication in some implementations, or for wireless communication in other implementations, and multiple interfaces may also be used.

The memory 1464 stores information within the mobile computing device 1450. The memory 1464 can be implemented as one or more of a computer-readable medium or media, a volatile memory unit or units, or a non-volatile memory unit or units. An expansion memory 1474 may also be provided and connected to the mobile computing device 1450 through an expansion interface 1472, which may include, for example, a SIMM (Single In Line Memory Module) card interface. The expansion memory 1474 may provide extra storage space for the mobile computing device 1450, or may also store applications or other information for the mobile computing device 1450. Specifically, the expansion memory 1474 may include instructions to carry out or supplement the processes described above, and may include secure information also. Thus, for example, the expansion memory 1474 may be provide as a security module for the mobile computing device 1450, and may be programmed with instructions that permit secure use of the mobile computing device 1450. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 1452), perform one or more methods, such as those described above. The instructions can also be stored by one or more storage devices, such as one or more computer- or machine-readable mediums (for example, the memory 1464, the expansion memory 1474, or memory on the processor 1452). In some implementations, the instructions can be received in a propagated signal, for example, over the transceiver 1468 or the external interface 1462.

The mobile computing device 1450 may communicate wirelessly through the communication interface 1466, which may include digital signal processing circuitry where necessary. The communication interface 1466 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1468 using a radio-frequency. In addition, short-range communication may occur, such as using a Bluetooth®, Wi-Fi™, or other such transceiver (not shown). In addition, a GPS (Global Positioning System) receiver module 1470 may provide additional navigation- and location-related wireless data to the mobile computing device 1450, which may be used as appropriate by applications running on the mobile computing device 1450.

The mobile computing device 1450 may also communicate audibly using an audio codec 1460, which may receive spoken information from a user and convert it to usable digital information. The audio codec 1460 may likewise generate audible sound for a user, such as through a speaker, e.g., in a handset of the mobile computing device 1450. Such sound may include sound from voice telephone calls, may include recorded sound (e.g., voice messages, music files, etc.) and may also include sound generated by applications operating on the mobile computing device 1450.

The mobile computing device 1450 may be implemented in a number of different forms, as shown in the figure. For example, it may be implemented as a cellular telephone 1480. It may also be implemented as part of a smart-phone 1482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, modules described herein can be separated, combined or incorporated into single or combined modules. Any modules depicted in the figures are not intended to limit the systems described herein to the software architectures shown therein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein. Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method of generating a spectral absorption map for detecting emission of gas comprising one or more compounds of interest, the method comprising:
   (a) positioning an instantaneous field of view (ifov) of an optical sensor toward a reflector installment mounted about a site to be monitored and within a target region;
   (b) directing a beam of illumination from an illumination source and toward the reflector installment;
   (c) scanning the beam of illumination across at least a portion of the reflector installment, thereby illuminating a plurality of sampled locations on the reflector installment;
   (d) detecting, with one or more detectors of the optical sensor, light within one or more spectral bands of interest, at least a portion of which overlap with one or more spectral features associated with the one or more compounds of interest, wherein the detected light comprises:
      (i) reflected illumination light corresponding to light from the beam of illumination having been reflected from the plurality of sampled locations on the reflector installment and captured within the ifov of the optical sensor, and
      (ii) reflected ambient light having been reflected from a plurality of additional sampled locations and captured within the ifov of the optical sensor, the plurality of additional sample locations within the target region, but not on the reflector installment;
   (e) receiving and/or accessing, by a processor of a computing device, data corresponding to the detected light, comprising both (i) the reflected illumination light and (ii) the reflected ambient light; and
   (f) determining, by the processor, for each of (i) at least a portion of the plurality of sampled locations on the reflector installment and (ii) at least a portion of the plurality of additional sampled locations, an absorption level associated with at least one of the one or more spectral features using the detected light, thereby generating a spectral absorption map comprising a plurality of absorption levels, each associated with a: (i) a particular sampled location on the reflector installment or a particular additional sampled location and (ii) a spectral feature.

2. The method of claim 1, comprising,
(g) detecting the emission of the gas from within the site to be monitored using the generated spectral absorption map.

3. The method of claim 2, wherein step (g) comprises detecting the emission of the gas by automatically analyzing, by the processor, the absorption levels of the spectral absorption map.

4. The method of claim 2, wherein step (g) comprises comparing (i) a first set of one or more absorption levels associated with one or more specific sampled locations on the reflector installment with (ii) a second set of one or more absorption levels associated with one or more specific additional sampled locations in a vicinity of the one or more specific sampled locations on the reflector installment to identify the absorption levels of the first set and/or the second set as indicative of gas emission or noise.

5. The method of claim 2, comprising:
using a first set of one or more absorption levels associated with one or more specific sampled locations on the reflector installment to identify, within the absorption map, an initial portion of a gas plume boundary; and
using the initial portion of the gas plume boundary to identify, within the absorption map, one or more absorption levels associated with one or more specific additional sampled locations as indicative of gas emission and combining them with the initial portion of identified initial portion of the gas plume boundary to identify a region within the absorption map as corresponding to the gas plume.

6. The method of claim 5, comprising using the identified region corresponding to the gas plume to determine a location and/or leak rate of a gas leak from which the gas plume originates.

7. The method of claim 1, comprising using the absorption levels of the spectral absorption map to determine, by the processor, for each of at least a portion of the plurality of sampled locations, a column density of one or more of the compounds of interest.

8. The method of claim 1, wherein the one or more spectral bands of interest are within the short-wave infrared (SWIR) spectrum.

9. The method of claim 1, wherein the one or more detectors are operable to detect light within the short-wave infrared (SWIR) spectrum.

10. The method of claim 1, wherein each of at least a portion of the one or more spectral bands of interest span an extended spectral feature, comprising a plurality of absorption lines of the one or more compounds of interest.

11. The method of claim 1 wherein the ifov and the beam of illumination are scanned using mechanically coupled mirrors aligned to maintain overlap between the ifov and the beam of illumination while they are scanned.

12. The method of claim 1, wherein the reflector installment comprises one or more reflective sections mounted in proximity to, and/or mounted on, one or more assets within the site.

13. The method of claim 1, wherein the reflector installment comprises one or more reflective sections, each comprising a continuous reflective surface of sufficient size to span at least a portion of the plurality of sampled locations on the reflector installment.

14. The method of claim 1, wherein the reflector installment comprises one or more continuous retro-reflective surfaces.

15. A system for generating a spectral absorption map for detecting emission of gas comprising one or more compounds of interest, the system comprising:
(a) a reflector installment mounted about a site to be monitored within a target region;
(b) a scanning illuminator positioned in proximity to the reflector installment aligned and operable to emit and direct a structured illumination beam towards the reflector installment and scan the structured illumination beam across at least a portion of the reflector installment, thereby illuminating a plurality of sampled locations;
(c) an optical sensor positioned in proximity to the reflector installment comprising one or more detectors, wherein:
the one or more detectors are aligned and operable to detect light within one or more spectral bands of interest, at least a portion of said spectral bands of interest overlapping with one or more spectral features associated with the one or more compounds of interest, and
the one or more detectors are aligned to detect:
(i) reflected illumination light corresponding to light from the beam of illumination having been reflected from the plurality of sampled locations on the reflector installment and captured within an instantaneous field of view (ifov) of the optical sensor, and
(ii) reflected ambient light having been reflected from a plurality of additional sample locations and captured within the ifov of the optical sensor, the plurality of additional sampled locations within the target region, but not on the reflector installment
(d) a processor of a computing device; and
(e) a memory having instructions stored thereon, wherein the instructions, when executed by one processor, cause the processor to:
receive and/or access data corresponding to the detected light, comprising both (i) the reflected illumination light and (ii) the reflected ambient light; and
determine, for each of (i) at least a portion of the plurality of sampled locations on the reflector installment and (ii) at least a portion of the plurality of additional sampled locations, an absorption level associated with at least one of the one or more spectral features using the detected light, thereby generating a spectral absorption map comprising a plurality of absorption levels, each associated with: (i) a particular sampled location on the reflector installment or a particular additional sampled location and (ii) a spectral feature.

16. The system of claim 15, wherein the instructions cause the processor to detect the emission of the gas from within the site to be monitored using the generated spectral absorption map.

17. The system of claim 16, wherein the instructions cause the processor to detect the emission of the gas by automatically analyzing the absorption levels of the spectral absorption map.

18. The system of claim 16, wherein the instructions cause the processor to detect the emission of the gas by comparing (i) a first set of one or more absorption levels associated with one or more specific sampled locations on the reflector installment with (ii) a second set of one or more absorption levels associated with one or more specific additional sampled locations in a vicinity of the one or more specific sampled locations on the reflector installment to identify the absorption levels of the first set and/or the second set as indicative of gas emission or noise.

19. The system of claim 16, wherein the instructions cause the processor to:
use a first set of one or more absorption levels associated with one or more specific sampled locations on the reflector installment to identify, within the absorption map, an initial portion of a gas plume boundary; and
use the initial portion of the gas plume boundary to identify, within the absorption map, one or more absorption levels associated with one or more specific additional sampled locations as indicative of gas emission and combining them with the initial portion of identified initial portion of the gas plume boundary to identify a region within the absorption map as corresponding to the gas plume.

20. The system of claim 19, wherein the instructions cause the processor to use the identified region corresponding to the gas plume to determine a location and/or leak rate of a gas leak from which the gas plume originates.

21. The system of claim 15, wherein the instructions cause the processor to use the absorption levels of the spectral absorption map to determine, for each of at least a portion of the plurality of sampled locations, a column density of one or more of the compounds of interest.

22. The system of claim 15, wherein the one or more spectral bands of interest are within the short-wave infrared (SWIR) spectrum.

23. The system of claim 15, wherein the one or more detectors are operable to detect light within the short-wave infrared (SWIR) spectrum.

24. The system of claim 15, wherein each of at least a portion of the one or more spectral bands of interest span an extended spectral feature, comprising a plurality of absorption lines of the one or more compounds of interest.

25. The system of claim 15, comprising two or more mechanically coupled mirrors aligned to maintain overlap between the ifov and the beam of illumination while they are scanned.

26. The system of claim 15, wherein the reflector installment comprises one or more reflective sections mounted in proximity to, and/or mounted on, one or more assets within the site.

27. The system of claim 15, wherein the reflector installment comprises one or more reflective sections, each comprising a continuous reflective surface of sufficient size to span at least a portion of the plurality of sampled locations on the reflector installment.

28. The system of claim 15, wherein the reflector installment comprises one or more continuous retro-reflective surfaces.

* * * * *